(12) United States Patent
Pepys

(10) Patent No.: US 7,910,106 B2
(45) Date of Patent: Mar. 22, 2011

(54) COMBINATIONS OF SAP DEPLETING AGENTS AND ANTI-SAP ANTIBODIES

(75) Inventor: Mark B. Pepys, London (GB)

(73) Assignee: Pentraxin Therapeutics Ltd., London (GB)

( * ) Notice: Subject to any disclaimer, the term of this patent is extended or adjusted under 35 U.S.C. 154(b) by 0 days.

(21) Appl. No.: 12/346,023

(22) Filed: Dec. 30, 2008

(65) Prior Publication Data

US 2009/0191196 A1 Jul. 30, 2009

Related U.S. Application Data

(63) Continuation-in-part of application No. PCT/EP2008/058333, filed on Jun. 27, 2008.

(30) Foreign Application Priority Data

Jun. 27, 2007 (GB) .................................. 0712503.2

(51) Int. Cl.
*A61K 39/395* (2006.01)
*A61K 31/40* (2006.01)
*A61K 31/401* (2006.01)
*C07K 16/18* (2006.01)
*C07D 207/18* (2006.01)

(52) U.S. Cl. ..................... 424/145.1; 514/408; 514/422; 514/423; 530/388.25; 530/387.1; 530/387.9; 548/400; 548/524; 548/565

(58) Field of Classification Search ........................ None
See application file for complete search history.

(56) References Cited

FOREIGN PATENT DOCUMENTS

| EP | 0620276 A1 * | 10/1994 |
| EP | 0915088 | 5/1999 |
| WO | WO9505394 A1 | 2/1995 |
| WO | WO2004059318 | 7/2004 |
| WO | WO2004099173 | 11/2004 |

OTHER PUBLICATIONS

Kuby J. Immunology, Third Edition, 1997, W.H. Freeman & Co., New York, pp. 131-134.*
Alberts B et al. Molecular Biology of the Cell, 3rd Edition, 1994, pp. 1216-1220.*
Hazenberg BP et al. Diagnostic performance of 123I-labeled serum amyloid P component scintigraphy in patients with amyloidosis. Am J Med. Apr. 2006; 119(4):355.e15-24.*
Santa Cruz Biotechnology, Inc. Research Antibodies Catalog '07, entry for SAP (SAP-5) sc-59686, p. 576, Jan 2007.*
Zandman-Goddard G et al. Anti-serum amyloid component P antibodies in patients with systemic lupus erythematosus correlate with disease activity. Ann Rheum Dis. 2005; 64:1698-1702.*
Pepys et al., Targeted pharmacological depletion of serum amyloid P component for treatment of human amyloidosis. Nature. May 16, 2002;417(6886):254-9.

* cited by examiner

*Primary Examiner* — Daniel E Kolker
*Assistant Examiner* — Kimberly A. Ballard
(74) *Attorney, Agent, or Firm* — Vedder Price P.C.; Thomas J. Kowalski; Deborah L. Lu

(57) ABSTRACT

The invention describes the use of an antibody specific for serum amyloid P component, for the treatment or prophylaxis of amyloidosis, and the use of a compound which depletes serum amyloid P component from the circulation in combination with an antibody specific for serum amyloid P component.

42 Claims, 16 Drawing Sheets

```
       136   140    147
h      EQDSYGGKFDRS
m      EQDNYGGGFQRS
```

$K_d$ 10 nM

SEQUENCE LISTING

```
<160> NUMBER OF SEQ ID NOS: 3

<210> SEQ ID NO 1
<211> LENGTH: 204
<212> TYPE: PRT
<213> ORGANISM: Homo sapiens

<400> SEQUENCE: 1

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160
```

```
Asp Ser Val Leu Pro Pro Glu Asn Ile Leu Ser Ala Tyr Gln Gly Thr
                165             170                 175

Pro Leu Pro Ala Asn Ile Leu Asp Trp Gln Ala Leu Asn Tyr Glu Ile
            180             185                 190

Arg Gly Tyr Val Ile Ile Lys Pro Leu Val Trp Val
            195             200

<210> SEQ ID NO 2
<211> LENGTH: 12
<212> TYPE: PRT
<213> ORGANISM: Homo sapiens

<400> SEQUENCE: 2

Glu Gln Asp Ser Tyr Gly Gly Lys Phe Asp Arg Ser
1               5                   10

<210> SEQ ID NO 3
<211> LENGTH: 12
<212> TYPE: PRT
<213> ORGANISM: Mus sp.

<400> SEQUENCE: 3

Glu Gln Asp Asn Tyr Gly Gly Gly Phe Gln Arg Ser
1               5                   10
```

US 7,910,106 B2

COMBINATIONS OF SAP DEPLETING AGENTS AND ANTI-SAP ANTIBODIES

INCORPORATION BY REFERENCE

This application is a Continuation-in-Part of International Patent Application No. PCT/EP2008/058333, filed Jun. 27, 2008, and to United Kingdom patent application Serial No. 0712503.2 filed Jun. 27, 2007.

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SEQUENCE LISTING

The instant application contains a Sequence Listing which has been submitted via EFS-Web and is hereby incorporated by reference in its entirety. Said ASCII copy, created on Jul. 28, 2010, is named 67459907.txt, and is 2,403 bytes in size.

FIELD OF INVENTION

The present invention relates in general to the treatment and/or prevention of diseases which involve amyloid deposition. In particular, the invention relates to the treatment of amyloidosis.

BACKGROUND TO THE INVENTION

Amyloidosis is a serious and usually fatal disease caused by accumulation in the tissues of abnormal insoluble protein fibres known as amyloid fibrils[1]. These are derived from different proteins in different forms of the disease but all amyloid fibrils share a common cross-β core structure and all are derived by misfolding of normally soluble precursor proteins[1]. In addition to the amyloid fibrils themselves, amyloid deposits are always rich in proteoglycans, some of which are tightly bound to the fibrils[2]. A normal non-fibrillar plasma protein, serum amyloid P component (SAP), is also always present in amyloid deposits by virtue of its avid specific calcium dependent binding to all types of amyloid fibrils[3,4].

Human SAP is a constitutive protein in the plasma[5], at a concentration of around 20-40 mg/l and with a total of about 50-100 mg of SAP in the combined plasma and extravascular compartments both of normal individuals and patients with diseases other than amyloidosis[6]. In contrast, in patients with amyloid, SAP is also specifically concentrated in the amyloid deposits and in an individual with extensive systemic amyloidosis there may be as much as 20,000 mg of SAP in the amyloid[7].

Amyloid deposits are extracellular and they cause disease by progressive accumulation until they damage the structure and thus the function of whatever tissue they occupy[1]. There is very rarely any inflammatory or 'foreign body' response to amyloid deposition, either seen locally in the tissues or suggested by systemic markers of inflammation. In so called systemic amyloidosis the deposits can be present in any tissue or organ in the body but deposits are never seen within the brain substance in these forms of the disease. Systemic amyloidosis is the cause of about 1 per 1000 of all deaths in developed countries, and is always fatal unless the abundance of the protein which is the precursor of the amyloid fibrils can be sufficiently and persistently reduced. This is difficult to achieve in many forms of amyloidosis and may be impossible, and there is thus a major unmet medical need[1,8]. Local forms of amyloidosis, in which the deposits are confined to a single anatomical site or a single tissue or organ system also occur and may cause serious disease[1,8].

In amyloidosis the damage to the structure and function of tissues and organs which leads to clinical disease is unequivocally caused by the progressive accumulation of the amyloid deposits themselves. However there are other conditions in which amyloid deposits are always present, most importantly Alzheimer's disease and type 2 diabetes mellitus, in which the contribution of the amyloid deposition to the pathogenesis of disease, specifically loss of cognitive and pancreatic islet function respectively, is not known[1]. However, amyloid deposits anywhere else in the body are demonstrably pathogenic and it is likely that the cerebral amyloid deposits of Alzheimer's disease and the islet amyloid deposits of type 2 diabetes are also harmful. Since treatment which clears amyloid deposits in systemic and local amyloidosis will certainly be therapeutic, removal of the amyloid deposits in Alzheimer's disease and type 2 diabetes should also be clinically beneficial.

Systemic amyloid A protein (AA) amyloidosis is readily induced in mice by chronic inflammation following intravenous injection of an extract of amyloidotic tissue containing amyloid fibrils, and known as amyloid enhancing factor[9]. This model very closely resembles human AA amyloidosis with major amyloid deposition in the spleen and liver[10]. With the relatively brief period of amyloid induction, for example as used in the experiments described herein, there is very little amyloid deposition elsewhere. The AA protein which forms the amyloid fibrils is derived from its circulating precursor, serum amyloid A protein (SAA), which is an acute phase protein. The plasma concentration of SAA rises sharply from its normal trace value of less than 5 mg/l in response to almost any form of inflammation and tissue damage and can persist at values up to 1000 mg/l, or even more, in the face of persistent stimulation. This increased production of SAA is a necessary precondition for development of AA amyloidosis, and both in humans and in mice, when the SAA concentration falls to normal, amyloid deposition stops and existing amyloid deposits can regress[10-12]. In the absence of continued SAA production, spontaneous regression of AA amyloid deposits is universal in the mouse model but proceeds at a variable rate which must be appropriately accommodated in the design of therapeutic experiments.

European patent application EP 0 915 088 discloses compounds which are competitive inhibitors of binding of SAP to amyloid fibrils, as well as methods for their manufacture. A preferred compound disclosed in EP 0 915 088 is (R)-1-[6-[(R)-2-Carboxy-pyrrolidin-1-yl]-6-oxo-hexanoyl]pyrrolidine-2-carboxylic acid (CPHPC), however, any of the compounds described therein, or any other compound which depletes circulating SAP can be used in the practice of the present invention. International Patent Application WO 2004/099173, incorporated herein by reference, also describes palindromic compounds that could also be used in the practice of the present invention.

In human SAP transgenic mice, human SAP is present in both the circulation and the amyloid deposits. The drug (R)-1-[6-[(R)-2-Carboxy-pyrrolidin-1-yl]-6-oxo-hexanoyl]pyrrolidine-2-carboxylic acid (CPHPC) is specifically bound by human SAP in a complex composed of two native pentameric SAP molecules and 5 CPHPC molecules[16]. This complex is recognised as abnormal by the liver and is very rapidly taken up by the hepatocytes and degraded, thus efficiently clearing SAP from the circulation[16]. Plasma SAP concentrations remain very low for as long as the drug is administered[16]. CPHPC is extremely well tolerated and neither the drug itself nor the SAP depletion it produces have caused any adverse effects[16]. There is evidence of clinical benefit from CPHPC treatment in human systemic amyloidosis patients, especially with respect to preservation of renal function in individuals with predominantly renal amyloidosis.

However, despite these promising observations with CPHPC, swift and optimal therapeutic efficacy capable of preserving organ function and prolonging life in patients with systemic amyloidosis will require substantial or complete clearance of the amyloid deposits.

International patent application WO04/059318 describes methods which are asserted to enhance fibrocyte formation which comprise the provision of compositions which bind SAP. Such compositions include anti-SAP antibodies and CPHPC. However, WO04/059318 does not describe the treatment of diseases associated with amyloid deposition. Moreover, WO04/059318 does not describe the specific combination of an anti-SAP antibody and CPHPC. Furthermore, recent data indicate that SAP is not associated with fibrocyte inhibition, and thus that SAP depletion does not enhance fibrocyte production[20].

Accordingly, there is a need in the art for improved therapeutic efficacy in patients with systemic amyloidosis to preserve organ function and prolong life.

Citation or identification of any document in this application is not an admission that such document is available as prior art to the present invention.

SUMMARY OF THE INVENTION

The present invention is based, at least in part, on the surprising finding that this can now be achieved by treatment with a compound which effectively depletes human SAP from the circulation, and additionally treatment with an antibody specific for SAP.

In a first aspect, therefore, there is provided a pharmaceutical composition comprising a compound which depletes serum amyloid P component (SAP) from the circulation, in combination with an antibody specific for SAP.

Preferably, the compound which depletes SAP from the circulation is an SAP cross linking agent. It has been found that compounds capable of cross linking a plurality of SAP molecules in the circulation cause the SAP to be rapidly eliminated from the circulation; see WO03/013508. Examples of such compounds include multivalent ligands specific for SAP, for example multivalent competitive inhibitors of SAP binding. Competitive inhibitors of binding of SAP to amyloid are set forth, for example in EP 0 915 088, the disclosure of which is incorporated herein by reference; the use of these, and other molecules to deplete SAP from the circulation is described, for instance, in WO03/013508 and Pepys et al.[16], which are also incorporated by reference in their entirety. International Patent Application WO 2004/099173, incorporated herein by reference, also describes palindromic compounds that could also be used in the practice of the present invention. Alternatively, any compound that results in the depletion of circulating SAP can be used in the practice of the present invention.

In a preferred embodiment, the compound which depletes SAP from the circulation is a D-proline; preferred are D-prolines of the Formula:

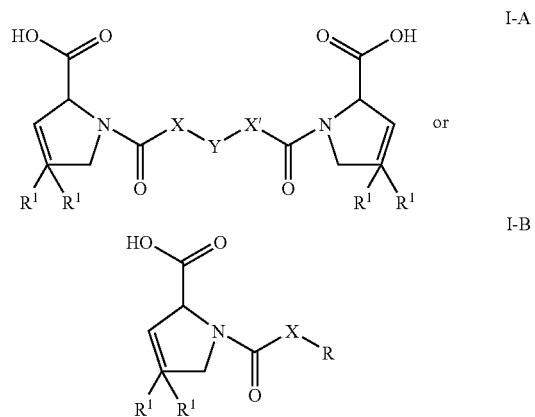

wherein
R is

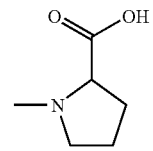

and the group
R$^1$ is hydrogen or halogen;
X—Y—X' is a linker having at least 4, advantageously at least 5, advantageously at least 6, up to 20 linear or straight-chain carbon atoms, wherein
X is —(CH$_2$)$_n$—; —CH(R$^2$)(CH$_2$)$_n$—; CH$_2$—O—(CH$_2$)$_n$—; CH$_2$NH—; benzyl, —C(R$^2$)=CH—; —CH$_2$CH(OH)—; or thiazol-2,5-diyl;
Y is —S—S—; —(CH)—; —O—; —NH—; —N(R$^2$)—; —CH=CH—; —NHC(O)NH—; —N(R$^2$)C(O)N(R$^2$)—; —N[CH$_2$C$_6$H$_3$(OCH$_3$)$_2$]—; —N(CH$_2$C$_6$H$_5$)—; —N(CH$_2$C$_6$H$_5$)C(O)N(CH$_2$C$_6$H$_5$)—; —N(alkoxyalkyl)-; N(cycloalkyl-methyl)-; 2,6-pyridyl; 2,5-furanyl; 2,5-thienyl; 1,2-cyclohexyl; 1,3-cyclohexyl; 1,4-cyclohexyl; 1,2-naphthyl; 1,4-naphthyl; 1,5-naphthyl; 1,6-naphthyl; biphenylen; or 1,2-phenylen, 1,3-phenylen and 1,4-phenylen, wherein the phenylen groups are optionally substituted by 1-4 substituents, selected from halogen, lower alkyl, lower alkoxy, hydroxyl, carboxy, —COO-lower alkyl, nitrilo, 5-tetrazol, (2-carboxylic acid pyrrolidin-1-yl)-2-oxo-ethoxy, N-hydroxycarbamimidoyl, 5-oxo[1,2,4oxadiazolyl, 2-oxo [1,2,3,5] oxathiadiazolyl, 5-thioxo[1,2,4]oxadiazolyl and 5-tert-butylsulfanyl-[1,2,4]oxadiazolyl;
X' is —(CH)—; —(CH)CH(R$^2$)—; —(CH$_2$)$_n$OCH$_2$—; —NHCH$_2$—; benzyl, —CH=C(R$^2$)—; CH(OH)CH$_2$; or thiazol-2,5-diyl;
R$^2$ is lower alkyl, lower alkoxy or benzyl and
n is 0-3,
or a pharmaceutically acceptable salt or mono- or diester thereof. The compound which depletes SAP from the circulation, including the preferred embodiments mentioned above, is referred to hereinafter as an SAP-depleting compound.

In one embodiment, D-proline of formula I-A above can be written as Ligand-linker-Ligand, wherein the X—Y—X' moiety of formal I-A forms the linker. It is within the scope of the present invention that the linker (X—Y—X') can be from 4 to 20 linear carbon atoms in length, including from 4-15 linear carbon atoms, 5-10 linear carbon atoms, and 6-8 linear carbon atoms in length. The linker can be a straight or branched chain, or can optionally form one or more ring structures, with the proviso that at least 4 linear or straight-chain carbon atoms are present in the linker. In one embodiment, at least one of the linear or straight-chain C atoms can be optionally substituted by at least one hetero atom selected from N, O, or S, advantageously O or S, preferably O.

In one embodiment, the D-proline is (R)-1-[6-[(R)-2-Carboxy-pyrrolidin-1-yl]-6-oxo-hexanoyl]pyrrolidine-2-carboxylic acid (CPHPC).

Preferably, the composition does not comprise ethanolamines and/or phosphoethanolamines and/or 4,6-pyruvate acetyl of β-D galactopyranose and/or calcium and/or IL-4 and/or IL-3.

Preferably, the composition is not indicated for enhancing fibrocyte formation. Advantageously, the composition does not enhance fibrocyte formation. Preferably, said antibody specific for SAP does not target a portion of SAP asserted to be functional in inhibiting fibrocyte formation from monocytes.

In a further embodiment, the composition is indicated for use in the treatment of amyloid disease, and there is accordingly provided a pharmaceutical composition comprising an SAP-depleting compound and an antibody specific for SAP for use in the treatment of amyloid disease.

Amyloid disease, as referred to herein, can be any disease which is associated with the extracellular deposition of amyloid fibrils in the tissues. For example, amyloid disease is a disease selected from the group consisting of any form of systemic (visceral) or local amyloidosis, type 2 diabetes and Alzheimer's disease.

In a preferred embodiment, SAP is human SAP, and references to anti-SAP antibodies and SAP-depleting compounds are preferably references to compounds which target and/or deplete human SAP.

In a further aspect, there is provided the use an SAP-depleting compound in combination with an antibody specific for SAP in the manufacture of a composition for the treatment or prophylaxis of amyloid disease.

Treatment with an SAP-depleting compound as defined herein clears almost all the circulating human SAP but leaves substantial amounts of SAP associated with the amyloid deposits in the tissues. The greatest depletion of SAP from amyloid deposits which has been observed in human patients is about 90% after months of continuous CPHPC administration. Intravenous infusion of antibodies against human SAP into patients whose circulating SAP has been depleted enables the antibodies to locate and bind specifically to the amyloid deposits and promote their rapid and extensive regression, with corresponding clinical benefit.

Combination treatment of individuals with established systemic amyloid deposits using the SAP-depleting compound and anti-SAP antibodies safely and effectively causes the rapid and essentially complete clearance of the deposits. To the best of the inventor's knowledge, such deliberate, prompt and targeted clearance of established amyloid deposits has never previously been achieved in any patient or animal model or by any other method.

Advantageously, since SAP is present in all amyloid deposits of all types in human diseases associated with amyloid deposition, including amyloidosis, Alzheimer's disease and type 2 diabetes, this approach to treatment is applicable in all such conditions. Preferably, the invention is for the treatment of amyloidosis.

In a further aspect, there is provided a method for treating a subject suffering from or at risk from amyloid disease, comprising administering to a subject in need thereof a composition comprising an SAP-depleting compound and an antibody specific for SAP.

The SAP-depleting compound and the antibody may be administered simultaneously, for instance separately or in admixture, or sequentially. In one embodiment, the treatment regime comprises administration of the SAP-depleting compound alone, followed by administration of the antibody. Optionally, the SAP-depleting compound administration may be continued during administration of the antibody.

In a third aspect, there is provided a kit for use in the treatment of amyloidosis comprising an SAP-depleting compound and an antibody specific for SAP. The kit components can be provided for simultaneous, simultaneous separate or sequential administration, or a combination thereof.

In a preferred embodiment, the SAP-depleting compound and the anti-SAP antibody are administered sequentially, such that the SAP-depleting compound is administered before the antibody. Administration may be conducted over an extended period of time, by infusion, repeated bolus doses or in any other way; or single dose administration may be employed, in which the SAP-depleting compound and/or the antibody are administered once only.

In a specific embodiment, the SAP-depleting compound is administered over a prolonged period, but the antibody is administered in a single dose.

In a fourth aspect, there is provided a method for identifying an agent that can be used in combination with the SAP-depleting compound for the treatment of amyloidosis, comprising the steps of: (a) contacting a non-human animal with transgenic expression of human SAP in which systemic AA amyloidosis has been induced, with the SAP-depleting compound thereby depleting the circulating SAP; (b) contacting said transgenic non-human animal with one or more agents; and (c) determining if said agent(s) promote substantial or complete regression of the amyloid deposits in the non-human animal, wherein an agent that causes substantial regression of the amyloid deposits in the non-human animal is indicative of an agent that can be used for the treatment of amyloidosis.

Preferably, the transgenic non-human animal is a mouse, suitably a C57BL/6 mouse with the mouse SAP gene deleted and which is transgenic for human SAP.

In a fifth aspect, there is provided a method for identifying an agent that can be used in combination with an SAP-depleting compound for the treatment of amyloidosis, comprising the steps of: (a) administering to a non-human animal in which systemic AA amyloidosis has been induced, a dose of isolated pure human SAP, thereby loading the amyloid deposits with human SAP; (b) contacting said amyloidotic SAP laden non-human animal with one or more agents; and (c) determining if said agent(s) promote substantial or complete regression of the amyloid deposits in the non-human animal, wherein an agent that causes substantial regression of the amyloid deposits in the non-human animal is indicative of an agent that can be used for the treatment of amyloidosis.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE FIGURES

The following detailed description, given by way of example, but not intended to limit the invention solely to the specific embodiments described, may best be understood in conjunction with the accompanying drawings, in which.

Three groups of closely matched C57BL/6 mouse SAP knockout human SAP transgenic pure line mice with established systemic AA amyloidosis, with the same initial amyloid load as shown by whole body $^{125}$I-SAP retention, were treated respectively with CPHPC and a single dose of sheep anti-human anti-SAP antibody, with CPHPC alone or with nothing, and were then killed for estimation of amyloid load 28 days later. Each point represents the amyloid score for a single animal: 0, no amyloid detected; $10^0$, trace specks; $10^1$, perifollicular traces; $10^2$, General perifollicular; $10^3$, heavy perifollicular; $10^4$, heavy perifollicular and interfollicular. In Mann Whitney U tests for the difference between the scores in the groups, the P values were as follows: group 1 vs group 2 P=0.0000; group 1 vs group 3 P=0.0000; group 2 vs group 3 P=0.2635. There were no differences in the amyloid scores between males and females within any of the groups (not shown).

Figure 2:
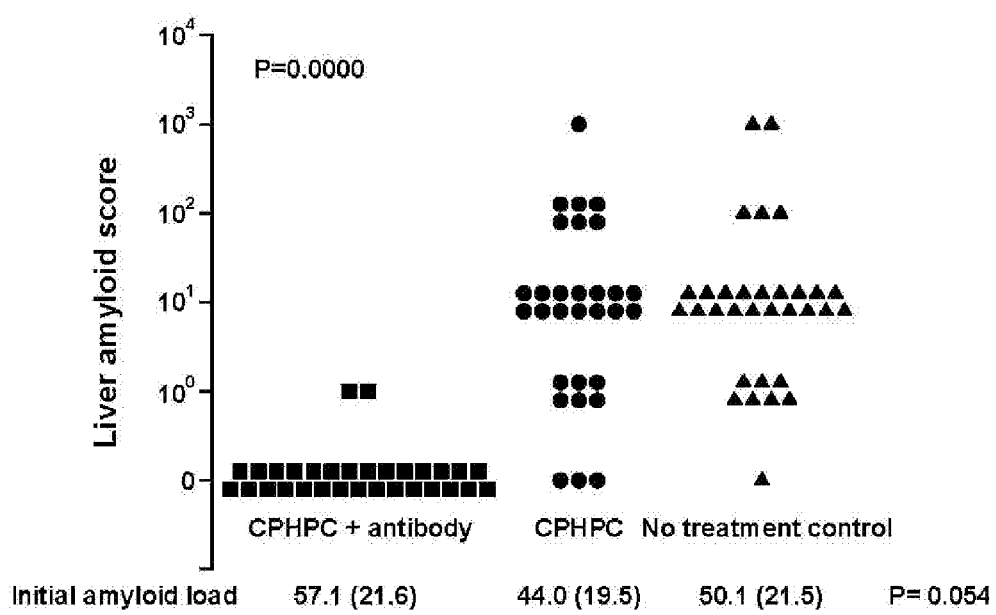
Figure 3A:
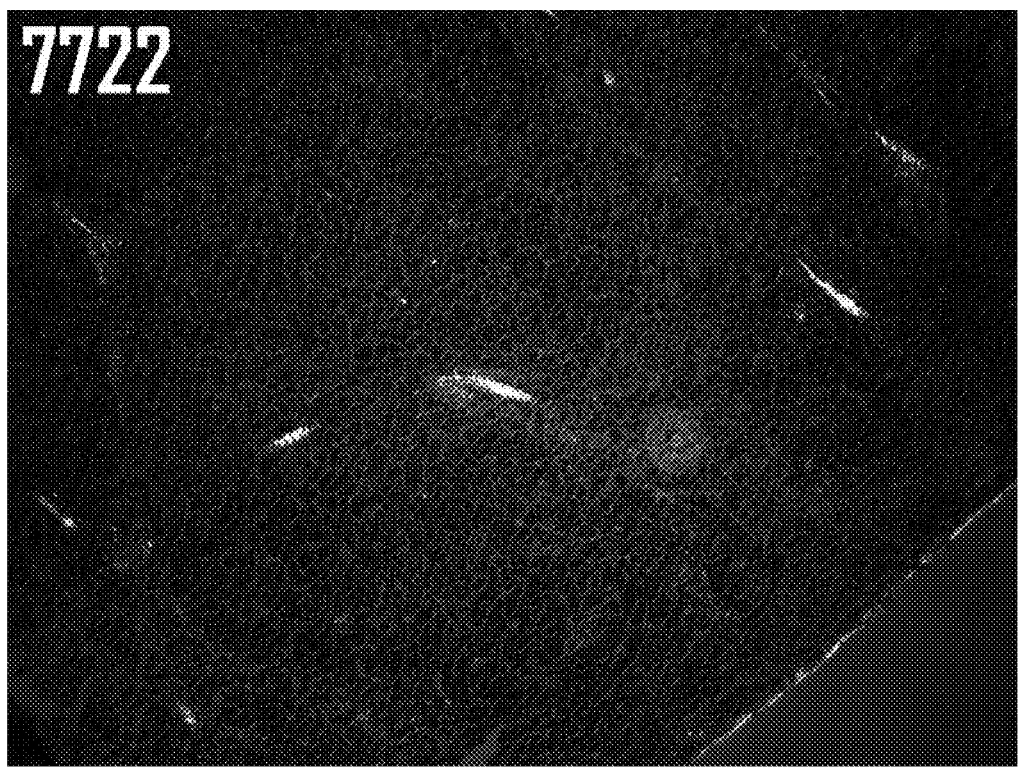
Figure 3B:
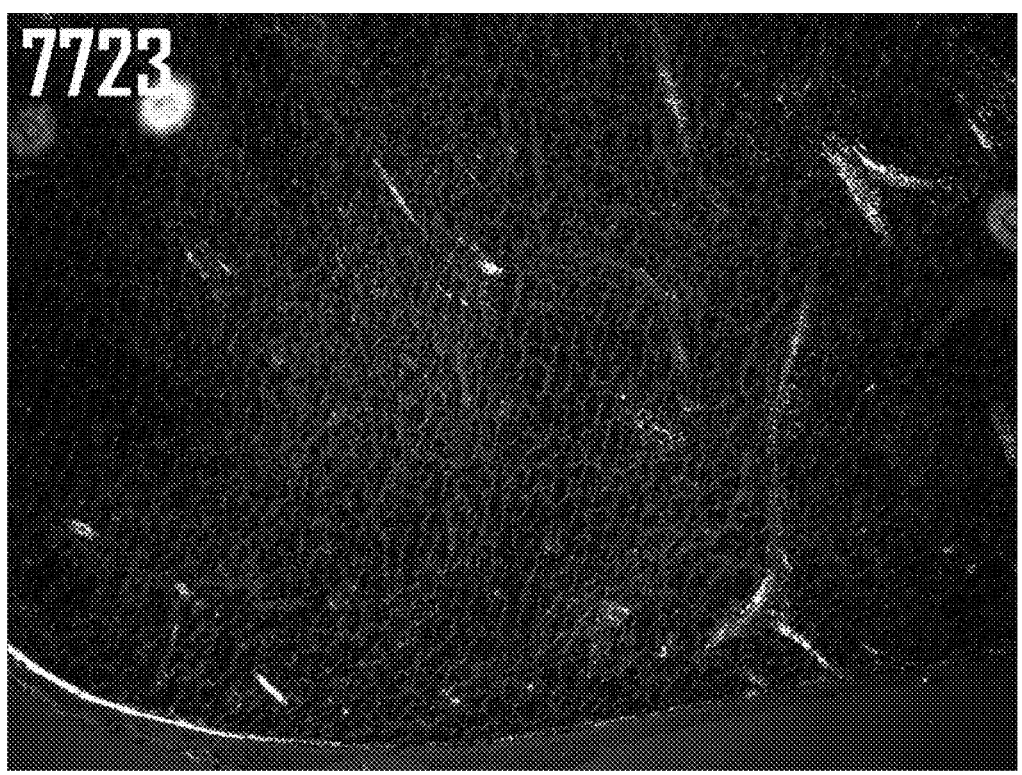
Figure 3C:
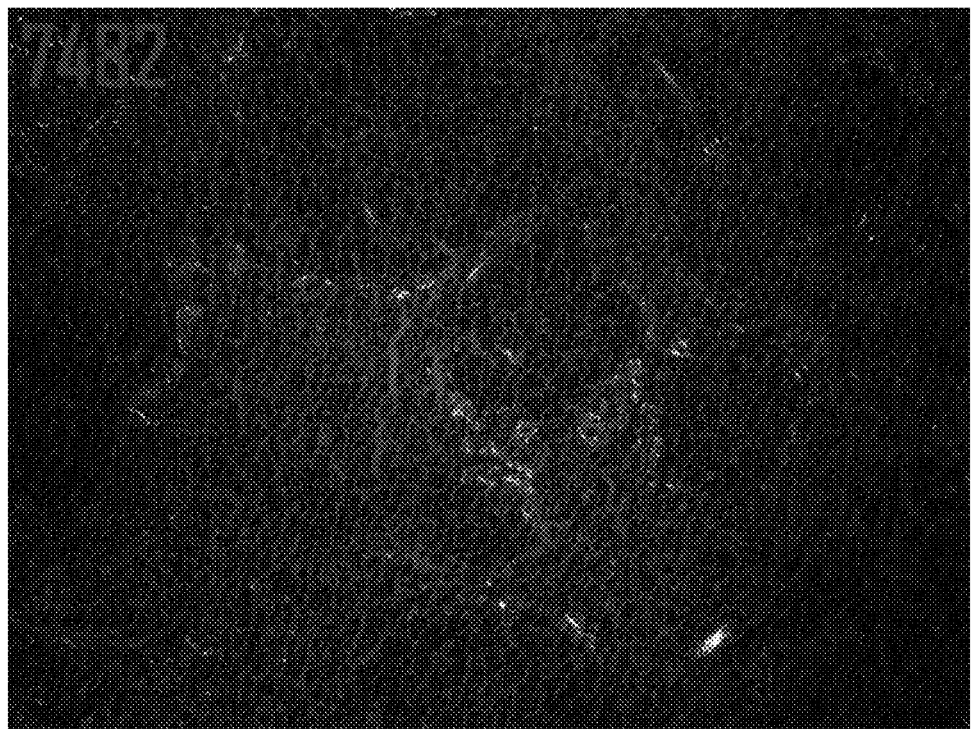
Figure 3D:
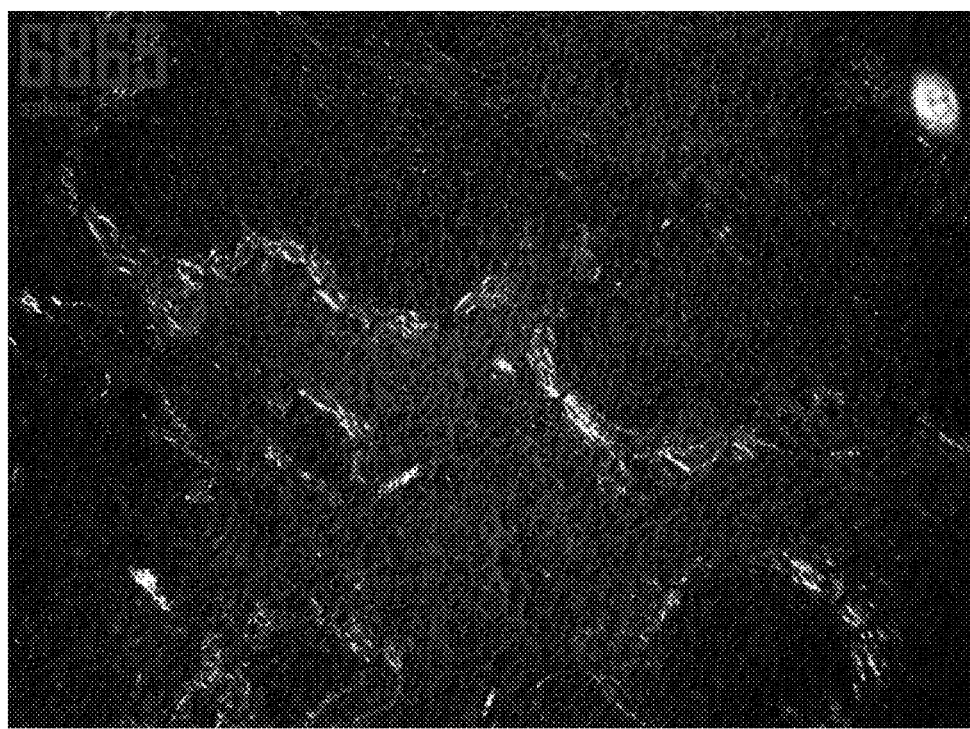
Figure 3E:
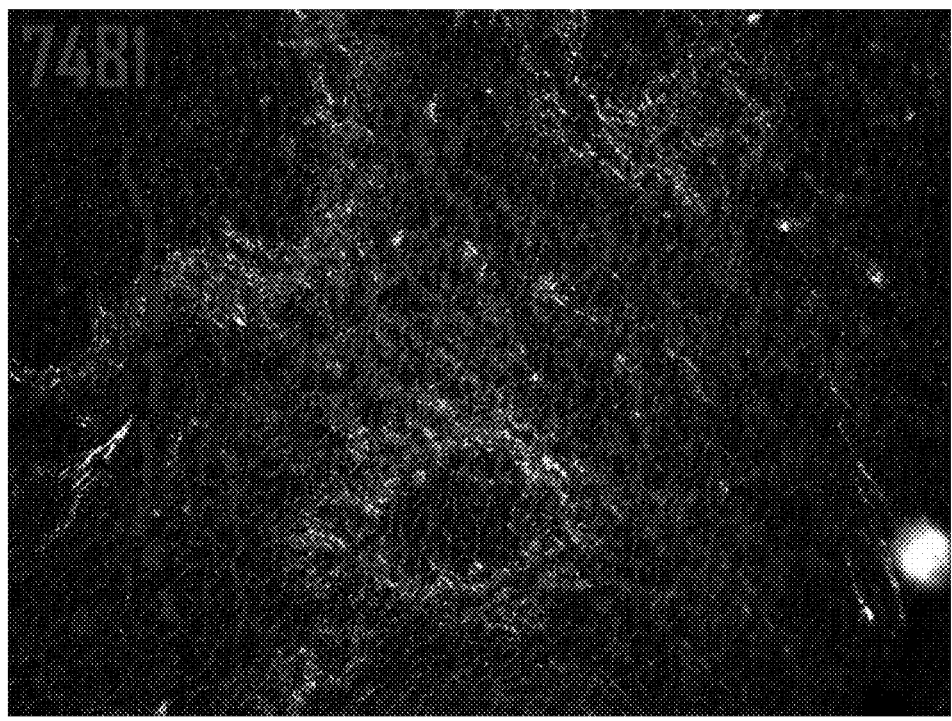
Figure 3F:
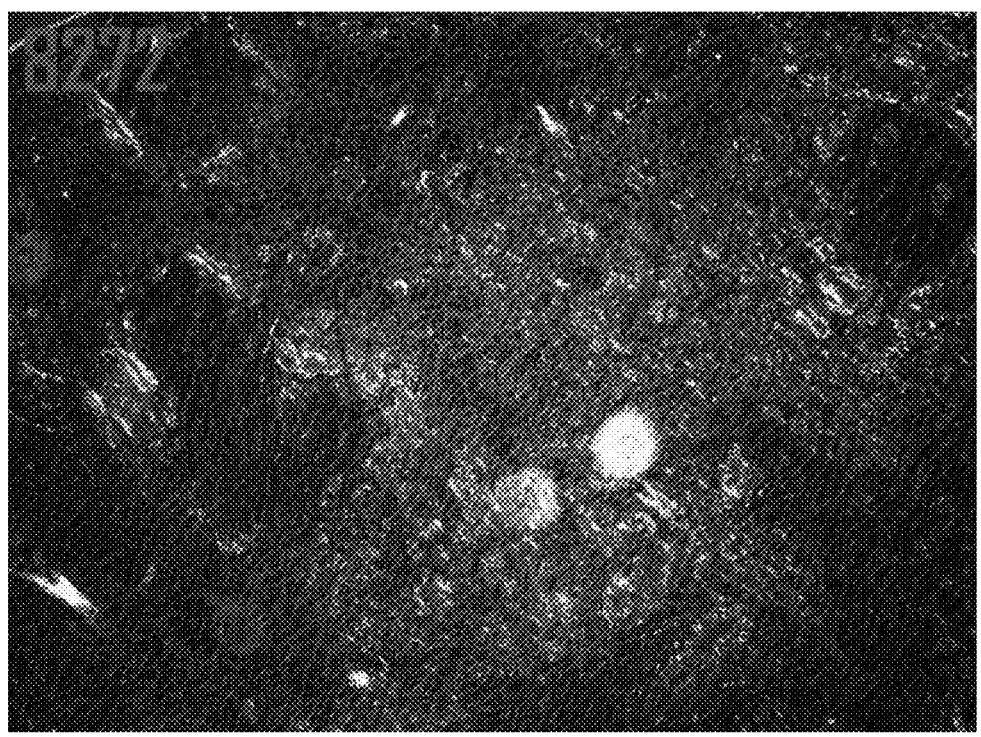
Figure 3G:
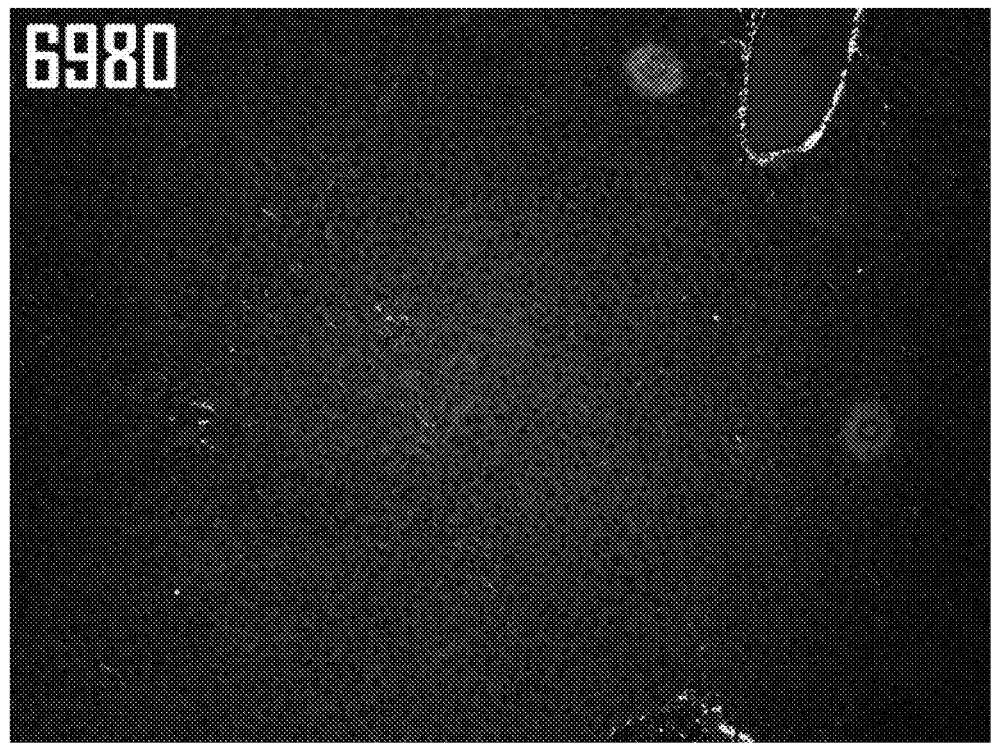
Figure 3I:
Figure 3J:
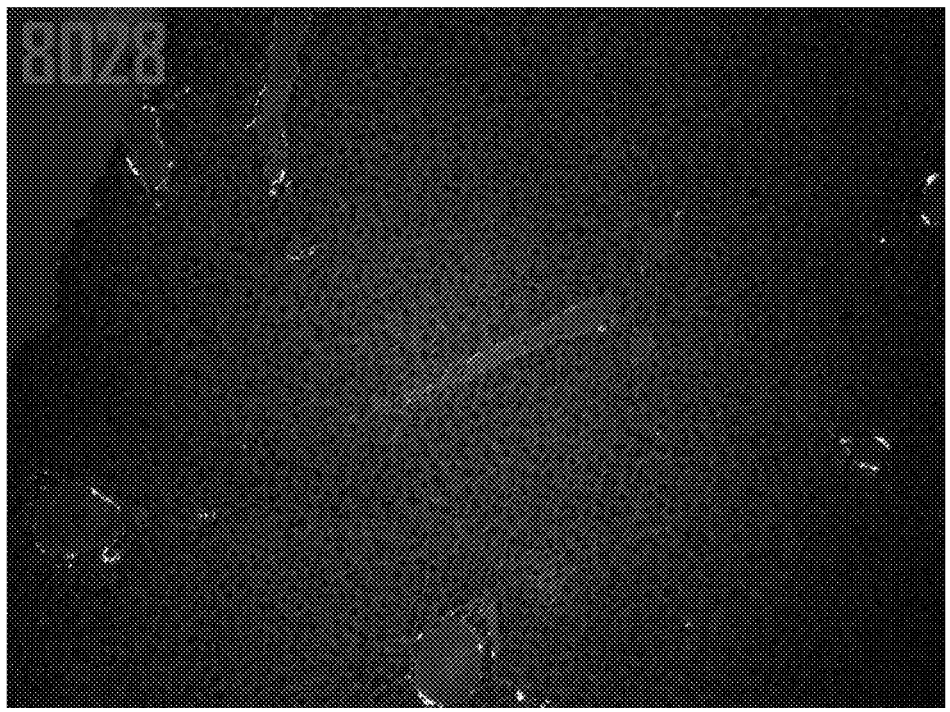
Figure 3K:
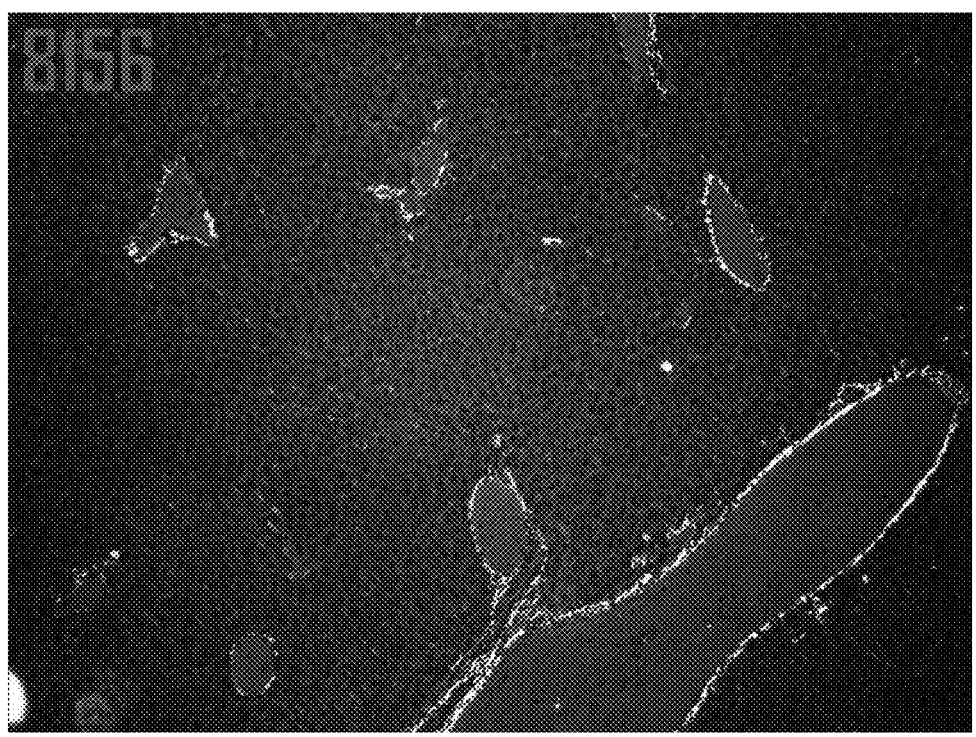
Figure 3L:
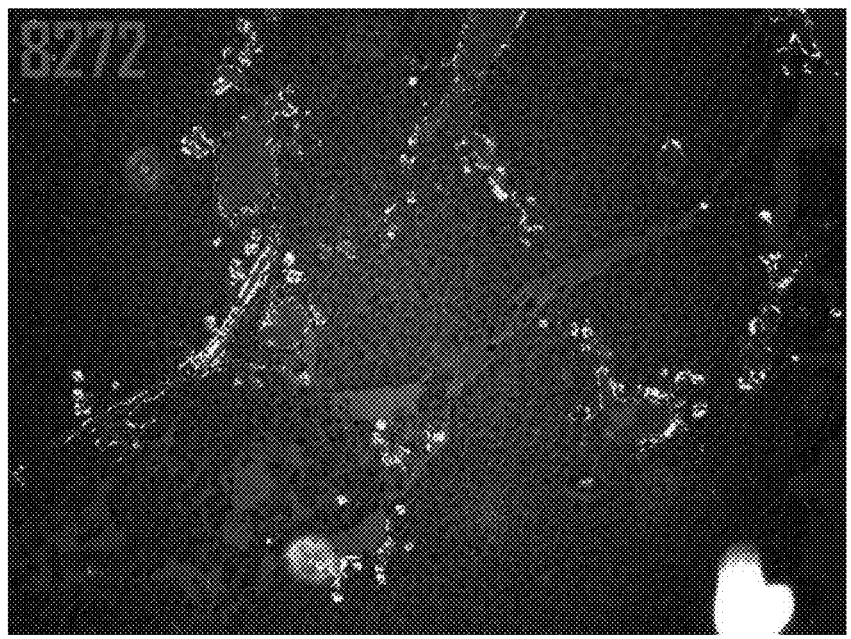
Figure 4A:
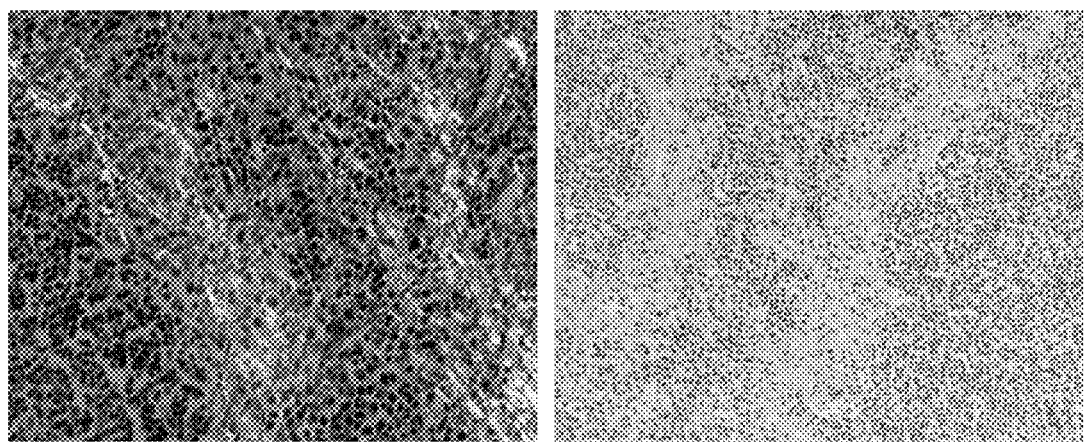
Figure 4B:
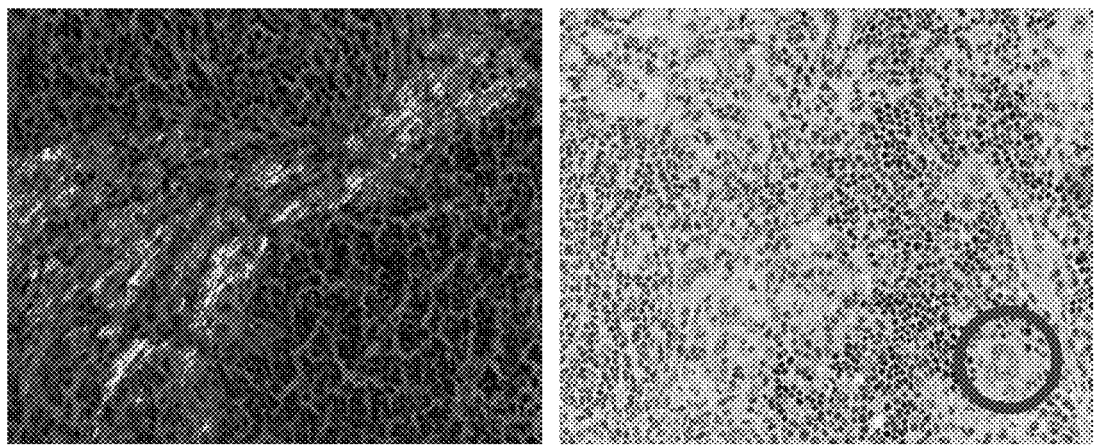
Figure 4C:
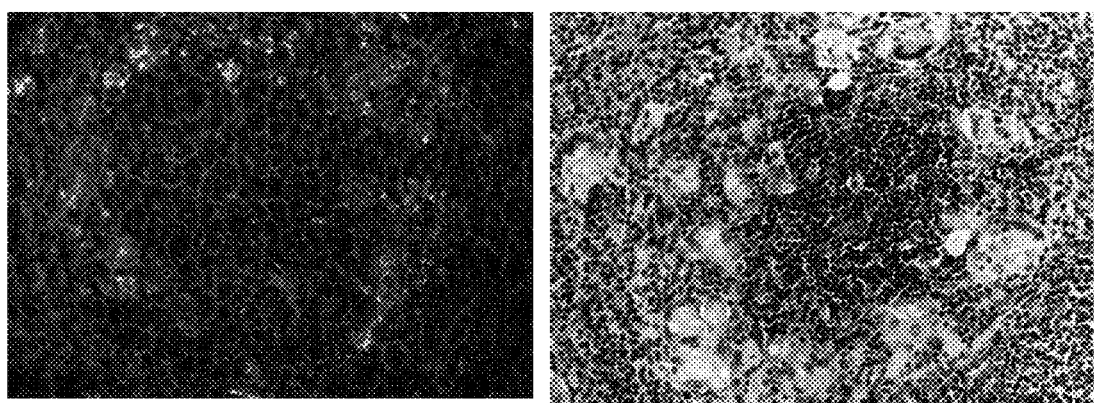
Figure 4D:
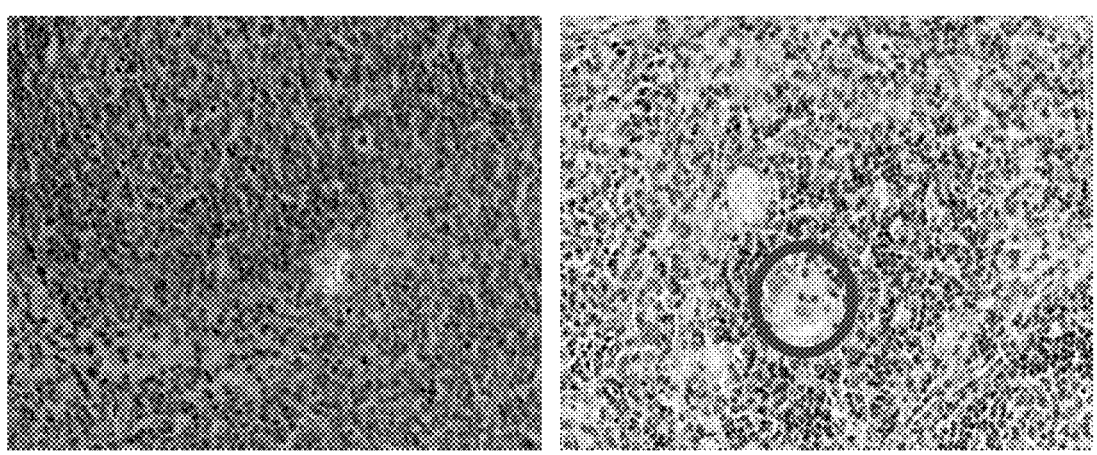

FIG. 2. Amyloid deposits in the livers of mice after treatment.

Three groups of closely matched C57BL/6 mouse SAP knockout human SAP transgenic pure line mice with established systemic AA amyloidosis, with the same initial amyloid load as shown by whole body $^{125}$I-SAP retention, were treated respectively with CPHPC and a single dose of sheep anti-human anti-SAP antibody, with CPHPC alone or with nothing, and were then killed for estimation of amyloid load 28 days later. Each point represents the amyloid score for a single animal: 0, no amyloid detected; $10^0$, trace specks; $10^1$, traces in/around most portal tracts; $10^2$, significant deposits in/around all portal tracts; $10^3$, portal and parenchymal deposits; $10^4$, massive portal and parenchymal deposits. In Mann Whitney U tests for the difference between the scores in the groups, the P values were as follows: group 1 vs group 2 P=0.0000; group 1 vs group 3 P=0.0000; group 2 vs group 3 P=0.4740. There were no differences in the amyloid scores between males and females within any of the groups (not shown).

FIG. 3. Amyloid deposits stained with Congo red and viewed in cross polarised light.

Amyloid is identified by its pathognomonic green birefringence which must be distinguished from the white or other bright birefringence of collagen in the tissues and artefacts of foreign bodies, dust, etc. Spleen amyloid scores: 7722, zero (no amyloid present); 7723, $10^0$ (single speck present); 7482, $10^1$; 6865, $10^2$; 7481, $10^3$; 8272, $10^4$. Liver amyloid scores: 6980, zero (no green birefringent amyloid, only white-yellow collagen birefringence); 7482, $10^1$; 8028, $10^2$; 8156, $10^3$; 8272, $10^4$.

FIG. 4. Time course of cellular infiltration and amyloid destruction after administration of anti-SAP antibody. Spleen sections stained with Congo red and viewed in polarised light (left) and stained with haematoxylin and eosin (right) from animals killed at the times shown after antibody treatment. On day 1 (FIG. 4A) there is abundant green birefringent amyloid in the typical perifollicular marginal zone but in contrast to its usual acellular appearance it is densely infiltrated with predominantly mononuclear inflammatory cells. On day 2 (FIG. 4B) macrophages surrounding the amyloid are already fusing to form multinucleate giant cells. By day 4 (FIG. 4C) the amyloid deposits are clearly less abundant and are fragmenting in association with intense macrophage phagocytic activity and numerous multinucleate giant cells surrounding and engulfing the islands of amyloid. At day 7 (FIG. 4D) much less amyloid is present and there are fewer giant cells but they still clearly contain degraded fragments of amyloid.

Figure 5A:
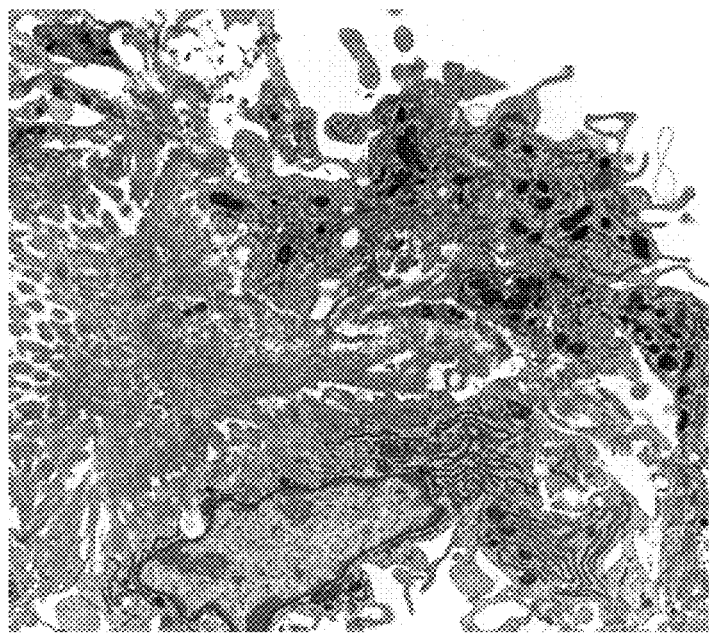
Figure 5B:
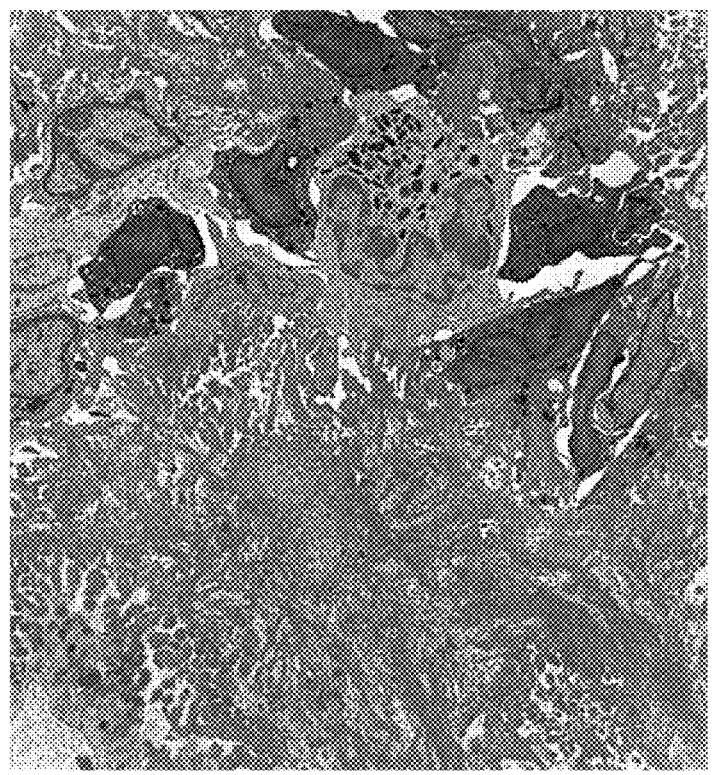
Figure 5C:
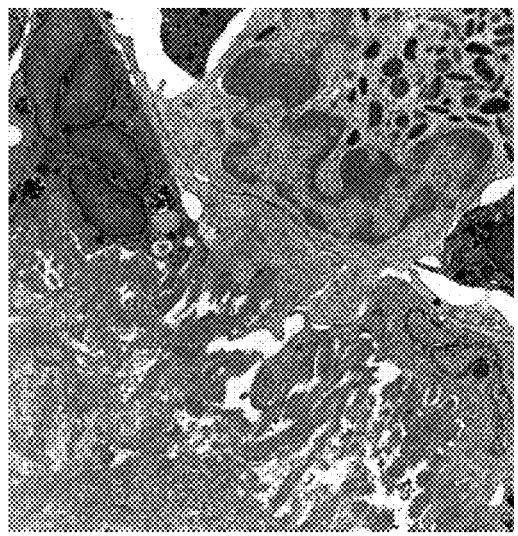
Figure 6A:
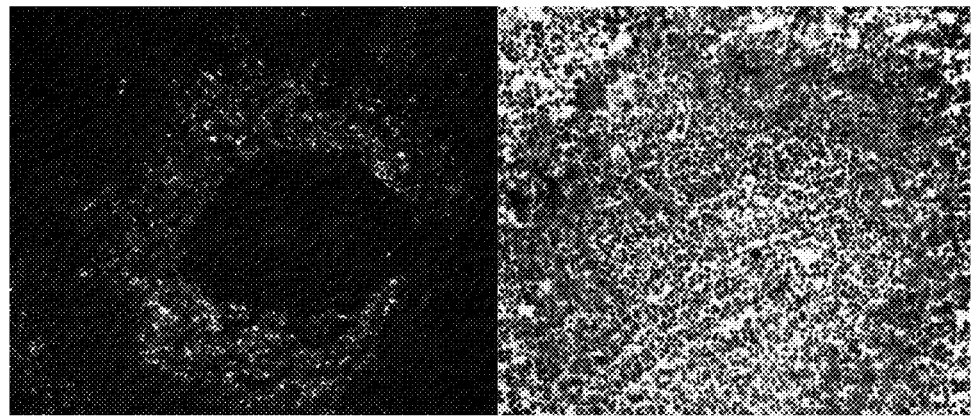
Figure 6B:
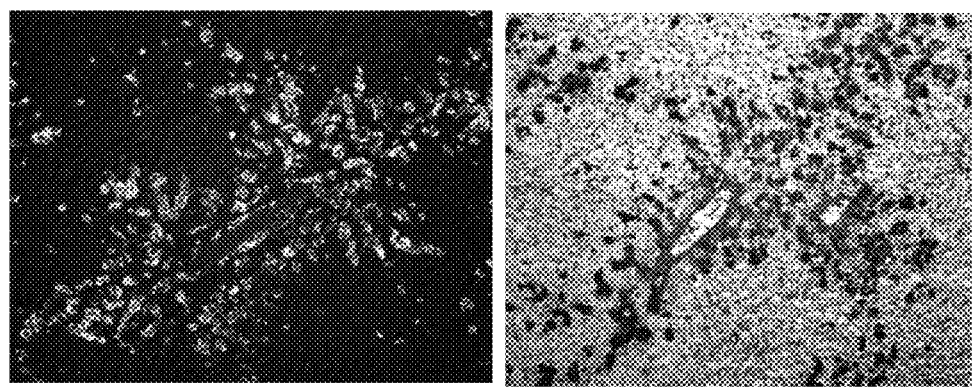
Figure 6C:
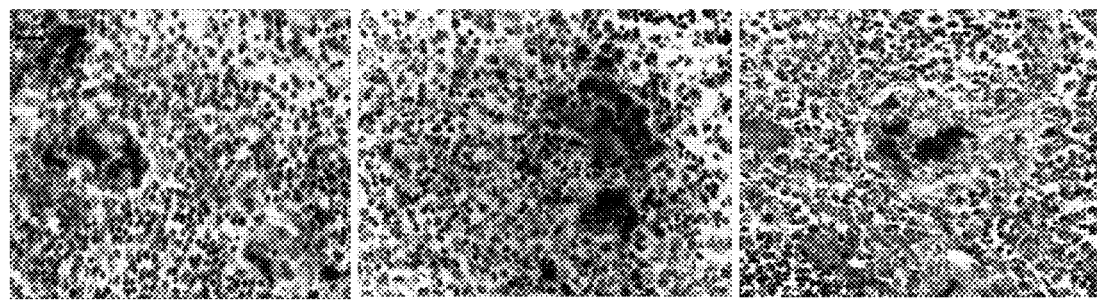
Figure 6D:
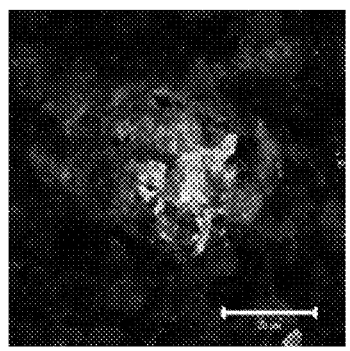

FIG. 5. Electron micrographs of spleen taken 1 day after anti-SAP antibody treatment. FIG. 5A, macrophages (top right) surrounding typical fibrillar amyloid deposit (centre and left); magnification ×4,500. FIG. 5B, granulocytes (upper half of the image) and amyloid deposit (lower half of the image); neutrophils and macrophages have darker cytoplasm; one eosinophil is seen in the centre of the image; ×3,000. FIG. 5C, magnified fragment of an amyloid deposit, granulocytes and macrophages (also seen in 5B); ×7,000.

FIG. 6. Immunochemical identification of cells and proteins in anti-SAP antibody mediated clearance of AA amyloid deposits. Top two panels show the intense macrophage infiltration, identified by strong staining with anti-F4/80, in all congophilic amyloid deposits in spleen and liver. Such staining is completely absent in amyloid deposits of mice not treated with anti-SAP antibody (not shown). Third panel shows the co-localisation of AA amyloid, CD68 (a marker of phagocytic endocytotic activity), and mouse C3. Bottom panel shows phagocytically active macrophages surrounding and engulfing a fragment of mouse AA amyloid. FIG. 6A is day 1 spleen with Congo red, left; anti-F4/80, right; FIG. 6B is day 1 liver with Congo red, left; anti-F4/80, right; FIG. 6C is day 4 spleen with anti-AA protein, left; anti-CD68, centre; anti-mouse C3, right; FIG. 6D is day 4 confocal image with anti-CD68, red; anti-AA protein, green; nuclear conterstain, blue.

Figure 7:
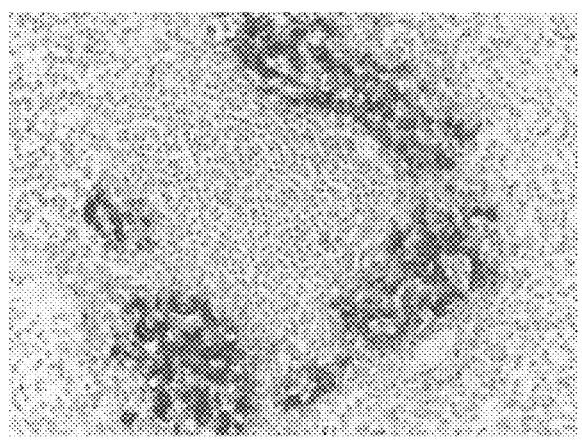

FIG. 7. Immunohistochemical staining with anti-human SAP antibody in spleen of an amyloidotic wild type mouse after injection of isolated pure human SAP. There is strong positive staining of all the amyloid deposits in their typical marginal zone distribution. This bound human SAP is the target of the therapeutic anti-SAP antibody according to the present invention.

Figure 8:
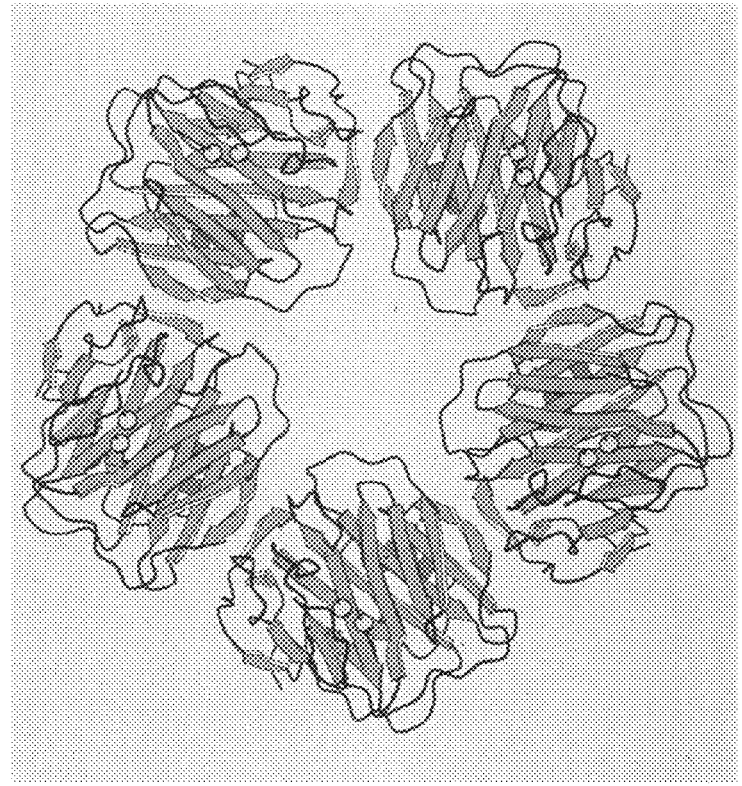
Figure 9A:
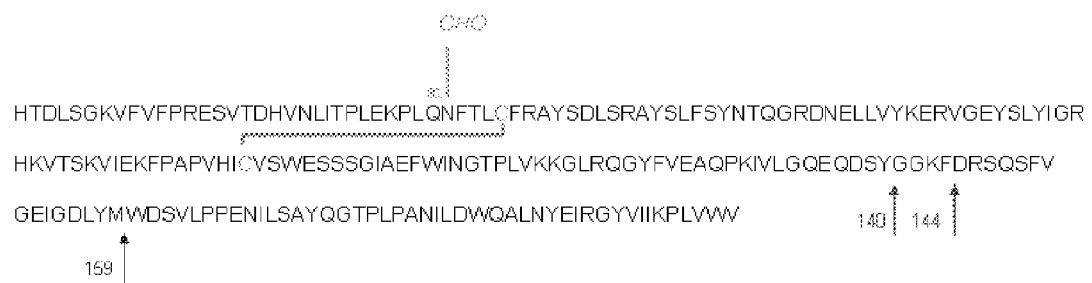
Figure 9B:
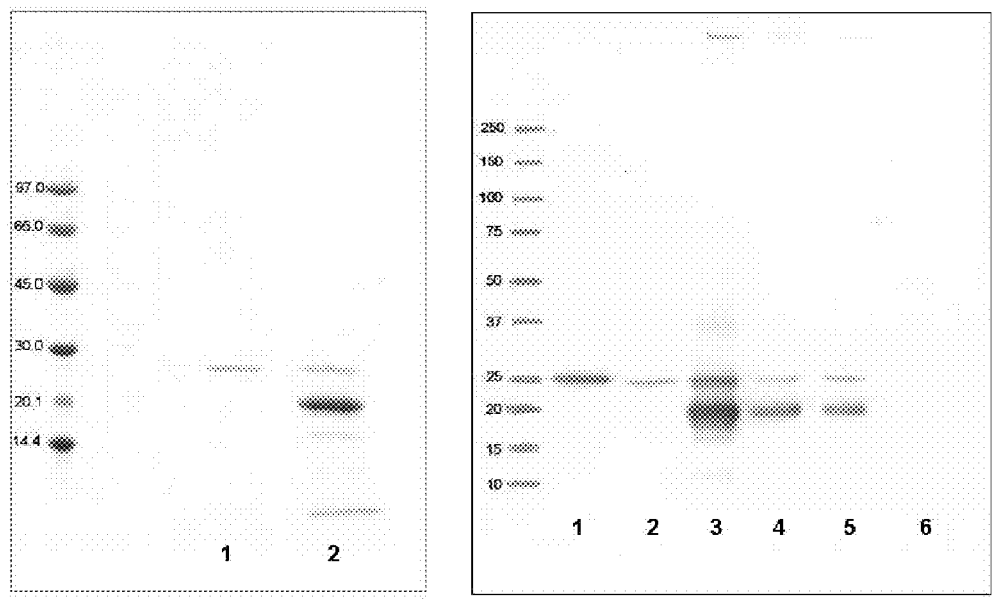
Figure 9C:
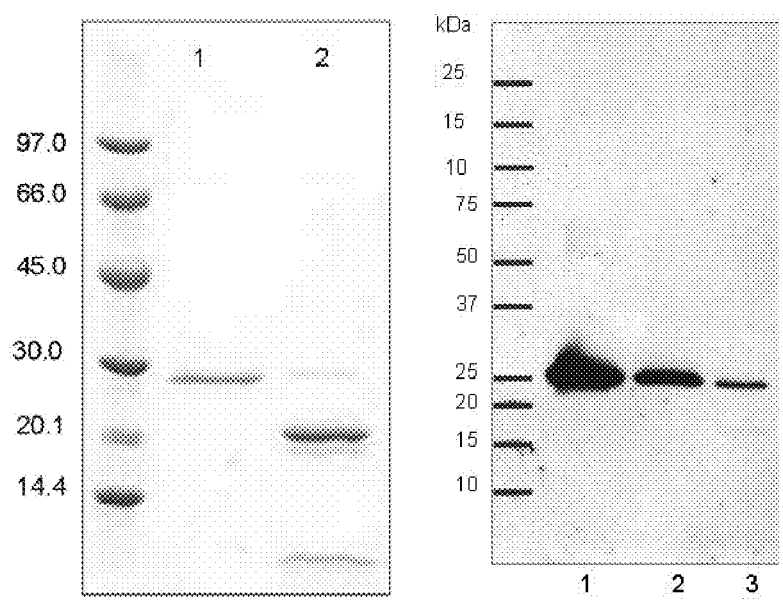
Figure 9D:
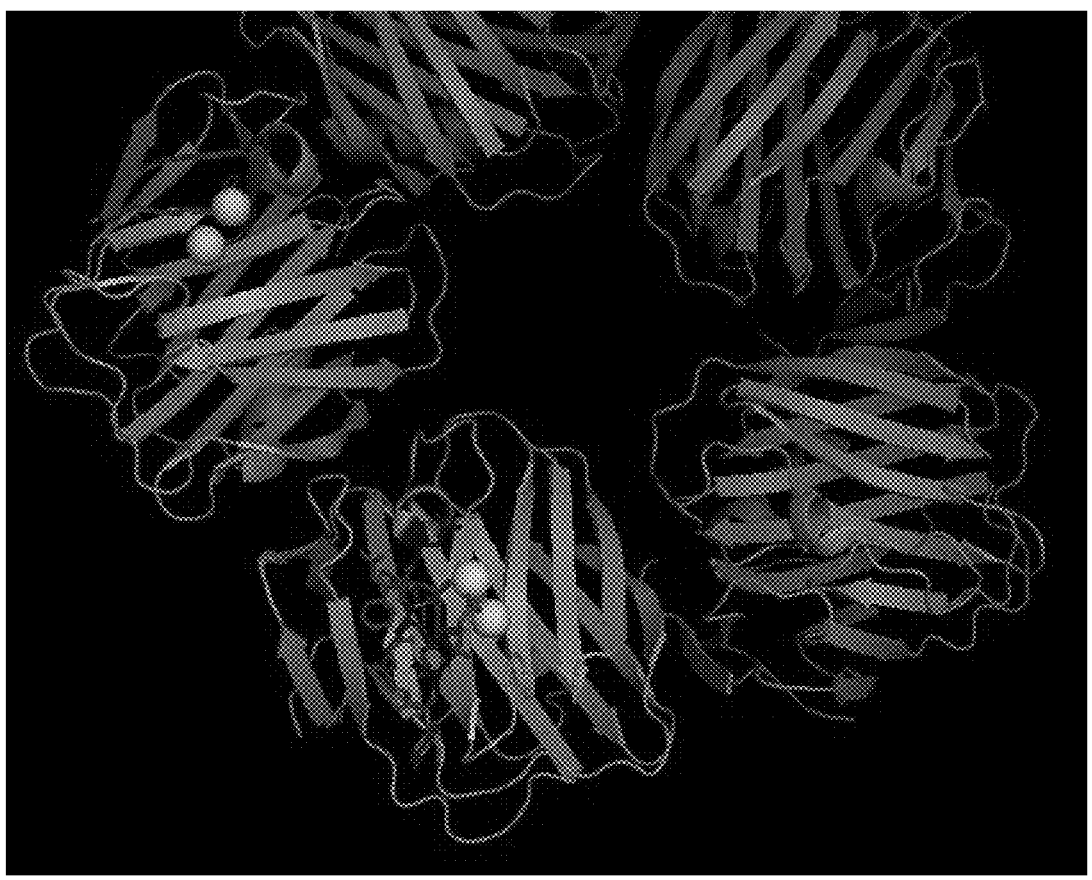

FIG. 8. Three dimensional structure of the SAP molecule. The SAP molecule is composed of five identical non-covalently associated subunits arranged with cyclic pentameric symmetry in a disc-like configuration. On one planar face of the disc each promoter has a short α-helix shown in red and this face is designated the A face. On the opposite face, each protomer has the calcium dependent ligand binding pocket through which SAP recognizes and binds to its ligands, including amyloid fibrils, and is designated as the B face. The two calcium atoms in each binding pocket are shown as yellow spheres.

FIG. 9. Epitope mapping for monoclonal anti-human SAP antibody SAP-5. A, complete amino acid sequence of human SAP (SEQ ID NO: 1) showing the points at which it is cleaved by CNBr in 70% TFA (residue 159M, in blue) and by chymotrypsin, without reduction/carbamidomethylation, in ammonium bicarbonate in the absence of calcium, (residues 140Y and 144F, in red). B, SDS PAGE analysis of SAP cleaved with CNBr. Left panel: Coomassie blue stain; lane 1, untreated control SAP; lane 2, SAP after CNBr cleavage, showing trace residual=cleaved intact protomer and the expected fragments at approximately 20 kD (residues 1-159) and 5 kD (160-204) respectively. These were confirmed by mass spectrometry. Right panel: Western blot with SAP-5 showing intense staining of intact untreated SAP in lanes 1 (100 ng loaded) and 2 (10 ng), and also residual intact SAP and the larger residue 1-159 fragment in CNBr cleaved SAP in lanes 3 (600 ng), 4 (130 ng) and 5 (64 ng). Lane 6 contained isolated pure human CRP with which the SAP-5 did not react at all. C, SDS PAGE analysis of SAP digested with chymotrypsin. Left panel: Coomassie blue stain; lane 1, untreated control SAP; lane 2, SAP after chymotrypsin digestion, showing the expected major fragments corresponding to residues 1-140 and 145-204. These were confirmed by mass spectrometry. Right panel: Western blot with SAP-5 showing intense staining of intact untreated SAP in lanes 1 (500 ng loaded) and 2 (100 ng), and also residual intact SAP in lanes 3 and 4 which contained the chymotrypsin digested SAP at different loadings. Very weak binding of SAP-5 to the residue 1-140 fragment is seen only in lane 3 which was most heavily loaded. Lanes 5 (500 ng) and 6 (100 ng) contained isolated pure human CRP with which the SAP-5 did not react at all. D, Sequence comparison between human SAP (h) (SEQ ID NO: 2) and mouse SAP (m) (SEQ ID NO: 3) for residues 136-147. Top panel, differences indicated above by residues shown in red in the murine sequence. Bottom panel, position of this extended loop with 140Y at its apex shown in red in the 3D structure of human SAP. The different residues in the murine sequence are shown in blue. The yellow spheres represent the calcium atoms bound in the ligand binding pocket of each protomer.

Figure 10:
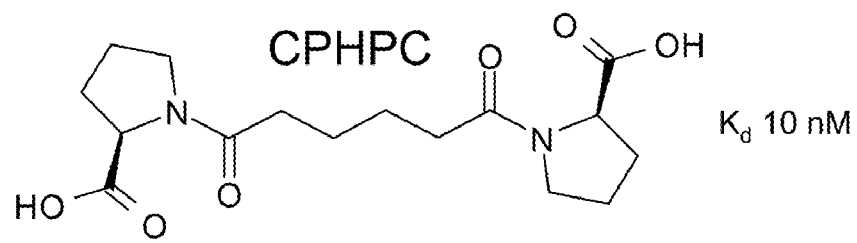
Figure 10:
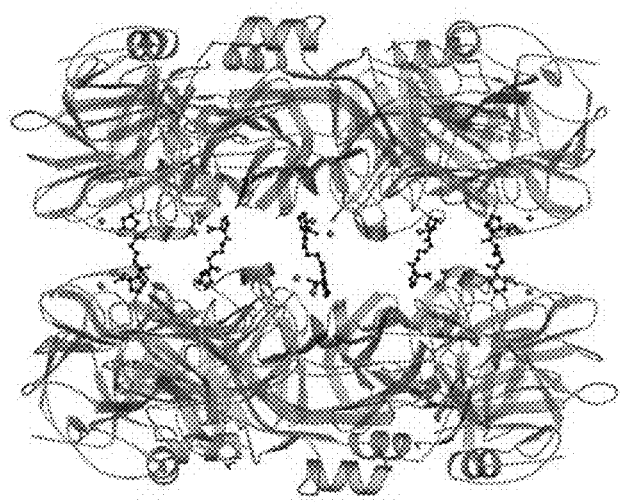

FIG. 10. The complex of SAP with CPHPC. The complex of SAP with CPHPC comprises two pentameric SAP molecules cross linked, B face to B face by 5 CPHPC molecules, the D-proline head groups at either end of which are bound in the calcium dependent ligand binding pockets of opposite pairs of SAP promoters.

Figure 11:
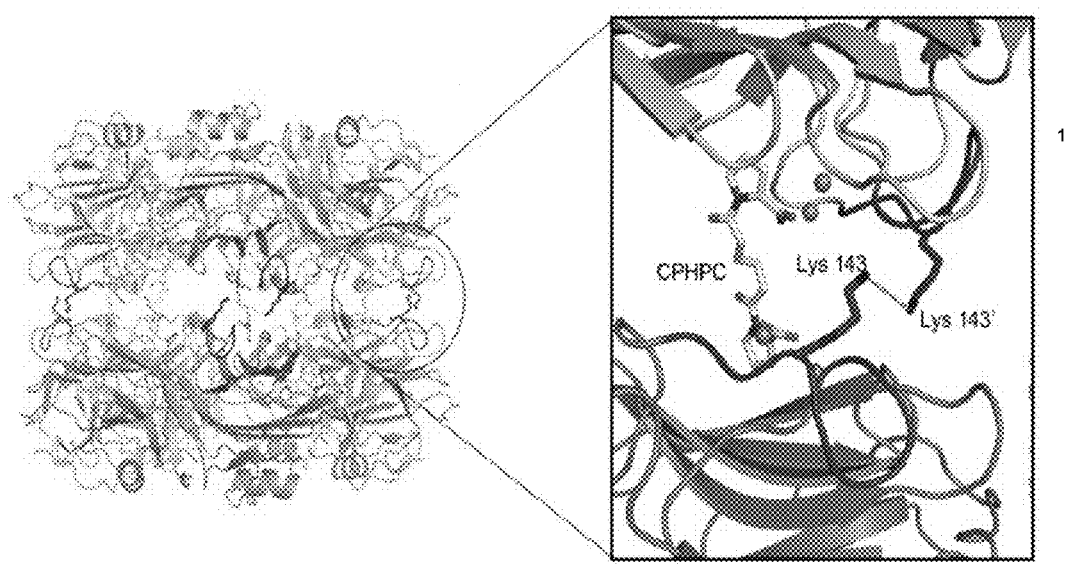

FIG. 11. The complex of SAP and CPHPC cross linked with BS3. The complex of SAP and CPHPC was covalently cross linked using the bifunctional cross linker, BS3, to produce a stable complex in which most of the B face of SAP is occluded exactly as it must be when SAP is bound to amyloid fibrils in vivo. Anti-human SAP antibodies according to the present invention must be able to recognise and bind to SAP when it is in this ligand-bound form.

Figure 12:
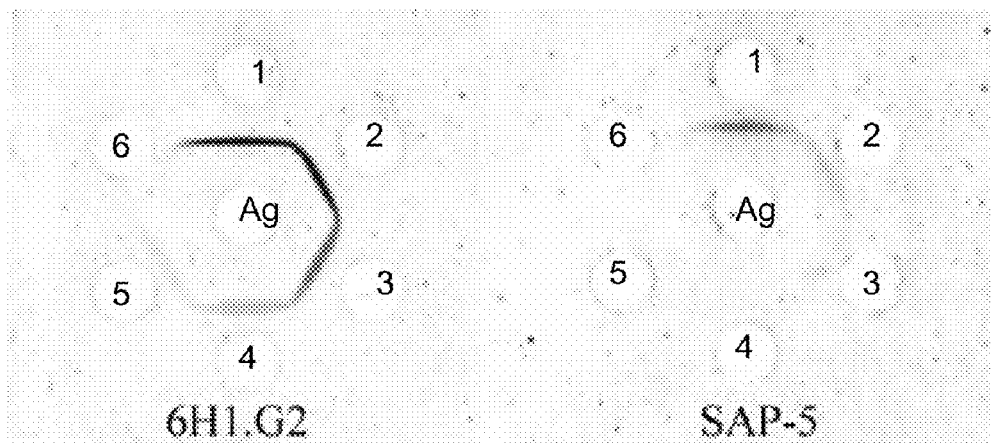

FIG. 12. Immunoprecipitation of human SAP by mouse monoclonal antibodies. Double diffusion in agarose gel between isolated pure human SAP in the center well at 0.5 mg/ml and isolated purified monoclonal antibodies in the surrounding wells at serial doubling dilutions from 1.5 mg/ml (well 1) to 0.04875 mg/ml (well 6). Both SAP-5 and Abp1 (6H1.G2) precipitate with human SAP but Abp1 is notably stronger, showing precipitation even in major antigen excess at well 5 while SAP-5 shows nothing after well 2.

Figure 13:

FIG. 13. Immunoblot analysis of native human SAP and C-reactive protein (CRP). Isolated pure human SAP and CRP were electrophoresed in agarose gel, shown by Coomassie blue staining on the left of each panel, and replicate gels were blotted onto a membrane by standard techniques and then detected using either SAP-5 at 3 µg/ml or Abp1 at 10 µg/ml. Bound mouse IgG was revealed using peroxidise labelled polyclonal rabbit anti-mouse IgG followed by peroxidise substrate and DAB, on the right in each panel. Both SAP-5 and Abp1 bind to human SAP but neither binds to human CRP, the protein most closely related to human SAP with which it shares 55% strict residue-for-residue identity.

DETAILED DESCRIPTION OF THE INVENTION

Amyloidosis

Aspects of the present invention relate to the treatment and/or prevention of disease caused by deposition of amyloid in the tissues, such disease being known as amyloidosis.

The terms "prophylaxis", "prevention", "prevent", "preventing", "suppression", "suppress" and "suppressing" as used herein refer to a course of action (such as administering one or more compounds or pharmaceutical compositions) initiated (e.g., prior to the onset of a clinical symptom of amyloidosis) so as to prevent, suppress or reduce, either temporarily or permanently, the onset of a clinical manifestation of amyloidosis.

The terms "treatment", "treat" and "treating" as used herein to refer to a course of action (such as administering one or more compounds or pharmaceutical compositions) initiated after the onset of clinical manifestations of amyloidosis so as to eliminate or reduce, either temporarily or permanently, a clinical manifestation or progression of amyloidosis.

Amyloidosis is any disease characterized by the extracellular accumulation of amyloid in various organs and tissues of the body.

The term "amyloid" refers to extracellular deposits in the tissues of insoluble protein fibres composed of fibrils with characteristic ultrastructural morphology, a cross-β sheet core structure and the pathognomonic histochemical tinctorial property of binding Congo red dye from alkaline alcoholic solution and then giving red-green dichroism when viewed microscopically in strong cross polarised light. About 25 different unrelated proteins are known to form amyloid fibrils which deposit in human tissues and share all these typical properties. Amyloid deposits in the brain substance, cerebral amyloid, differ somewhat from amyloid deposits elsewhere in the body in that they are always focal and microscopic in size, and are commonly referred to as amyloid plaques.

Amyloidosis, that is disease directly caused by deposition of amyloid in the tissues, comprises both local amyloidosis, in which the deposits are confined to one anatomical region and/or one tissue or organ system, and systemic amyloidosis in which the deposits can occur in any organ or tissue in the body, including blood vessels and connective tissues. The cause of amyloidosis can be either acquired or hereditary. Acquired amyloidosis arises as a complication of a preceding medical condition, which can itself be either acquired or hereditary. Thus reactive systemic amyloidosis, known as amyloid A protein (AA) type is a complication of chronic active inflammatory diseases such as rheumatoid arthritis, juvenile rheumatoid arthritis, Crohn's disease, chronic infections and chronic sepsis, and of hereditary periodic fever syndromes such as familial Mediterranean fever, Muckle-Wells syndrome and CINCA syndrome. Dialysis related amyloidosis is caused by accumulation of $\beta_2$-microglobulin as a result of end stage renal failure. Monoclonal immunoglobulin light chain (AL) amyloidosis is a complication of multiple myeloma or otherwise benign monoclonal gammopathy (monoclonal gammopathy of uncertain significance, MGUS). Acquired amyloidosis of transthyretin type can occur without any preceding illness and is merely a complication of old age. Hereditary amyloidosis is caused by mutations in the genes for various proteins which encode expression of variant proteins having an increased propensity to form amyloid fibrils, and includes disease caused by transthyretin, apolipoprotein AI, gelsolin, lysozyme, cystatin C and amyloid β-protein. Comprehensive descriptions of all the different forms of amyloidosis and the proteins involved are available in textbooks and the scientific literature[1,8,21].

Local amyloid deposition, confined to one organ or tissue, can be clinically silent or can cause serious tissue damage and disease. For example, cerebral amyloid angiopathy in which the vascular amyloid deposits are composed of Aβ protein, is usually a sporadic acquired condition arising for reasons which are not understood in the absence of any other pathology, and is a major cause of cerebral hemorrhage and stroke. There are several very important and common diseases, particularly Alzheimer's disease and type 2 diabetes, in which amyloid deposits are always present but in which the precise mechanisms causing these respective diseases are not yet known. Nevertheless the local deposition of amyloid in the brain and cerebral blood vessels in Alzheimer's disease, and in the pancreatic islets in diabetes is very likely to exacerbate pathology and disease. Accordingly, in one embodiment, the invention relates to treatment of both Alzheimer's disease and type 2 diabetes, indeed to any condition associated with the presence of amyloid deposits in the tissues.

Many forms of transmissible spongiform encephalopathy (prion diseases) are associated with amyloid deposits in the brain, and the present invention therefore relates to all these conditions, including variant Creutzfeldt-Jakob disease in humans, Creutzfeldt-Jakob disease itself, kuru and the various other forms of human prion disease, and also bovine spongiform encephalopathy, chronic wasting disease of mule-deer and elk, and transmissible encephalopathy of mink.

The treatment of animals, including poultry such as chickens, ducks, turkeys and geese, and, preferably, mammals, including humans, as well as dogs, cats, horses, cows, sheep, pigs, guinea pigs, mice and rats is contemplated. In particular, the treatment of humans is preferred.

Accordingly, in one aspect, there is provided SAP-depleting compound in combination with an antibody specific for SAP for use in the treatment of amyloidosis.

Anti-SAP Antibody

References herein to anti-SAP antibodies, SAP-binding antibodies and antibodies specific for SAP are coterminous and refer to antibodies, or binding fragments derived from antibodies, which bind to SAP in a specific manner and substantially do not cross-react with other molecules present in the circulation or the tissues. In particular, the antibodies according to the invention target SAP which is bound to amyloid fibrils in the tissue amyloid deposits.

The SAP molecule is a pentamer composed of five identical non-covalently associated protomers arranged with cyclic pentameric symmetry in a disc-like configuration. On one face of the molecule each protomer has a short α-helix, designated herein as the A face. On the opposite face each protomer has the calcium dependent ligand binding pocket through which SAP recognizes and binds to its ligands, including amyloid fibrils, and designated herein as the B face. There are two calcium atoms in each binding pocket (FIG. 8). In the absence of calcium, human SAP forms stable decameric dimers, probably via A-face to A-face interactions. In the presence of calcium, isolated human SAP rapidly aggregates and precipitates, as a result of molecular lattice formation due to binding of the exposed carboxylate of the Glu167 residue on one SAP molecule by the calcium dependent ligand binding site of another SAP molecule. This auto-aggregation of SAP is inhibited by other ligands to which SAP binds.

An "antibody" as used herein includes but is not limited to, polyclonal, monoclonal, recombinant, chimeric, complementarity determining region (CDR)-grafted, single chain, bi-specific, Fab fragments and fragments produced by a Fab expression library. Such fragments include fragments of whole anti-SAP antibodies which retain their binding activity for SAP, Fv, F(ab'), F(ab')2 fragments, and F(v) antibody fragments as well as fusion proteins and other synthetic proteins which comprise the antigen-binding site of the anti-SAP antibody. Furthermore, the antibodies and fragments thereof may be humanized antibodies, as described in further detail below.

Variable regions and CDRs in an antibody sequence may be identified by aligning the sequences against a database of known variable regions. Methods for identifying these regions are described in, for example, Kontermann and Dubel, eds., *Antibody Engineering*, Springer, New York, N.Y., 2001. Databases of antibody sequences are described in, for example, VBASE2 at www.vbase2.org, as described in Retter et al., *Nucl. Acids Res.*, 33 (Database issue): D671-D674 (2005).

Monoclonal anti-human SAP antibody produced in mouse is commercially available from various sources—such as Sigma-Aldrich, Gillingham, Dorset, UK (Catalogue #A9191); US Biological (catalogue #S1003-3, 1003-4); Acris Antibodies (catalogue #BM225); Kamya Biomedical Co. (catalogue #MC-978); Cell Sciences (catalogue #MON 6006); Abnova Corp. (catalogue #H00000325-MO7). Examples of monoclonal anti-human SAP antibodies include eight distinct monoclonal anti-human SAP IgG antibodies (SAP-1-SAP-7 and NH) generated using standard techniques and tested by immunoradiometric assays (IRMA) for their binding to human SAP (see Example 9 below). Two of these antibodies, SAP-5 and SAP-2, are of the IgG2a isotype while the others are of the IgG1 isotype. Importantly, murine IgG2a is an isotype known to activate mouse complement whereas murine IgG1 antibodies do not and the amyloid clearance mechanism according to the present invention is complement dependent (see Examples 6 and 7, below). The hybridoma that secretes SAP-5 will be deposited. Examples of monoclonal anti-human SAP antibodies also include a set of six distinct monoclonal anti-SAP IgG2a antibodies generated by standard techniques (3H8.H3, 3H8.H6, 3H8.H8, 6H1.G2, 6H1.G3, 6H1.H1, one of which, 6H1.G2 is designated here as Abp1 and was deposited with American Type Culture Collection (ATCC) on Dec. 9, 2008 and assigned accession number 191236

The epitope on human SAP that is recognized and bound by SAP-5 is part of the linear amino acid sequence of human SAP, as shown by the fact that this antibody binds equally well to completely denatured and to native human SAP (Example 9). The present application also shows that SAP-5 binds to a linear amino acid sequence in the large amino terminal fragment of human SAP, residues 1-159, after cleavage of SAP by cyanogen bromide at residue 159M (FIG. 9). Digestion of human SAP with chymotrypsin cleaves SAP immediately after residues 140Y and 144F to give fragments 1-140 and 145-204 with the intermediate small fragment 140-144 being lost. Monoclonal antibody SAP-5 reacts very weakly with the 1-140 fragment but very strongly with the small amount of residual undigested intact SAP protomer, suggesting that the sequence recognized by SAP-5 may include residues 140-159 (FIG. 9). Sequence comparison between human and mouse SAP reveals 3 amino acid differences at residues 139, 143 and 145, consistent with potential immunogenicity of this part of the human SAP sequence in mice in which the monoclonal antibody was produced (FIG. 9). In contrast, antibody Abp1 only binds to native and not to denatured or cleaved human SAP and thus recognises a discontinuous or conformational epitope (Example 9). Native human SAP, a protein composed of 5 identical 204 residue glycosylated protomers each of mass 25,462 Da[7], contains discrete and different epitopes. Two of these epitopes are: (1) a linear (contiguous) amino acid sequence found in the amino terminal 159 residues of the protein, and (2) a conformational epitope present only in the native molecule. Nevertheless, both antibodies described above bind optimally to SAP in its ligand-bound conformation (Example 9), which is essential for an effective anti-human SAP antibody according to the present invention in which the antibody must bind to, and activate complement on, human SAP bound to amyloid deposits in vivo.

Thus, the present invention also relates to antibodies that bind to an epitope of human SAP that is recognized by either SAP-5 or Abp1, including antibodies which bind to the linear amino acid sequence in the amino terminal fragment of human SAP after cleavage of the protein by chymotrypsin and the conformational epitope described above.

The term "monoclonal antibody" refers to an antibody obtained from a single clone of B lymphocyte derived plasma cells producing a homogeneous antibody of a single heavy and light chain class and epitope specificity.

Monoclonal antibodies are typically highly specific, and are directed against a single antigenic site (epitope), in contrast to conventional antibodies within an antiserum induced in a whole animal by immunisation with a particular antigen. Such conventional antibodies are derived from many different clones of B lymphocytes which recognise either the same or different epitopes on the immunising antigen, and are known as polyclonal antibodies. In addition to their very restricted specificity, monoclonal antibodies are readily produced in pure form uncontaminated by other immunoglobulins, whereas isolation of specific antibodies from a polyclonal antiserum requires demanding immunopurification procedures. Monoclonal antibodies may be prepared by the hybridoma method (see Kohler et al., *Nature*, 256:495-7, 1975), or by recombinant DNA methods. The monoclonal antibodies may even be isolated from phage antibody libraries using well known techniques.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)).

In the hybridoma method, a host animal, typically a mouse, is immunized with the desired antigen to induce generation of clones of B lymphocytes that produce or are capable of producing antibodies that will specifically bind to that antigen. Lymphocytes harvested from the immunised animal are then fused in vitro with a continuous line of myeloma cells grown in vitro to form so-called hybridoma cells. These are then selected by growth in a suitable culture medium that permits survival only of fused cells and not the unfused, parental myeloma cells. Examples of myeloma cells include, but are not limited to, human myeloma and mouse-human heteromyeloma cell lines which have been described for the production of human monoclonal antibodies.

The culture medium from the growing hybridoma cells may be assayed for monoclonal antibodies directed against the antigen. The binding specificity of the antibodies produced by the cells may be determined by various methods—such as immunoprecipitation or an in vitro binding assay—such as radioimmunoassay (RIA), enzyme-linked immunosorbent assay (ELISA) or immunoradiometric assay (IRMA).

After hybridoma cells are identified that produce the desired antibodies, the clones may be subcloned by limiting dilution procedures and grown by standard methods. The monoclonal antibodies secreted by the subclones are separated from the culture medium or serum by well-known immunoglobulin purification procedures—such as protein A-Sepharose, gel electrophoresis, dialysis, hydroxylapatite chromatography or affinity chromatography.

Polyclonal antibodies may be raised in animals by multiple subcutaneous, intramuscular or intraperitoneal injections of the relevant antigen and an adjuvant. An improved antibody response may be obtained by conjugating the relevant antigen to a protein that is immunogenic in the species to be immunized. Animals may be immunized against the antigen, immunogenic conjugates, or derivatives by combining, eg., 100 μg or 5 μg of the protein or conjugate (for rabbits or mice, respectively) with suitable adjuvants, including, but not limited to, Freund's complete adjuvant, aluminium hydroxide, Freund's incomplete adjuvant, L-tyrosine, nitrocellulose-absorbed protein, immune-stimulating complexes (ISCOMS, antigen-modified saponin/cholesterol micelles) or MPL-TDM adjuvant (monophosphoryl lipid A, synthetic trehalose dicorynomycolate), for instance, and injecting the solution intradermally at multiple sites. The animals may then be later boosted with ⅕ of the original amount of peptide or conjugate in adjuvant by subcutaneous injection at multiple sites. At 7-14 days post-booster injection, the animals can be bled and the serum is assayed for antibody titre.

The anti-SAP antibodies and fragments also encompass variants of the anti-SAP antibodies and fragments thereof. Variants include peptides and polypeptides comprising one or more amino acid sequence substitutions, deletions, and/or additions that have the same or substantially the same affinity and specificity of epitope binding as the anti-SAP antibody or fragments thereof.

The deletions, insertions or substitutions of amino acid residues may produce a silent change and result in a functionally equivalent substance. Deliberate amino acid substitutions may be made on the basis of similarity in polarity, charge, solubility, hydrophobicity, hydrophilicity, and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
|           |           | I L V |
|           | Polar - uncharged | C S T M |
|           |           | N Q |
|           | Polar - charged | D E |
|           |           | K R |
| AROMATIC  |           | H F W Y |

Homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids—such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ϵ-amino caproic acid, 7-amino heptanoic acid*, L-methionine sulfone, L-norleucine*, L-norvaline*, p-nitro-L-phenylalanine*, L-hydroxyproline, L-thioproline*, methyl derivatives of phenylalanine (Phe) such as 4-methyl-Phe*, pentamethyl-Phe*, L-Phe (4-amino), L-Tyr (methyl)*, L-Phe (4-isopropyl)*, L-Tic (1,2,3,4-tetrahydroisoquinoline-3-carboxyl acid)*, L-diaminopropionic acid and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Thus, variants may include peptides and polypeptides comprising one or more amino acid sequence substitutions, deletions, and/or additions to the anti-SAP antibodies and fragments thereof wherein such substitutions, deletions and/or additions do not cause substantial changes in affinity and specificity of epitope binding. For example, a variant of an anti-SAP antibody or fragment thereof may result from one or more changes to an anti-SAP antibody or fragment thereof, where the changed anti-SAP antibody or fragment thereof has the same or substantially the same affinity and specificity of epitope binding as the starting sequence. Variants may be naturally occurring, such as allelic or splice variants, or may be artificially constructed. Variants may be prepared from the corresponding nucleic acid molecules encoding said variants. Variants of the anti-SAP antibodies or fragments thereof may have changes in light and/or heavy chain amino acid sequences that are naturally occurring or are introduced by in vitro engineering of native sequences using recombinant DNA techniques. Naturally occurring variants include "somatic" variants which are generated in vivo in the corresponding germ line nucleotide sequences during the generation of an antibody response to a foreign antigen.

Variants of SAP binding antibodies and binding fragments may also be prepared by mutagenesis techniques. For example, amino acid changes may be introduced at random throughout an antibody coding region and the resulting variants may be screened for binding affinity for SAP or for another property. Alternatively, amino acid changes may be introduced into selected regions of the anti-SAP antibody, such as in the light and/or heavy chain CDRs, and/or in the framework regions, and the resulting antibodies may be screened for binding to SAP or some other activity. Amino acid changes encompass one or more amino acid substitutions in a CDR, ranging from a single amino acid difference to the introduction of multiple permutations of amino acids within a given CDR. Also encompassed are variants generated by insertion of amino acids to increase the size of a CDR.

Anti-SAP antibodies or fragments thereof may be provided with a modified Fc region where a naturally-occurring Fc region is modified to increase the half-life of the antibody or fragment in a biological environment, for example, the serum half-life or a half-life measured by an in vitro assay.

Variants also include anti-SAP antibodies or fragments thereof comprising a modified Fc region, wherein the modified Fc region comprises at least one amino acid modification relative to a wild-type Fc region. The variant Fc region may be designed, relative to a comparable molecule comprising the wild-type Fc region, so as to bind Fc receptors with a greater or lesser affinity. For example, the SAP binding antibodies and fragments thereof may comprise a modified Fc region. Fc region refers to naturally-occurring or synthetic polypeptides homologous to the IgG C-terminal domain that is produced upon papain digestion of IgG. IgG Fc has a molecular weight of approximately 50 kD. In the antibodies and fragments, an entire Fc region can be used, or only a half-life enhancing portion. In addition, many modifications in amino acid sequence are acceptable, as native activity is not in all cases necessary or desired.

The SAP binding antibodies and fragments thereof also encompass derivatives of the antibodies, fragments and sequences disclosed herein. Derivatives include polypeptides or peptides, or variants, fragments or derivatives thereof, which have been chemically modified. Examples include covalent attachment of one or more polymers—such as water soluble polymers, N-linked, or O-linked carbohydrates, sugars, phosphates, and/or other such molecules. The derivatives are modified in a manner that is different from naturally occurring or starting peptide or polypeptides, either in the type or location of the molecules attached. Derivatives further include deletion of one or more chemical groups which are naturally present on the peptide or polypeptide.

The present invention also encompasses SAP binding antibodies that include two full length heavy chains and two full length light chains. Alternatively, the SAP binding antibodies may be constructs such as single chain antibodies or "mini" antibodies that retain binding activity to SAP. Such constructs may be prepared by methods well known in the art.

Methods for creating recombinant DNA versions of the antigen-binding regions of antibody molecules which bypass the generation of monoclonal antibodies are contemplated for the SAP binding antibodies and fragments thereof. DNA is cloned into a bacterial expression system. One example of such a technique uses a bacteriophage lambda vector system having a leader sequence that causes the expressed Fab protein to migrate to the periplasmic space (between the bacterial cell membrane and the cell wall) or to be secreted. One can rapidly generate and screen great numbers of functional Fab fragments for those which bind SAP. Such SAP binding agents (Fab fragments with specificity for an SAP polypeptide) are specifically encompassed within the SAP binding antibodies and fragments thereof.

The SAP binding antibodies and fragments thereof may be humanized or human engineered antibodies. As used herein, "a humanized antibody", or antigen binding fragment thereof, is a recombinant polypeptide that comprises a portion of an antigen binding site from a non-human antibody and a portion of the framework and/or constant regions of a human antibody. A human engineered antibody or antibody fragment is a non-human (e.g., mouse) antibody that has been engineered by modifying (e.g., deleting, inserting, or substituting) amino acids at specific positions so as to reduce or eliminate any detectable immunogenicity of the modified antibody in a human.

Humanized antibodies include chimeric antibodies and CDR-grafted antibodies. Chimeric antibodies are antibodies that include a non-human antibody variable region linked to a human constant region. Thus, in chimeric antibodies, the variable region is mostly non-human, and the constant region is human. Chimeric antibodies and methods for making them are described in, for example, *Proc. Natl. Acad. Sci. USA*, 81: 6841-6855 (1984). Although, they can be less immunogenic than a mouse monoclonal antibody, administrations of chimeric antibodies have been associated with human immune responses (HAMA) to the non-human portion of the antibodies. Chimeric antibodies can also be produced by splicing the genes from a mouse antibody molecule of appropriate antigen-binding specificity together with genes from a human antibody molecule of appropriate biological activity, such as the ability to activate human complement and mediate antibody dependent cellular cytotoxicity (ADCC). One example is the replacement of a Fc region with that of a different isotype.

CDR-grafted antibodies are antibodies that include the CDRs from a non-human "donor" antibody linked to the framework region from a human "recipient" antibody. Generally, CDR-grafted antibodies include more human antibody sequences than chimeric antibodies because they include both constant region sequences and variable region (framework) sequences from human antibodies. Thus, for example, a CDR-grafted humanized antibody of the invention can comprise a heavy chain that comprises a contiguous amino acid sequence (e.g., about 5 or more, 10 or more, or even 15 or more contiguous amino acid residues) from the framework region of a human antibody (e.g., FR-1, FR-2, or FR-3 of a human antibody) or, optionally, most or all of the entire framework region of a human antibody. CDR-grafted antibodies and methods for making them are described in *Nature*, 321: 522-525 (1986). Methods that can be used to produce humanized antibodies also are described in, for example, U.S. Pat. Nos. 5,721,367 and 6,180,377.

"Veneered antibodies" are non-human or humanized (e.g., chimeric or CDR-grafted antibodies) antibodies that have been engineered to replace certain solvent-exposed amino acid residues so as to reduce their immunogenicity or enhance their function. Veneering of a chimeric antibody may comprise identifying solvent-exposed residues in the non-human framework region of a chimeric antibody and replacing at least one of them with the corresponding surface residues from a human framework region. Veneering can be accomplished by any suitable engineering technique.

Further details on antibodies, humanized antibodies, human engineered antibodies, and methods for their preparation can be found in *Antibody Engineering*, Springer, New York, N.Y., 2001.

Examples of humanized or human engineered antibodies are IgG, IgM, IgE, IgA, and IgD antibodies. The antibodies may be of any class (IgG, IgA, IgM, IgE, IgD, etc.) or isotype and can comprise a kappa or lambda light chain. For example, a human antibody may comprise an IgG heavy chain or defined fragment, such as at least one of isotypes, IgG1, IgG2, IgG3 or IgG4. As a further example, the antibodies or fragments thereof can comprise an IgG1 heavy chain and a kappa or lambda light chain.

The anti-SAP antibodies and fragments thereof may be human antibodies—such as antibodies which bind the SAP polypeptides and are encoded by nucleic acid sequences which may be naturally occurring somatic variants of human germline immunoglobulin nucleic acid sequence, and fragments, synthetic variants, derivatives and fusions thereof. Such antibodies may be produced by any method known in the art, such as through the use of transgenic mammals (such as transgenic mice) in which the native immunoglobulins have been replaced with human V-genes in the mammal chromosome.

Human antibodies to target SAP can also be produced using transgenic animals that have no endogenous immunoglobulin production and are engineered to contain human immunoglobulin loci, as described in WO 98/24893 and WO 91/00906.

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse.

The development of technologies for making repertoires of recombinant human antibody genes, and the display of the encoded antibody fragments on the surface of filamentous bacteriophage, has provided a means for making human antibodies directly. The antibodies produced by phage technology are produced as antigen binding fragments-usually Fv or Fab fragments-in bacteria and thus lack effector functions. Effector functions can be introduced by one of two strategies: the fragments can be engineered either into complete antibodies for expression in mammalian cells, or into bispecific antibody fragments with a second binding site capable of triggering an effector function.

Human antibodies may be generated through the in vitro screening of antibody display libraries (*J. Mol. Biol*. (1991) 227: 381). Various antibody-containing phage display libraries have been described and may be readily prepared. Libraries may contain a diversity of human antibody sequences, such as human Fab, Fv, and scFv fragments, that may be screened against an appropriate target. Phage display libraries may comprise peptides or proteins other than antibodies which may be screened to identify agents capable of selective binding to SAP.

Phage-display processes mimic immune selection through the display of antibody repertoires on the surface of filamentous bacteriophage, and subsequent selection of phage by their binding to an antigen of choice. One such method is described in WO 99/10494. Anti-SAP antibodies can be isolated by screening of a recombinant combinatorial antibody library, preferably a scFv phage display library, prepared using human $V_L$ and $V_H$ cDNAs prepared from mRNA derived from human lymphocytes. Methodologies for preparing and screening such libraries are known in the art. There are commercially available kits for generating phage display libraries.

The antibodies of the invention include "cross-linked" antibodies. The term "cross-linked" as used herein refers to binding of at least two IgG molecules together to form one (or single) molecule. The SAP antibodies may be cross-linked using various linker molecules and optionally the antibodies are cross-linked using an anti-IgG molecule, complement, chemical modification or molecular engineering. Among the various murine Ig isotypes, IgM, IgG2a and IgG2b are known to fix complement.

The antibodies of the invention advantageously comprise "complement fixing" antibodies and fragments thereof (Examples 6 & 7). A complement fixing antibody or fragment thereof is one which having bound to its specific epitopes on the target antigen then activates the complement cascade. In the case of the IgG antibodies required for the present invention such activation takes place predominantly via the classical pathway via C1q although all complement activation is amplified by the feedback loop of the alternative pathway. The key effects of complement in relation to the present invention are then cleavage and binding of C3, the pivotal and most abundant complement component, and the subsequent activation and cleavage of C5. The small split fragments of C3 and C5, respectively C3a and C5a, are potent chemotactic attractants for phagocytic cells of all types, polymorphonuclear granulocytes and mononuclear phagocytes, monocytes and macrophages. The latter group are essential for amyloid clearance according to the present invention (Example 8). The presence on amyloid deposits of bound complement, predominantly C3b and its further breakdown products, C3bi, C3c and C3d, is recognised by the specific receptors on phagocytic cells for such bound complement fragments and thereby opsonises the deposits, that is enhances their phagocytosis and destruction, leading to the desirable and clinically beneficial removal of amyloid which is the purpose of the present invention.

Antibodies of the present invention are specific for SAP and do not recognise or bind to any cell surface to other cellular antigens. They are accordingly free of specific agonistic activity.

Further, antibodies of the invention may optionally comprise dimeric antibodies, as well as multivalent forms of antibodies. Those skilled in the art may construct such dimers or multivalent forms by techniques known in the art and using the anti-SAP antibodies herein.

The antibodies of the invention may also comprise monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross linking. Alternatively, the relevant cysteine residues are substituted with another amino acid residue or are deleted so as to prevent cross linking.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields an F(ab').sub.2 fragment that has two antigen combining sites and is still capable of cross-linking antigen.

The SAP binding antibodies and fragments thereof may comprise one or more portions that do not bind SAP but instead are responsible for other functions, such as circulating half-life, direct cytotoxic effect, detectable labeling, or activation of the recipient's endogenous complement cascade or endogenous cellular cytotoxicity. The antibodies or fragments thereof may comprise all or a portion of the constant region and may be of any isotype, including IgA (e.g., IgA1 or IgA2), IgD, IgE, IgG (e.g. IgG1, IgG2, IgG3 or IgG4), or IgM. In addition to, or instead of, comprising a constant region, antigen-binding compounds of the invention may include an epitope tag, a salvage receptor epitope, a label moiety for diagnostic or purification purposes, or a cytotoxic moiety such as a radionuclide or toxin.

The anti-SAP antibody or fragment thereof may be modified in order to increase its serum half-life, for example, by adding molecules—such as PEG or other water soluble polymers, including polysaccharide polymers to increase the half-life.

The SAP binding antibodies and fragments thereof may be bispecific. For example, bispecific antibodies may resemble single antibodies (or antibody fragments) but have two different antigen binding sites (variable regions). Bispecific antibodies can be produced by various methods—such as chemical techniques, "polydoma" techniques or recombinant DNA techniques. Bispecific antibodies may have binding specificities for at least two different epitopes, at least one of which is an epitope of SAP.

The SAP binding antibodies and fragments may be heteroantibodies. Heteroantibodies are two or more antibodies, or antibody binding fragments (Fab) linked together, each antibody or fragment having a different specificity.

As used herein, the term "antibody fragments" refers to portions of an intact full length antibody—such as an antigen binding or variable region of the intact antibody. Examples of antibody fragments include Fab, Fab', F(ab') and Fv fragments; diabodies; linear antibodies; single-chain antibody molecules (e.g., scFv); multispecific antibody fragments such as bispecific, trispecific, and multispecific antibodies (e.g., diabodies, triabodies, tetrabodies); binding-domain immunoglobulin fusion proteins; camelized antibodies; minibodies; chelating recombinant antibodies; tribodies or bibodies; intrabodies; nanobodies; small modular immunopharmaceuticals (SMIP), V containing antibodies; and any other polypeptides formed from antibody fragments.

In the context of the present invention, the terms anti-SAP antibody and SAP binding antibody encompass SAP binding antibody fragments comprising any part of the heavy or light chain sequences of the full length antibodies, and which bind SAP.

The term "fragments" as used herein refers to fragments capable of binding SAP, for example any of at least 3 contiguous amino acids (e.g., at least 4, 5, 6, 7, 8, 9 or 10 or more contiguous amino acids, for example from a CDR) of the antibody involved in antigen binding, and encompasses Fab, Fab', F(ab')$_2$, and F(v) fragments, or the individual light or heavy chain variable regions or portion thereof. SAP binding fragments include, for example, Fab, Fab', F(ab')$_2$, Fv and scFv. These fragments lack the Fc fragment of an intact antibody, clear more rapidly from the circulation, and can have less non-specific tissue binding than an intact antibody. These fragments can be produced from intact antibodies using well known methods, for example by proteolytic cleavage with enzymes such as papain (to produce Fab fragments) or pepsin (to produce F(ab')$_2$ fragments).

Advantageously, the fragments of the present invention activate complement.

The SAP binding antibodies and fragments also encompass single-chain antibody fragments (scFv) that bind to SAP. An scFv comprises an antibody heavy chain variable region ($V_H$) operably linked to an antibody light chain variable region ($V_L$) wherein the heavy chain variable region and the light chain variable region, together or individually, form a binding site that binds SAP. An scFv may comprise a $V_H$ region at the amino-terminal end and a $V_L$ region at the carboxy-terminal end. Alternatively, scFv may comprise a V region at the amino-terminal end and a $V_H$ region at the carboxy-terminal end. Furthermore, although the two domains of the Fv fragment, $V_L$ and $V_H$, are coded for by separate genes, they can be joined, using recombinant methods, by a synthetic linker that enables them to be made as a single protein chain in which the VL and VH regions pair to form monovalent molecules (known as single chain Fv (scFv). An scFv may optionally further comprise a polypeptide linker between the heavy chain variable region and the light chain variable region.

The SAP binding antibodies and fragments also encompass domain antibody (dAb) fragments as described in *Nature* 341:544-546 (1989) which consist of a $V_H$ domain.

The SAP binding antibodies and fragments also encompass heavy chain antibodies (HCAb). These antibodies can apparently form antigen-binding regions using only heavy chain variable region, in that these functional antibodies are dimers of heavy chains only (referred to as "heavy-chain antibodies" or "HCAbs"). Accordingly, SAP binding antibodies and fragments may be heavy chain antibodies (HCAb) that specifically bind to SAP.

The SAP binding antibodies and fragments also encompass antibodies that are SMIPs or binding domain immunoglobulin fusion proteins specific for SAP protein. These constructs are single-chain polypeptides comprising antigen binding domains fused to immunoglobulin domains necessary to carry out antibody effector functions (see WO03/041600).

The SAP binding antibodies and fragments also encompass diabodies. These are bivalent antibodies in which $V_H$ and $V_L$ domains are expressed on a single polypeptide chain, but using a linker that is too short to allow for pairing between the two domains on the same chain. This forces the domains to pair with complementary domains of another chain and thereby creates two antigen binding sites (see, for example, WO 93/11161). Diabodies can be bispecific or monospecific.

The SAP binding antibodies and fragments thereof also encompass immunoadhesins. One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to SAP.

The SAP binding antibodies and fragments thereof also encompass antibody mimics comprising one or more SAP binding portions built on an organic or molecular scaffold (such as a protein or carbohydrate scaffold). Proteins having relatively defined three-dimensional structures, commonly referred to as protein scaffolds, may be used as reagents for the design of antibody mimics. These scaffolds typically contain one or more regions which are amenable to specific or random sequence variation, and such sequence randomization is often carried out to produce libraries of proteins from which desired products may be selected. For example, an antibody mimic can comprise a chimeric non-immunoglobulin binding polypeptide having an immunoglobulin-like domain containing scaffold having two or more solvent exposed loops containing a different CDR from a parent antibody inserted into each of the loops and exhibiting selective binding activity toward a ligand bound by the parent antibody. Non-immunoglobulin protein scaffolds have been proposed for obtaining proteins with novel binding properties.

Anti-SAP antibodies or antibody fragments thereof typically bind to human SAP with high affinity (e.g., as determined with BIACORE), such as for example with an equilibrium binding dissociation constant ($K_D$) for SAP of about 15 nM or less, 10 nM or less, about 5 nM or less, about 1 nM or less, about 500 pM or less, about 250 pM or less, about 100 pM or less, about 50 pM or less, or about 25 pM or less, about 10 pM or less, about 5 pM or less, about 3 pM or less about 1 pM or less, about 0.75 pM or less, or about 0.5 pM or less.

Suitably, the anti-SAP antibody or antibody fragment thereof does not cross-react with any target other than SAP.

The antibodies and antibody fragments described herein can be prepared by any suitable method. Suitable methods for preparing such antibodies and antibody fragments are known in the art. The antibody or antibody fragment may be isolated or purified to any degree.

As used herein, an "isolated compound" is a compound that has been removed from its natural environment.

"A purified compound" is a compound that has been increased in purity, such that it exists in a form that is more pure than it exists in its natural environment and/or when initially synthesized and/or amplified under laboratory conditions. Purity is a relative term and does not necessarily mean absolute purity.

SAP-Depleting Compound

Compounds of the present invention include those compounds that result in the depletion of circulating SAP.

Such compounds include those which are competitive inhibitors of binding of SAP to amyloid fibrols, as described in European patent application EP 0 915 088, including (R)-1-[6-[(R)-2-Carboxy-pyrrolidin-1-yl]-6-oxo-hexanoyl]pyrrolidine-2-carboxylic acid (CPHPC), however, any of the compounds described therein, or any other compound which depletes circulating SAP can be used in the practice of the present invention.

International Patent Application WO 2004/099173, incorporated herein by reference, also describes palindromic compounds that could also be used in the practice of the present invention.

In a preferred embodiment, the SAP-depleting compound is a D-proline; preferred are D-prolines of the Formula:

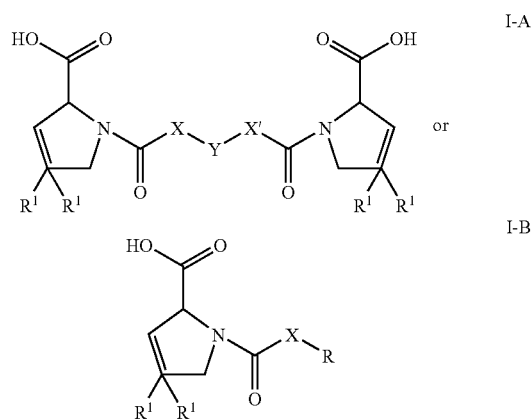

wherein
R is

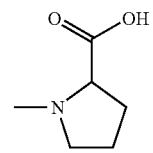

and the group
R¹ is hydrogen or halogen;
X—Y—X' is a linker having at least 4, advantageously at least 5, advantageously at least 6, up to 20 linear or straight-chain carbon atoms, wherein
X is —(CH$_2$)$_n$—; —CH(R$^2$)(CH$_2$)$_n$—; CH$_2$O(CH$_2$)$_n$—; CH$_2$NH—; benzyl, —C(R$^2$)=CH—; —CH$_2$CH(OH)—; or thiazol-2,5-diyl; O;

Y is —S—S—; —(CH)—; —O—; —NH—; —N(R²)—; —CH=CH—; —NHC(O)NH—; —N(R²)C(O)N(R²)—; —N[CH₂C₆H₃(OCH₃)₂]—; —N(CH₂C₆H₅)—; —N(CH₂C₆H₅)C(O)N (CH₂C6H₅)—; —N(alkoxyalkyl)-; N(cycloalkyl-methyl)-; 2,6-pyridyl; 2,5-furanyl; 2,5-thienyl; 1,2-cyclohexyl; 1,3-cyclohexyl; 1,4-cyclohexyl; 1,2-naphthyl; 1,4-naphthyl; 1,5-naphthyl; 1,6-naphthyl; biphenylen; or 1,2-phenylen, 1,3-phenylen and 1,4-phenylen, wherein the phenylen groups are optionally substituted by 1-4 substituents, selected from halogen, lower alkyl, lower alkoxy, hydroxyl, carboxy, —COO-lower alkyl, nitrilo, 5-tetrazol, (2-carboxylic acid pyrrolidin-1-yl)-2-oxo-ethoxy, N-hydroxycarbamimiodyl, 5-oxo[1,2,4oxadiazolyl, 2-oxo [1,2,3,5] oxathiadiazolyl, 5-thioxo[1,2,4]oxadiazolyl and 5-tert-butylsulfanyl-[1,2,4]oxadiazolyl;

X' is —(CH)—; —(CH₂)$_n$CH(R²)—; —(CH₂)$_n$ OCH₂—; —NHCH₂—; benzyl, —CH=C(R²)—; CH(OH)CH₂; or thiazol-2,5-diyl; O;

R² is lower alkyl, lower alkoxy or benzyl and n is 0-3, or a pharmaceutically acceptable salt or mono- or diester thereof. The compound which depletes SAP from the circulation, including the preferred embodiments mentioned above, is referred to hereinafter as an SAP-depleting compound.

In one embodiment, D-proline of formula I-A above can be written as Ligand-linker-Ligand, wherein the X—Y—X' moiety of formal I-A forms the linker. It is within the scope of the present invention that the linker (X—Y—X') can be from 4 to 20 linear carbon atoms in length, including from 4-15 linear carbon atoms, 5-10 linear carbon atoms, and 6-8 linear carbon atoms in length. The linker can be a straight or branched chain, or can optionally form one or more ring structures, with the proviso that at least 4 linear or straight-chain carbon atoms are present in the linker. In one embodiment, at least one of the linear or straight-chain C atoms can be optionally substituted by at least one hetero atom selected from N, O, or S, advantageously O or S, preferably O.

Thus, an "optionally substituted linker" can have one or more substitutions that lead to branching and/or one or more substitutions of carbon atom(s) of the linear or straight-chain carbon atoms of the linker, e.g. the linker can be an ether or a substituted ether.

SAP-CPHPC Complex

The complex of SAP with CPHPC comprises two pentameric SAP molecules cross linked, B face to B face by five CPHPC molecules, and the D-proline head groups at either end of which are bound in the calcium dependent ligand binding pockets of opposite pairs of SAP protomers (FIG. 10). This complex may be covalently cross linked, using the bifunctional cross linker, BS3, to produce a stable complex in which the SAP molecules are fixed in the orientation and with the same stereochemical accessibility to binding by antibodies as SAP deposited on amyloid fibrils in vivo (FIG. 11). Binding of anti-human SAP antibodies to SAP immobilised on a solid surface, such as microtiter plates, can be accurately quantified. Comparison of such binding to SAP immobilised alone and in the stable complex with CPHPC after cross linking with BS3, and in the presence and absence of calcium, provides information about the position and nature of the epitope recognised by each antibody.

Pharmaceutical Compositions

Suitably, the SAP-depleting compound as described herein and the anti-human SAP antibody or fragment thereof described herein will be administered as pharmaceutical compositions comprising therapeutically effective amounts.

As used herein term "therapeutically effective amount" refers to an amount of SAP-depleting compound and the anti-(human) SAP antibody or fragment thereof or as a part of a pharmaceutical composition, that is capable of having any detectable, positive effect on any symptom, aspect, or characteristic of amyloidosis when administered to a patient (e.g., as one or more doses).

As used herein, the term "patient", includes a subject, advantageously an animal subject. Animal subjects of the present invention include mammals, i.e., humans, companion animals including felines and canines, as well as other animals including equines.

The combination of an SAP-depleting compound and the anti-SAP antibody or fragment thereof may be administered separately, simultaneously, sequentially, concurrently or consecutively, or the combination may be presented in the form of one pharmaceutical formulation.

Thus, the present invention also involves the SAP-depleting compound and the anti-SAP antibody or fragment thereof as a combined preparation for simultaneous, separate or sequential use in the therapeutic or prophylactic treatment of amyloidosis.

The pharmaceutical compositions comprising the SAP-depleting compound may be administered separately from the anti-SAP antibodies or fragments thereof, and such separate administrations may be performed at the same point or different points in time, such as for example the same or different days. If the combination of SAP-depleting compound and the anti-SAP antibody or fragment thereof are to be administered sequentially then the SAP-depleting compound is administered first such that the SAP-depleting compound treatment can clear almost all of the circulating SAP. Since this leaves substantial amounts of SAP associated with the amyloid deposits in the tissues the sequential administration of the anti-SAP antibody or fragment thereof enables the localisation and specific binding to the amyloid deposits to promote their rapid and extensive regression. Suitably, the anti-SAP antibody or fragment thereof may be administered 1, 2, 3, 4, 5, 6, 7, 8, 9, 10, 12, 15, 20 or 25 or more days after the treatment(s) with the SAP-depleting compound.

The sequential administration may involve two or more sequential treatments with SAP-depleting compound followed by two or more sequential treatments with the anti-SAP antibody or fragment thereof.

The sequential administration may involve one treatment with SAP-depleting compound followed by one sequential treatment with the anti-SAP antibody or fragment thereof, which is then repeated one or more times.

The sequential/subsequent dose may be an amount that is more than the initial/previous dose or less than the initial/previous dose.

The administration of an initial dose of SAP-depleting compound and/or the anti-SAP antibody or fragment thereof may be followed by the administration of one or more sequential (eg. subsequent) doses of SAP-depleting compound and/or the anti-SAP antibody or fragment thereof, and wherein said one or more sequential doses may be in an amount that is approximately the same or less than the initial dose.

The administration of an initial dose of SAP-depleting compound and/or the anti-SAP antibody or fragment thereof may be followed by the administration of one or more sequential (eg. subsequent) doses, and wherein at least one of the subsequent doses is in an amount that is more than the initial dose.

Accordingly, the administration may use a pre-determined or routine schedule for administration, thereby resulting in a predetermined designated period of time between dose administrations. The schedule may encompass periods of time which are identical or which differ in length, as long as the schedule is predetermined. Any particular combination would be covered by the schedule as long as it is determined ahead of time that the appropriate schedule involves administration on a certain day.

The pharmaceutical compositions may be for human or animal usage in human and veterinary medicine and will typically comprise any one or more of a pharmaceutically acceptable compounds—such as carriers, excipients, diluents, antioxidants, preservatives, colouring, flavouring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants. Acceptable compounds for therapeutic use are well known in the pharmaceutical art, and are described, for example, in Remington's Pharmaceutical Sciences, Mack Publishing Co. (A. R. Gennaro edit. 1985).

The pharmaceutical compositions may include antioxidants—such as ascorbic acid; low molecular weight polypeptides; proteins—such as serum albumin and/or gelatin, hydrophilic polymers—such as polyvinylpyrrolidone; chelating agents—such as EDTA; sugar alcohols—such as mannitol and/or sorbitol; amino acids; monosaccharides, disaccharides, and other carbohydrates; salt-forming counterions—such as sodium; and/or nonionic surfactants—such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, methylparaben, propylparaben, chlorhexidine phenethyl alcohol and sorbic acid. Suitable cosolvents include glycerine and/or propylene glycol.

Suitable complexing agents include caffeine and/or polyvinylpyrrolidone. Suitable surfactants or wetting agents include sorbitan esters and/or polysorbates. The buffers may be conventional buffers such as citrate, acetate, borate, bicarbonate, or Tris-HCl. Acetate buffer may be about pH 4-5.5, and Tris buffer may be about pH 7-8.5. Additional pharmaceutical agents are set forth in *Remington's Pharmaceutical Sciences,* 18th Edition, A. R. Gennaro, ed., Mack Publishing Company, 1990.

The pharmaceutical carrier, excipient or diluent etc. may be selected based upon the intended route of administration and standard pharmaceutical practice.

The composition/formulation requirements may differ dependent on the different delivery system(s).

The composition may be in liquid, lyophilized or freeze-dried form and may include one or more lyoprotectants, excipients, surfactants, high molecular weight structural additives and/or bulking agents. In one embodiment, a lyoprotectant is included, which is a non-reducing sugar—such as sucrose and/or lactose. The amount of lyoprotectant generally included is such that, upon reconstitution, the resulting formulation will typically be isotonic. A surfactant may be included—such as nonionic surfactants and ionic surfactants. Exemplary amounts of surfactant that may be present in the pre-lyophilized formulation are from about 0.001-0.5%. High molecular weight structural additives (e.g. fillers, binders) may be included. Exemplary concentrations of high molecular weight structural additives are from 0.1% to 10% by weight. In other embodiments, a bulking agent (e.g., mannitol, glycine) may be included.

Compositions may be suitable for parenteral administration. Compositions may be suitable for injection or infusion into an animal by any route available to the skilled person, such as intraarticular, subcutaneous, intravenous, intramuscular, intraperitoneal, intracerebral (intraparenchymal), intracerebroventricular, intramuscular, intraocular, intraarterial, intralesional, oral, and inhaled routes. A parenteral formulation typically will be a sterile, pyrogen-free, isotonic aqueous solution, optionally containing pharmaceutically acceptable preservatives.

Pharmaceutical compositions may be formulated for controlled or sustained delivery in a manner that provides local concentration of the product (e.g., bolus, depot effect) sustained release and/or increased stability or half-life in a particular local environment. In certain embodiments such compositions may include a significantly larger amount of the SAP-depleting compound and/or the anti-SAP antibody or fragment thereof in the initial deposit, while the effective amount of antibody or fragment actually released and available at any point in time is in an amount much lower than the initial deposit. The compositions can include the formulation with particulate preparations of polymeric compounds as well as agents such as a biodegradable matrix, injectable microspheres, microcapsular particles, microcapsules, bio-erodible particles beads, liposomes, and implantable delivery devices that provide for the controlled or sustained release of the active agent which then can be delivered as a depot injection.

Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies).

Bioadhesive polymers may also be present use in the compositions. Bioadhesives are synthetic and naturally occurring materials able to adhere to biological substrates for extended time periods. For example, Carbopol and polycarbophil are both synthetic cross-linked derivatives of poly(acrylic acid).

The pharmaceutical composition may be formulated for inhalation, such as for example, as a dry powder. Inhalation solutions also can be formulated in a liquefied propellant for aerosol delivery. In yet another formulation, solutions may be nebulized. Additional pharmaceutical composition for pulmonary administration include, those described, for example, in PCT Application Publication WO 94/20069, which discloses pulmonary delivery of chemically modified proteins. For pulmonary delivery, the particle size should be suitable for delivery to the distal lung. For example, the particle size can be from 1 μm to 5 μm; however, larger particles may be used, for example, if each particle is fairly porous.

Another preparation can involve a mixture with non-toxic excipients which are suitable for the manufacture of tablets. By dissolving the tablets in sterile water, or another appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Certain formulations may be administered orally. Formulations administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of a selective binding agent. Diluents, flavourings, low melting point waxes, vegetable oils, lubricants, suspending agents, tablet disintegrating agents, and binders also can be employed.

The pharmaceutical compositions used in the invention may comprise a therapeutically effective amount or a prophylactically effective amount of the SAP-depleting compound and/or the anti-SAP antibody or fragment thereof.

"A therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects are outweighed by the therapeutically beneficial effects.

"A prophylactically effective amount" refers to an amount effective, at dosages and for periods of time necessary, to achieve the desired prophylactic result.

A therapeutically or prophylactically effective amount of the pharmaceutical composition will depend, for example, upon the therapeutic objectives—such as the indication for which the composition is being used, the route of administration, and the condition of the subject. Pharmaceutical compositions are administered in a therapeutically or prophylactically effective amount to treat amyloidosis. A "therapeutically or prophylactically effective amount" is that amount which can treat or prevent one or more symptoms of amyloidosis in a subject.

The pharmaceutical composition described herein may also be used in combination with conventional treatments for amyloidosis.

Pharmaceutical Salt

The SAP-depleting compound may be administered in the form of a pharmaceutically acceptable salt.

Pharmaceutically-acceptable salts are well known to those skilled in the art, and for example, include those mentioned by Berge et al, in *J. Pharm. Sci.*, 66, 1-19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate and p-toluenesulphonate salts.

When one or more acidic moieties are present, suitable pharmaceutically acceptable base addition salts can be formed from bases which form non-toxic salts and include the aluminium, calcium, lithium, magnesium, potassium, sodium, zinc, and pharmaceutically-active amines such as diethanolamine, salts.

A pharmaceutically acceptable salt may be readily prepared by mixing together solutions of the SAP-depleting compound and the desired acid or base, as appropriate. The salt may precipitate from solution and be collected by filtration or may be recovered by evaporation of the solvent.

Administration

The components may be administered alone but will generally be administered as a pharmaceutical composition—e.g. when the components are as an admixture with a suitable pharmaceutical excipient, diluent or carrier selected with regard to the intended route of administration and standard pharmaceutical practice.

For example, the components can be administered in the form of tablets, capsules, ovules, elixirs, solutions or suspensions, which may contain flavouring or colouring agents, for immediate-, delayed-, modified-, sustained-, pulsed- or controlled-release applications.

If the pharmaceutical is a tablet, then the tablet may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The routes for administration (delivery) may include, but are not limited to, one or more of oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural and sublingual.

In one specific embodiment, the mode of administration is intravenous infusion.

Dose Levels

Suitable and/or preferred pharmaceutical formulations can be determined in view of the present disclosure and general knowledge of formulation technology, depending upon the intended route of administration, delivery format, and desired dosage.

Typically, a physician will determine the actual dosage which will be most suitable for an individual subject.

The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. For example, the SAP-depleting compound may be administered at a dose of between 2 mg/kg and 0.1 mg/kg, depending on its activity.

The anti-SAP antibody or fragment thereof may be administered as a fixed dose, independent of a dose per subject weight ratio, or at an appropriate dose in mg/kg body weight with an approximate maximum of 200 mg/kg. The antibody or fragment thereof may be administered to a 70 kg individual in one or more separate, simultaneous or sequential doses of 14,000 mg or less of antibody or fragment thereof, 13,000 mg or less of antibody or fragment thereof, 12,000 mg or less of antibody or fragment thereof, 11,000 mg or less of antibody or fragment thereof, 10,000 mg or less of antibody or fragment thereof, 9000 mg or less of antibody or fragment thereof, 8000 mg or less of antibody or fragment thereof, 7000 mg or less of antibody or fragment thereof, 6000 mg or less of antibody or fragment thereof, 5000 mg or less of antibody or fragment thereof, 4500 mg or less of antibody or fragment thereof, 4000 mg or less of antibody or fragment thereof, 3700 mg or less of antibody or fragment thereof, 3500 mg or less of antibody or fragment thereof, mg or less of antibody or fragment thereof, 3200 mg or less of antibody or fragment thereof, 3000 mg or less of antibody or fragment thereof, 2700 mg or less of antibody or fragment thereof, 2500 mg or less of antibody or fragment thereof, 2200 mg or less of antibody or fragment thereof, or 2100 mg or less of antibody or fragment thereof, 1700 mg or less of antibody or fragment thereof, 1500 mg or less of antibody or fragment thereof, 1200 mg or less of antibody or fragment thereof, or 1100 mg or less of antibody or fragment thereof, 1000 mg or less of antibody or fragment thereof, 700 mg or less of antibody or fragment thereof, 500 mg or less of antibody or fragment thereof, 200 mg or less of antibody or fragment thereof, or 100 mg or less of antibody or fragment thereof. In another embodiment, the antibody or fragment is administered in one or more doses of at least 20 mg of antibody or fragment thereof. Since the total protein concentration in human plasma is 70,000 mg/l, and standard blood transfusion or plasma or albumin infusions routinely deliver tens or even hundreds of grams of protein intravenously, administration of the maximal doses of anti-SAP antibody are safe and acceptable.

The SAP-depleting compound may be administered as a fixed dose, independent of a dose per subject weight ratio. The SAP-depleting compound may be administered in one or more separate, simultaneous or sequential parenteral doses of 100 mg or less, of 50 mg or less, 25 mg or less, or 10 mg or less. Alternatively, the SAP-depleting compound may be administered in a dose per subject weight ratio as easily determined by one of skill in the art.

Formulation

The component(s) may be formulated into a pharmaceutical composition, such as by mixing with one or more of a suitable carrier, diluent or excipient, by using techniques that are known in the art.

Expression

A wide variety of expression systems are available for the production of anti-SAP antibodies and antibody fragments including Fab fragments, scFv, and V s. For example, expression systems of both prokaryotic and eukaryotic origin may be used for the large-scale production of antibody fragments and antibody fusion proteins.

The gram-negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus *Bacillus* are very suitable as heterologous hosts because of their capability to secrete proteins into the culture medium. Other bacteria suitable as hosts are those from the genera *Streptomyces* and *Pseudomonas*.

Depending on the nature of the polynucleotide encoding the polypeptide, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Examples of suitable expression hosts within the scope of the present invention are fungi such as *Aspergillus* species (such as those described in EP-A-0184438 and EP-A-0284603) and *Trichoderma* species; bacteria such as *Bacillus* species (such as those described in EP-A-0134048 and EP-A-0253455), *Streptomyces species* and *Pseudomonas* species; and yeasts such as *Kluyveromyces* species (such as those described in EP-A-0096430 and EP-A-0301670) and *Saccharomyces* species.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products.

Particularly advantageous are expression systems that permit the secretion of large amounts of antibody fragments into the culture medium.

Kit

In another embodiment of the invention, an article of manufacture, or "kit", containing materials useful for the treatment of the amyloidosis is provided.

Suitably, the kit is formulated for the separate or sequential administration of the D-proline and the anti-SAP antibody or a fragment thereof.

In one embodiment, the kit comprises a container comprising the SAP-depleting compound and the anti-SAP antibody or fragment thereof. In another embodiment, the kit comprises a first container comprising the SAP-depleting compound and a second container comprising the anti-SAP antibody or fragment thereof.

Suitably, the SAP-depleting compound and the anti-SAP antibody or fragment thereof are present in therapeutically or prophylactically effective amounts for the treatment and/or prevention of amyloidosis.

Suitable containers include, for example, bottles, vials, syringes, blister pack, etc. The container may be formed from a variety of materials such as glass or plastic.

The container holds the SAP-depleting compound or a pharmaceutical formulation thereof and/or the anti-SAP antibody or a fragment thereof, in an amount effective for treating amyloidosis, and may have a sterile access port (for example, the container may be an intravenous solution bag or a vial having a stopper pierceable by a hypodermic injection needle).

The kit may further comprise a label or package insert on or associated with the container. The label or package insert may indicate that the composition(s) is used for treating amyloidosis.

Alternatively, or additionally, the kit may further comprise an additional container comprising a pharmaceutically acceptable buffer, such as bacteriostatic water for injection, phosphate-buffered saline, Ringer's solution and dextrose solution. It may further include other materials desirable from a commercial and user standpoint, including other buffers, diluents, filters, needles, and syringes.

The kit may further comprise directions for the administration of the SAP-depleting compound and the anti-SAP antibody or fragment thereof for treating or preventing amyloidosis. For example, if the kit comprises a first composition comprising SAP-depleting compound and a second composition comprising the anti-SAP antibody, the kit may further comprise directions for the simultaneous, sequential or separate administration of the first and second pharmaceutical compositions to a subject in need thereof.

In another embodiment, the kits may be suitable for the delivery of solid oral forms of the compositions—such as tablets or capsules. Such a kit includes, for example, a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

In certain other embodiments wherein the kit comprises a pharmaceutical formulation of the SAP-depleting compound and a second formulation comprising the anti-SAP antibody or a fragment thereof, the kit may comprise a separate container for containing the separate formulations, such as a divided bottle or a divided foil packet; however, the separate compositions may also be contained within a single, undivided container. Typically, the kit comprises directions for the administration of the separate components. This kit form is particularly advantageous when the separate components are administered in different dosage forms (e.g., oral and parenteral), are administered at different dosage intervals, or when titration of the individual components of the combination is desired by the prescribing physician.

Assay Method

In a further aspect, the present invention provides an assay method for identifying one or more agents that can be used in combination with an SAP-depleting compound as described herein for the treatment of amyloidosis, in particular, for the essentially complete clearance of the amyloid deposits.

The agent may be an organic compound or other chemical. The agent may be a compound, which is obtainable from or produced by any suitable source, whether natural or artificial. The agent may be an amino acid molecule, a polypeptide, or a chemical derivative thereof, or a combination thereof. The agent may even be a polynucleotide molecule—which may be a sense or an anti-sense molecule, or an antibody, for example, a polyclonal antibody, a monoclonal antibody or a monoclonal humanized antibody.

In one embodiment, the agent is an antibody—such as an antibody that is derived or derivable from an anti-SAP antibody.

The agent may be prepared by chemical synthesis techniques.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

The invention will now be further described by way of Examples, which are meant to serve to assist one of ordinary skill in the art in carrying out the invention and are not intended in any way to limit the scope of the invention.

EXAMPLES

Example 1

Clearance of Systemic Amyloid Deposits in Transgenic Mice Expressing Human SAP

In the present study AA amyloidosis was induced in mice by amyloid enhancing factor injection followed by repeated casein injections to elicit persistent acute inflammation and thus sufficiently sustained increase in SAA production to promote AA amyloid deposition in all animals. A unique strain of pure line C57BL/6 animals was used in which the mouse SAP gene has been deleted[13] and a human SAP transgene has been introduced[14,15]. They therefore do not express any mouse SAP but do express human SAP and at concentrations significantly greater than those seen in man. We confirmed that all the mice had developed abundant systemic amyloid deposits by demonstrating greatly increased whole body retention of a radiolabelled human SAP tracer compared to untreated control mice with no amyloid. We then treated three very closely matched groups as follows:

Group 1,
(R)-1-[6-[(R)-2-Carboxy-pyrrolidin-1-yl]-6-oxo-hexanoyl]pyrrolidine-2-carboxylic acid (CPHPC), the SAP depleting drug[16,17], and a single dose of sheep anti-human SAP antibody;

Group 2, CPHPC and control sheep IgG from an unrelated antiserum;

Group 3, no treatment.

These control groups are essential to provide comparison with the known spontaneous regression of the amyloid deposits when inflammation ceases. The groups also need to be sufficiently large to compensate for the different rates of amyloid regression in different individual mice, even in these inbred pure line animals. Similarly the experiment cannot be conducted whilst amyloid induction is continuing because of the variable rates at which amyloid deposition occurs. In a preliminary experiment on groups of 15 mice each, conducted according to the same protocol and with the same reagents as described here, we obtained the same result as we show below. The present experiment was then performed with larger numbers in each group to confirm that the observed effect was reproducible and not due to a chance occurrence of accelerated amyloid regression in one of the groups unrelated to the treatment given.

In the human SAP transgenic mice, human SAP is present in both the circulation and the amyloid deposits. The drug CPHPC is specifically bound by human SAP in a complex composed of two native pentameric SAP molecules and 5 CPHPC molecules[16]. This complex is recognised as abnormal by the liver and is very rapidly taken up by the hepatocytes and degraded, thus efficiently clearing SAP from the circulation[16]. Plasma SAP concentrations remain very low for as long as the drug is administered[16]. CPHPC is extremely well tolerated and neither the drug itself nor the SAP depletion it produces have caused any adverse effects[16] (and Gillmore, "Sustained Pharmacological Knockout of Serum Amyloid P Component in Patients with Systemic Amyloidosis", submitted for publication). There is evidence of clinical benefit from CPHPC treatment in human systemic amyloidosis patients, especially with respect to preservation of renal function in individuals with predominantly renal amyloidosis (Gillmore, submitted for publication). Despite these promising observations, swift and optimal therapeutic efficacy capable of preserving organ function and prolonging life in patients with systemic amyloidosis will require substantial or complete clearance of the amyloid deposits. As we demonstrate here, this can now be achieved according to the present invention by treatment with a combination of CPHPC and anti-human SAP antibodies.

CPHPC treatment clears almost all the circulating human SAP but leaves substantial amounts of SAP associated with the amyloid deposits in the tissues (unpublished observations). The greatest depletion of SAP from amyloid deposits which we have observed in human patients is about 90% after months of continuous CPHPC administration. Intravenous infusion of monospecific antibodies against human SAP into patients whose circulating SAP has been depleted enables the antibodies to locate and bind specifically to the amyloid deposits and promote their rapid and extensive regression, with corresponding clinical benefit. We show here the efficacy of this procedure in the human SAP transgenic mouse model of AA amyloidosis.

Experimental Protocol and Methods

Systemic AA amyloidosis was induced in adult male (n=61) and female (n=32) pure line C57BL/6 mice with the mouse SAP gene deleted and which were transgenic for human SAP[15]. Each mouse received a single dose of amyloid enhancing factor[9] by intravenous injection followed 4 days later by 10 daily subcutaneous injections of 10% w/v casein in solution in 0.1M NaHCO$_3$ administered over a 12 day period[13]. Seven days after the last casein injection, KI was introduced into the drinking water of all mice and 3 days later each mouse received an intravenous injection of a standard dose of $^{125}$I-labelled human SAP[6,18]. Four adult male and four female mice from the same colony but which had not received any other treatment were also given KI and $^{125}$I-SAP as controls. All mice underwent whole body counting 24, 48, 72 96 and 168 h after the tracer injection to determine retention of radioactivity as an index of whole body amyloid load. There was consistently more retention in all the treated mice compared to the controls at all time points, indicating that they all had substantial systemic amyloidosis deposits[18]. The mice were then allocated to three closely matched groups with as close as possible to the same total numbers and sex distribution in each group. Ten days after the $^{125}$I-SAP injection groups one and two were started on CPHPC in their drinking water at 1 mg/ml and continued on that treatment until the end of the experiment. Group three received no treatment at this or any later stage of the study. Five days after starting the CPHPC each animal in group one received an intraperitoneal injection comprising 1 ml of the whole IgG fraction of monospecific sheep anti-human SAP antiserum at 50 mg/ml containing 7 mg/ml of specific antibody in solution in phosphate buffered physiological saline. The antiserum was raised by immunisation of sheep with 100% pure human SAP. At the same time all animals in group 2 received an intraperitoneal injection comprising 1 ml of the whole IgG fraction of monospecific sheep anti-human oncostatin M receptor antiserum at 50 mg/ml in solution in phosphate buffered physiological saline. This antiserum, used here as a control for the anti-SAP reagent, showed no reactivity with human SAP, with mouse plasma or with normal mouse tissues by standard immunochemical and immunohistochemical tests. Twenty eight days after the intraperitoneal injections all mice were killed by bleeding out under terminal anaesthesia and the liver and spleen from each were removed. Each organ was weighed and then divided into three portions, one of which was also weighed and used for extraction of SAP, while the second portion was snap frozen for subsequent immunohistochemical and cytochemical analysis without fixation, and the last part was fixed in buffered formalin for routine histology and estimation of amyloid by Congo red staining[19]. All mice were weighed at the time of assignment to the groups after induction of amyloidosis but before administration of $^{125}$I-SAP. They were all weighed again before being killed at the end of the experiment. All mice were bled four times: (1) immediately before groups two and three were started on CPHPC; (2) the day before injection of IgG preparations in groups two and three; (3) 14 days after the IgG injections; (4) at the time of killing. Sections of spleen and liver of all animals stained with Congo red were independently examined by three different expert observers blinded to the treatment each mouse had received and scored for the amount of amyloid present as previously reported. The scores of $10^0$-$10^4$ represent an approximately log base 10 ranking scale from $10^0$, corresponding to one or two tiny specks of amyloidosis among several sections of a particular organ, to $10^4$ corresponding to abundant widespread deposits comprising about 10,000 times more amyloid[13]. There was almost 100% concordance between the scores of the different observers, and the scores of the most experienced observer were therefore used for the present analysis. Concentrations of human SAP in the sera and organ extracts of organs were measured by electroimmunoassay[5].

The time line of the protocol is summarised here:
Day Procedure
−41 Inject AEF i.v. in all mice
−36 to −31 Daily casein injection s.c. in all mice
−29 to −24 Daily casein injection s.c. in all mice
−20 Weigh all mice
−17 Start KI in drinking water for all mice
−15 Inject $^{125}$I-SAP i.v. in all mice
−13 to −10
and −7 Whole body counting of all mice each day
−5 Bleed all for pre-treatment sample
−4 Start CPHPC 1 mg/ml in drinking water for groups 1 & 2; no treatment for group 3
−1 Bleed for post CPHPC pre-antibody treatment sample
0 Inject sheep IgG anti-human SAP antibody group 1
  Inject control sheep IgG group 2
  No treatment group 3
14 Bleed all
23 Weigh all
28 Bleed out and kill all mice, harvest organs Results Body weight and survival. Body weight was not significantly different between the groups. Mean (SD) weights in grams at day −20, that is after amyloid induction and before tracer injection, were:
group 1, 28.0 (2.7)
group 2, 27.7 (3.2)
group 3, 27.3 (3.1).
Mean (SD) weights in grams at day 23, just before the end of the study were
group 1, 28.5 (2.8)
group 2, 28.4 (3.6)
group 3, 27.8 (3.3).

No animals died during the treatment phase of the experiment. Coupled with the constant body weights it is clear that administration of CPHPC and anti-SAP antibody had no significant adverse clinical effects.

Human SAP values. Serum concentrations of human SAP were the same in all groups at the first bleed taken after induction of amyloidosis and before any other treatment, with significantly higher values among the female than the male mice (Table 1), as we have previously observed in this strain. At the second bleed, taken 4 days after CPHPC treatment had been started in groups one and two, and before administration of anti-SAP antibody or control sheep IgG, there was greater than 90% depletion of circulating human SAP (Table 1) as we have previously reported[16,17]. Estimates of human SAP concentration were not possible in sera from group one and two animals at days 14 and 28 after injection of sheep anti-SAP antibody or control IgG because of interference with the assay by persistence of these reagents in the circulation. In group three, which received no other treatment, human SAP values were unchanged at day 14 but were significantly lower at day 28 (Table 1), possibly due to damage to the liver by the amyloidosis.

The quantities of human SAP present in the spleens removed at the end of the experiment are shown in Table 3. SAP, including the transgenic human SAP in these mice, is produced in the liver. Interpretation of the results of assay of human SAP in the livers at the end of the experiment is therefore complicated by the fact that some SAP is present as a result of its synthesis by hepatocytes and not just due the binding of circulating SAP to amyloid deposits within the liver, if these are present. Also the females have consistently significantly higher circulating (Table 1) and liver concentrations of human SAP than males (Table 3). Nevertheless, the human SAP content of the livers in the different groups ranked in the same order as the unequivocal human SAP spleen content results.

TABLE 1

Human SAP concentrations in serum [mean (SD) mg/l]

| | males | | | females | | |
|---|---|---|---|---|---|---|
| group | 1 (n = 21) | 2 (n = 20) | 3 (n = 20) | 1 (n = 10) | 2 (n = 10) | 3 (n = 12) |
| treatment | CPHPC + anti-SAP | CPHPC | none | CPHPC + anti-SAP | CPHPC | none |
| pre-bleed day −2 | 37.1 (14.1) | 35.1 (7.9) | 35.8 (12.0) | 72.0 (14.3) | 82.6 (20.2) | 78.2 (21.3) |
| post CPHPC before antibody day 0 | 2.6 (2.5) | 2.9 (1.3) | 35.4 (14.6) | 3.1 (1.9) | 4.0 (1.4) | 74.3 (17.3) |
| post antibody day 14 | NI | trace | 33.2 (11.1) | NI | trace | 67.9 (20.9) |
| post antibody day 28 | NI | trace | *24.0 (6.4) | NI | trace | **54.0 (12.6) |

NI, not interpretable due to persistence of anti-SAP antibody in serum; trace, very low concentration but not quantifiable due to interference by persistence of sheep IgG in serum.
*Significantly lower than previous bleeds, P = 0.0047 by ANOVA.
**Significantly lower than previous bleeds, P = 0.0131 by ANOVA.

TABLE 2

Human SAP content of spleen at end of experiment (µg/whole organ)

| | males & females | | |
|---|---|---|---|
| group | 1 (n = 31) | 2 (n = 30) | 3 (n = 32) |
| treatment | CPHPC + anti-SAP | CPHPC + control IgG | none |
| median | 0 | 15 | 69 |
| IQ range | 0-0 | 1-18 | 38-113 |
| range | 0-4 | 0-35 | 3-304 |

SAP is not expressed in the spleen and there was no difference between the males and females with respect to either the quantity of spleen amyloid or the amount of human SAP within any of the three groups. SAP content of the spleens is therefore shown here for the whole of each group. Statistical significance of differences between groups (Mann Whitney tests): group 1 vs group 2, P=0.0000; group 1 vs group 3, P=0.0000; group 2 vs group 3, P=0.0000.

TABLE 3

Human SAP content of liver at end of experiment (µg/whole organ)

| | males | | | females | | |
|---|---|---|---|---|---|---|
| group | 1 (n = 20) | 2 (n = 20) | 3 (n = 20) | 1 (n = 10*) | 2 (n = 10) | 3 (n-12) |
| treatment | CPHPC + anti-SAP | CPHPC + control IgG | none | CPHPC + anti-SAP | CPHPC + control IgG | none |
| median | 0 | 59 | 82 | 58 | 78 | 142 |
| IQ range | 0-0 | 42-75 | 56-117 | 40-76 | 60-112 | 76-289 |
| range | 0-56 | 0-100 | 7-150 | 24-87 | 52-148 | 35-735 |

*Sample from one mouse was not available for assay. Statistical significance (Mann Whitney tests) of differences between groups: male group 1 vs group 2 or group 3, P = 0.000; group 2 vs group 3, P = 0.0337; female group 1 vs group 2, P = 0.0413; group 1 vs group 3, P = 0.0069; group 2 vs group 3, P = 0.0698

Amyloid load. The whole body amyloid load was the same in the three groups after amyloid induction and before starting the different treatments. At 72 h after injection of the $^{125}$I-SAP tracer the whole body retention of radioactivity was just 10-11% of the injected dose in each of the 8 non-amyloidotic controls. Among the amyloidotic mice the mean (SD) retention was:
group 1, 57.1% (21.6)
group 2, 44.0% (19.5)
group 3, 50.1% (21.5).

These differences were not significant, P=0.054 by one way ANOVA.

Figure 1:
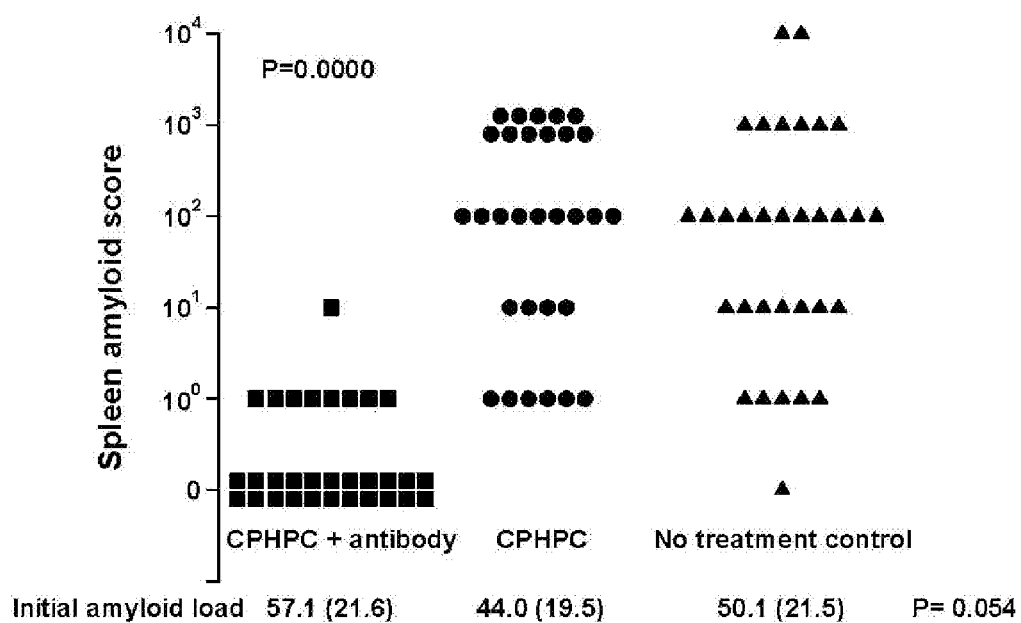
FIG. 1. Amyloid deposits in the spleens of mice after treatment.

At the end of the experiment, the histological assessment of amyloid in the spleen and liver showed highly significant differences between the groups, P=0.0000 by Kruskal-Wallis non-parametric analysis of variance. There was dramatically less amyloid in group 1 (CPHPC plus anti-SAP) than the other two groups but no difference between groups 2 (CPHPC alone) and 3 (no treatment control) (FIGS. 1 and 2). Among 31 mice in group 1 no amyloid was detected in 23 and the remaining 8 had only occasional microscopic specks. In contrast there was no animal among the 62 individuals in the two control groups not receiving anti-SAP which had no amyloid at all. This difference was highly significant by Fisher's exact test, P<0.0001.

|  | Amyloid present | Amyloid absent |
| --- | --- | --- |
| Group 1: CPHPC + anti-SAP | 8 | 23 |
| Group 2: CPHPC + control IgG | 30 | 0 |
| Group 3: No treatment | 32 | 0 |

Among the 62 control mice, only 12 had trace or small amounts of amyloid, the deposits in all the rest being moderate or heavy. Typical examples of the histochemical staining for amyloid corresponding to each of the ranking scores are shown in FIG. 3.

Histological appearances. Haematoxylin and eosin stained sections of all spleen and liver tissues were examined 'blind' to the groups and treatments by Professor A P Dhillon, Professor of Histopathology at University College London. Apart from the amyloid deposits present in groups two and three, and absent in group one, there were modest changes consistent with chronic inflammation in many, though not all, of the tissues and these were not different between the groups.

Discussion

The mice were all killed for estimation of their amyloid load at 60 days after the last casein injection and 28 days after treatment of the test group with anti-SAP antibodies. All mice had substantial amyloid deposits before anti-SAP or control treatments, as demonstrated by $^{125}$I-SAP retention measured 10 days after the last casein injection. There was no significant difference between the groups and there was, as expected, some spontaneous regression of amyloid deposits in a few control mice by the end of the study. However there was no single mouse among the 62 control animals in groups two and three which had no amyloid at all. In contrast 23 of the 31 mice which received anti-SAP antibody as well as CPHPC had no detectable amyloid in their spleen or liver. The only amyloid deposits found in any anti-SAP treated animals were a few microscopic specks, orders of magnitude less than the major deposits present in 50 out of 62 mice which did not receive anti-SAP. It is unequivocally clear that the anti-SAP treatment was responsible for this remarkable clearance of the amyloid deposits in group one, since mice receiving CPHPC and control sheep IgG fraction from an unrelated antiserum (group two) had abundant amyloid indistinguishable in amount from the group three controls who received no treatment at all.

The results from histochemical analysis by Congo red staining were confirmed by estimation of the human SAP content of the spleens and livers. There was no detectable human SAP in the spleens of 29 of the 31 mice in group one and only trace amounts in the remaining two animals. The group three control animals had substantial quantities of human SAP present, corresponding to their heavy amyloid load, and the group two mice had about a quarter of the human SAP content, despite having the same amyloid load, since they had received CPHPC continuously for 33 days before being killed. Human SAP concentrations were reduced by >90% in the sera of all the mice receiving CPHPC in both groups one and two, compared to the control group three. This result demonstrates the capacity of CPHPC to deplete human SAP from the circulation whilst substantial amounts of human SAP remain in the amyloid deposits to provide the target for the therapeutic effect of the anti-SAP antibodies. The combination of CPHPC and anti-SAP antibody is thus essential for the present invention: the small molecule drug clears the plasma and extravascular fluid compartments of human SAP so that the subsequently administered anti-SAP antibody can reach the SAP specifically located in the amyloid deposits and there effect its crucial function of triggering regression and clearance of the amyloid fibrils.

CONCLUSION

Combination treatment of individuals with established systemic amyloid deposits using CPHPC and anti-SAP antibodies safely and effectively causes the rapid and essentially complete clearance of the deposits. This has never previously been achieved in any patient or animal model or by any other method. The invention will be applicable to all forms of acquired and hereditary systemic and local amyloidosis, and also to all other diseases which are associated with amyloid deposits, including Alzheimer's disease and type 2 diabetes.

Example 2

Treatment of a Patient with Systemic Amyloidosis Using CPHPC and Anti-SAP Antibody A patient suffering from systemic amyloidosis is diagnosed by clinical examination and routine investigations leading to suspicion of amyloidosis, followed by specific confirmation by expert histochemical examination of biopsies of affected tissues. Radiolabelled SAP scintigraphy is performed in the UK NHS National Amyloidosis Centre at the Centre for Amyloidosis and Acute Phase Proteins in the Department of Medicine of University College London at the Royal Free Hospital. The tissue examination identifies the particular type of amyloid present and the scan, coupled with echocardiographic examination of the heart, shows where the amyloid is present and quantifies its extent. Routine clinical investigations of organ function establish the extent and severity of tissue and organ damage caused by the amyloid deposits, as well as the presence and severity of any underlying primary disease which may have led to amyloid deposition.

Conventionally, the two essential first steps in treatment of such a patient consist of: (1) maintenance of organ function by all possible means, including drug therapy as appropriate and organ replacement if necessary comprising renal dialysis and organ transplantation, and (2) deployment of whatever therapy may be available to reduce the abundance of the precursor protein which is forming the amyloid fibrils. The latter may be very difficult to achieve and is sometimes impossible, so that organ damage progresses to organ failure, serious morbidity and usually leads to death.

In accordance with the present invention, in this instance the patient is treated to arrest amyloid deposition and to clear away existing established amyloid deposits from the tissues, leading to clinical benefit.

The patient is treated with the SAP depleting drug, CPHPC, administered by bolus intravenous injection of a dose of 100 mg. The following day a blood sample is taken. This confirms by specific immunoassay that the SAP concentration in the serum has been reduced by 90%. An intravenous infusion of anti-SAP antibody is then commenced and over a period of several hours a dose of 1000 mg of antibody is administered sufficient to bind to SAP within the amyloid deposits throughout the body. CPHPC is administered parenterally twice daily for the next two weeks, to ensure that plasma SAP values remain suppressed. All aspects of the patient's clinical state and organ function are monitored closely on a daily basis throughout, and improvements in organ function are detected within days after the antibody infusion. At one month after the treatment, when the CPHPC has been washed out of the body and the anti-SAP antibody has been catabolised, the patient undergoes repeat SAP scintigraphy to estimate the presence and extent of any residual amyloid deposits. Thereafter CPHPC treatment is recommenced giving 0.5 mg/kg twice daily by subcutaneous injection to ensure that as little SAP as possible reaccumulates on any residual amyloid in the tissues. SAP scintigraphy is then repeated 3 monthly to monitor continuing regression of amyloid, with discontinuation of CPHPC one week before each scan and its reinstitution immediately afterwards. After the patient is considered to be free of amyloid deposits, CPHPC administration is stopped, but monitoring is continued by SAP scintigraphy to detect any further abnormal deposition of amyloid. The patient remains disease free during the observation period, but if amyloid deposits recur the treatment with CPHPC and anti-SAP is repeated as required to clear and maintain clearance of amyloid.

Example 3

Effect of Different Doses of Anti-SAP Antibody on Amyloid Clearance

Experimental Protocol and Methods

In an experiment using the same protocol and reagents as described in Example 1 above, different groups of 5 mice each received the following doses of the same IgG fraction of sheep anti-human SAP antiserum as in Example 1: 50 mg (same dose as in Example 1); 10 mg; 2 mg; 0.4 mg; none. The quantity of anti-SAP antibody in these doses was 7 mg, 1.4 mg, 0.28, 0.056 mg and zero respectively.

Results

In the two groups receiving the highest doses of anti-SAP antibody essentially all the amyloid deposits in the spleen and liver were cleared. In none of the other antibody treated groups was there any reduction in amyloid deposits and there was no difference from the control group which received no antibody.

Discussion

The minimal effective dose of this particular sheep polyclonal anti-SAP antibody administered in a single dose in the protocol described in Example 1 was greater than 0.28 mg, and a dose of 1.4 mg showed maximal efficacy.

Using the above example, one of skill in the art would be able to determine appropriate dosages for administration to humans taking into account the known differences in clearance and metabolism between the two species.

Example 4

Time Course, Mechanism and Clinical Effects of Amyloid Clearance by Anti-SAP Antibody Experimental Protocol and Methods In an experiment using the same protocol and reagents as described in Example 1 above, different groups of 5 mice each received the same treatments as in that experiment, including the 50 mg dose of IgG fraction containing 7 mg of anti-SAP antibody, and were then killed 1, 2, 3, 4, 7, 10, 14, 21 and 25 days respectively after administration of the antibody. Plasma samples obtained from each animal at the time each group of mice was killed were stored frozen before biochemical analysis in a single batch at the end of the experiment. The spleen and liver were removed from each mouse at the time of death and processed for analysis as described in Example 1. In addition to Congo red staining to determine the extent of amyloid deposition, fixed tissue sections stained in standard fashion with haematoxylin and eosin were examined for histopathological assessment and suitably processed tissues were analysed by immunohistochemical and immunocytochemical staining for relevant proteins and cell markers using well validated routinely available reagents and methods. Some tissues were also examined by standard transmission electron microscopy. All examination, reading and scoring of slides were conducted by expert observers who were blind to the identity of the samples. Control tissues were provided by mice which had undergone the same induction of systemic AA amyloidosis but which had received control sheep IgG without anti-SAP activity.

Results

At the earliest time point, 24 hours after injection of the anti-SAP antibody, there was already massive infiltration of amyloid deposits by inflammatory cells, identified by hematoxylin and eosin staining predominantly as macrophages with some granulocytes (FIG. 4). This appearance was in marked contrast to the typically acellular amyloid deposits in control mice not receiving the antibody. Electron micrographs of tissues on day 1 showed intimate engagement of macrophages and granulocytes with the amyloid deposits (FIG. 5). Over the next few days the cellular infiltration of the amyloid deposits persisted, became overwhelmingly mononuclear, and contained increasing numbers of multinucleate giant cells surrounding and apparently engulfing the progressively fragmented and diminishing clumps of amyloid (FIG. 4). The cellular infiltrate and quantity of amyloid diminished markedly by 7-10 days and by 15 days the amyloid deposits and the infiltrating cells had almost disappeared. Histological appearances at 21 and 25 days were almost indistinguishable from normal, non amyloidotic tissue.

Immunohistochemical staining with antibody to F4/80, a global macrophage marker, identified these as the predominant component of the massive early cellular invasion of the amyloid deposits (FIG. 6). There was almost no staining for F4/80 in the amyloid deposits of control mice which did not receive anti-SAP antibody, nor was there increased staining for F4/80 in the tissues of the anti-SAP treated mice other than in and around the amyloid deposits. By day 4 there was intense staining for CD68, a marker of phagocytic activity by macrophages, in all the cells in and around the amyloid deposits, as shown by both immunoperoxidase histochemistry and by confocal microscopy (FIG. 6). The fragmented remains of the amyloid, by then mostly surrounded or internalised by macrophages and giant cells, stained with antibody to mouse AA which co-localised with staining by anti-human SAP, anti-sheep IgG and anti-mouse C3 antibodies (FIG. 6). C3 is the most abundant complement component and is responsible for the key chemotactic and opsonic activities of the complement system.

There were no significant abnormalities nor any significant differences between the groups in any of the plasma analytes tested, comprising: sodium, potassium, chloride, urea, creatinine, calcium, phosphate, alkaline phosphatase, alanine transaminase, aspartate transaminase, total protein, albumin, total cholesterol, triglycerides, glucose, total bilirubin, creatine kinase, lactate dehydrogenase.

Discussion

Administration of anti-SAP antibody to amyloidotic mice in which circulating SAP had been depleted by CPHPC, induced a very rapid and intense predominantly macrophage infiltration of the amyloid deposits. Many of these cells rapidly fused to form multinucleate giant cells which surrounded and engulfed islands of amyloid and this was followed by the swift and almost complete clearance of the deposits. By 15 days after antibody administration the amyloid had virtually disappeared and the cell population of the tissues rapidly returned to normal. There was no clinically apparent adverse effect of the treatment and plasma samples taken at the time of death from all mice in each group showed no disturbance of kidney or liver function, plasma lipids, total protein or albumin, or biochemical evidence of muscle damage. Thus essentially complete clearance of the substantial visceral amyloid deposits in these animals was clinically silent and not harmful.

The predominant cell type persistently invading amyloid deposits was identified by hematoxylin and eosin staining as macrophages and this was confirmed by electron microscopy and immunocytochemistry, as was their active role in phagocytosis and destruction of the amyloid. The presence of human SAP, sheep IgG and mouse C3 on the AA amyloid deposits within and surrounded by macrophages is consistent with the following mechanism. Anti-human SAP antibody binds to human SAP associated with the amyloid deposits and activates complement, generating the potent chemotactic attractants, C3a and C5a. Phagocytic cells, mostly macrophages, then surround and infiltrate the amyloid deposits and actively ingest the amyloid which has been opsonised by complement and IgG antibody, and macrophage mediated degradation rapidly clears the deposits.

Example 5

Validation of Simplified Protocols for Use of Anti-SAP Antibody

The standard protocol described in detail in Example 1 uses mice in which the mouse SAP gene has been deleted and the human SAP transgene inserted to provide expression of human SAP. It also used administration of CPHPC in the drinking water starting from shortly before administration of the anti-SAP antibody and continuing through the rest of the experiment. In order to explore the need for such prolonged treatment with CPHPC, a single dose of parenteral CPHPC was used in mice which were human SAP transgenic on a wild type background, rather than mouse SAP knockouts as in the previous examples. In another approach, which is critical for studies in mice with genetic modifications unrelated to SAP, amyloidotic wild type non-transgenic mice had their amyloid deposits 'loaded' with human SAP by a single parenteral injection of isolated pure human SAP.
Experimental Protocols and Methods AA amyloidosis was induced and confirmed in human SAP transgenic mice on the wild type background as in Example 1 above. They then received a single intraperitoneal injection of 1 mg of CPHPC, followed 5 hours later, in the test group (n=10), by intraperitoneal injection of 25 mg of the IgG fraction of the same sheep anti-human SAP serum as used in all previous examples. Control mice (n=8) received sheep IgG without anti-SAP activity. Sixteen days later all mice were killed for estimation of amyloid load by Congo red staining.

Subsequently 15 wild type mice in which AA amyloidosis had been induced and confirmed as detailed in Example 1, were loaded with human SAP by a single intraperitoneal injection of 10 mg per mouse of isolated pure human SAP. Human SAP injected into amyloidotic mice localises in the amyloid deposits and persists there (FIG. 7) with a half time of about 3-4 days whilst any human SAP not bound to amyloid is cleared from the circulation with a half life of about 3-4 hours.[16, 18]

Three days after the human SAP injection, when human SAP was no longer detectable in the circulation, each mouse received a single intraperitoneal injection of 50 mg of the IgG fraction of sheep anti-SAP antiserum and all were then killed 15 days after that for estimation of amyloid load by Congo red staining.
Results Amyloid deposits in the human SAP transgenic mice on the wild type background were cleared as effectively by the single dose of anti-SAP antibody as had been seen in all the previous experiments in human SAP transgenic mouse knockout mice.

Similarly, following loading of mouse AA amyloid deposits in wild type mice with passively administered human SAP, administration of anti-SAP antibody produced the same remarkable clearance of deposits as previously seen.
Discussion These results demonstrate that the presence of human SAP on the amyloid deposits and the absence of a significant concentration of human SAP in the circulation are sufficient for the therapeutic efficacy of anti-SAP antibody according to the present invention. These sufficient conditions were achieved most easily either by using a single parenteral dose of CPHPC in human SAP transgenic animals or by loading the amyloid deposits in wild type mice with human SAP via a single parenteral injection thereof. The latter model is extremely useful because it enables analysis of the mechanism of action of anti-SAP antibody in genetically modified mice (see Example 6 below) without needing to do prolonged interbreeding.

Importantly, CPHPC is essential in human subjects in whom there is always continuous production of SAP at 50-100 mg per day 6 and where it is absolutely necessary to deplete the plasma SAP before administering the anti-SAP antibody.

Example 6

Complement Dependence of Amyloid Clearance by Anti-SAP Antibody

The role of complement in amyloid clearance by anti-SAP antibody was investigated by comparing the efficiency of the treatment between mice with complement deficiency and normal complement sufficient wild type animals. Targeted deletion of the gene for C1q blocks activation of the classical complement pathway, which is initiated by binding of C1q to antibody-antigen complexes, but C3 activation, the pivotal functional step responsible for chemotaxis and opsonisation, the major biological functions of complement, can still proceed via the alternative and lectin pathways as well as by direct C3 cleavage by non-complement serine proteinases. Targeted deletion of the gene for C3 completely abrogates these functions.
Experimental Protocols and Methods AA amyloidosis was induced and confirmed, as detailed in Example 1 above, in two groups of complement deficient mice: C3 knockouts (n=14) and C1q knockouts (n=12). All mice were then loaded with human SAP and all except two in each group were treated with anti-SAP as described in Example 5, before being killed on day 15 thereafter for estimation of amyloid load.
Results In marked contrast to the effective clearance of amyloid deposits in all complement sufficient mice previously treated with anti-SAP, and described in Examples 1-5, there was still abundant amyloid present in both groups of complement deficient animals although it tended to have a more fragmented appearance than in the two complement deficient control mice of each type. The spleen amyloid scores were slightly higher in the C1q deficient (median $10^4$, range $10^2$-$10^4$) than in the C3 deficient mice (median $10^3$, range $10^2$-$10^4$) but this did not reach statistical significance.

Discussion

In mice lacking either C1q or C3, anti-SAP treatment did not clear amyloid deposits. The therapeutic efficacy of anti-SAP is thus very substantially complement dependent and is not mediated by IgG antibody alone which could, in theory, engage phagocytic cells via their Fc($\gamma$) receptors. Nevertheless the more fragmented appearance of the persistent amyloid deposits in the complement deficient mice suggested at least some effect of antibody alone. Also the trend to more clearance in C1q deficient compared to C3 deficient animals suggested that C3 activation is critical and that even in the absence of C1q and the classical pathway, which is typically activated by IgG antibody, some complement activation may be taking place.

Example 7

Requirement for Whole IgG Anti-SAP Antibody

Complement activation by IgG antibody requires the whole intact molecule, including the Fc region, and proceeds via the classical pathway initiated by binding of C1q. In some antibody-antigen systems less efficient complement activation via the alternative pathway can be mediated by the F(ab)$_2$ fragment. In order to confirm the complement dependence of amyloid clearing by anti-SAP antibody and to investigate the potential requirement for the Fc region of the antibody, the effect was tested of F(ab)$_2$ anti-SAP antibody.

Protocol and Methods

AA amyloidosis was induced and confirmed in wild type C57BL/6 mice as detailed in Example 1 above. After loading the amyloid deposits with human SAP as detailed in Example 5, groups of mice were treated with whole IgG fraction of the sheep polyclonal anti-human SAP antiserum (n=8), with buffer vehicle alone (n=10) or with the F(ab)$_2$ fragment of the IgG fraction (n=5) produced by pepsin digestion at pH 4.0. The dose of anti-SAP antibody activity injected was 7.28 mg per mouse receiving F(ab)$_2$ and 7 mg (50 mg of total IgG as usual) per mouse receiving whole IgG. All mice were killed 14 days later for estimation of amyloid load by Congo red staining.

Results

Clearance of amyloid deposits was almost complete in mice receiving IgG anti-SAP antibody, which had a median (range) spleen amyloid score of $10^0$ ($10^0$-$10^3$), compared to the massive amyloid deposits in the control mice with median (range) spleen amyloid score of $10^5$ ($10^4$-$10^5$). The mice receiving F(ab)$_2$ had less amyloid than untreated controls, median score $10^2$, range $10^0$-$10^4$, but still substantially more than the mice treated with whole IgG anti-SAP antibody.

Discussion

The molar dose of F(ab)$_2$ anti-SAP antibody used in this study was about one third greater than that of IgG antibody, given the smaller molecular weight of the F(ab)$_2$ fragment compared to whole IgG. The effect on amyloid clearance, however, was substantially less, demonstrating that the major action of the anti-SAP antibody requires the Fc region. This is not because of direct involvement of cellular recognition by Fc($\gamma$) receptors since whole IgG was even less effective in complement deficient animals than was F(ab)$_2$ in complement sufficient mice. It is likely that the high dose of F(ab)$_2$ that was used was able to activate some complement via the alternative pathway.

Example 8

Requirement for Macrophages

The histological and histochemical studies described here show that the cells which infiltrate, surround and phagocytose the amyloid deposits in mice treated with anti-SAP antibody are macrophages. In order to confirm that they are indeed responsible for the clearance of amyloid, the effect was tested of anti-SAP treatment in mice in which all macrophage activity had been inhibited by administration of liposomal clodronate. The reagents, experimental protocol and effects on macrophage function of liposomal clodronate are well established and extensively documented[22].

Protocol and Methods

After induction and confirmation of AA amyloidosis in wild type mice, using the protocol detailed in Example 1 above, all animals received a single intraperitoneal dose of 10 mg of isolated pure human SAP to load their amyloid deposits with human SAP. The test group (n=13) then received 0.3 ml of liposomal clodronate intraperitoneally immediately and on days 2, 7 and 14 days afterwards. One control group (n=12) and the test group received a single intraperitoneal dose of 50 mg of the IgG fraction of sheep anti-human SAP antiserum on day 3 after the human SAP injection. A second control group (n=12) received no anti-SAP and no other additional treatment. All mice were killed for estimation of amyloid load by Congo red staining 14 days after administration of the anti-SAP to the test and antibody control groups.

Results

Treatment with anti-SAP produced almost complete clearance of amyloid deposits compared to the group which received no antibody, median (range) spleen amyloid scores being $10^0$ (0-$10^3$) and $10^3$ ($10^3$-$10^4$) respectively. In mice which received the liposomal clodronate in a regime known to completely ablate macrophage function, there was no clearance of amyloid deposits, the amyloid load score being $10^5$ ($10^2$-$10^5$)

Discussion

The result in this experiment confirmed that macrophage function is essential for clearance of amyloid deposits by anti-human SAP antibody.

Example 9

In vitro Binding to SAP of Mouse Monoclonal Antibodies Against Human SAP

Two groups of anti-SAP monoclonals were tested separately for their binding to human SAP in vitro, and the two antibodies showing the most binding were compared with each other in different assays.

Protocols and Methods

The first set of antibodies comprised the antibodies from 7 hybridomas generated in a single conventional immunization and fusion protocol and designated SAP-1 to SAP-7, and these were tested together with a separate monoclonal, designated NH. Two of these antibodies, SAP-5 and SAP-2, are IgG2a isotype while the others are all IgG1 isotype.

The second set of antibodies comprised 6 different IgG2a monoclonals derived by standard techniques from immunization with pure human SAP and a conventional fusion to produce hybridomas which were cloned by routine methods. Supernatants from the fusion initially evaluated after the original fusion were using initially screened by standard enzyme-linked immunosorbent assay (ELISA) to identify the six mouse monoclonal anti-human SAP IgG antibodies that bound most abundantly to isolated pure human SAP which had been non-specifically non-covalently immobilised on microtiter plates. After cloning the supernatants and then the isolated antibodies were evaluated by IRMA as described below, and hybridomas clones producing IgG2a antibodies with maximal binding to SAP binding were selected.

Binding of antibodies to SAP was quantified by immunoradiometric assays performed in microtiter plates coated with immobilised pure human SAP. Bound mouse IgG was detected with radiolabelled sheep polyclonal antibody specific either for all mouse IgG classes or with isotype specific sheep antibodies against mouse IgG2a. Isolated pure human C-reactive protein (CRP) was used as a specificity control antigen. CRP is the protein most closely related to SAP and shares 55% strict residue for residue identity with it. None of the antibodies showed any reactivity at all against human CRP. Isolated pure human SAP was immobilised on the plates in several different formats: directly by non-specific, non-covalent binding to the plastic surface; by covalent attachment via its free amino groups to N-hydroxysuccinimide activated plates; by capture on specific sheep anti-human SAP antibodies coated onto the plates; and in the form of complexes of SAP with CPHPC which had been further cross-linked by covalent interaction with the bifunctional reagent BS3. In this latter configuration the SAP molecules are associated in pairs with their binding, B, faces, apposed and thereby occluded as they are when SAP is bound to amyloid fibrils. Use of SAP in this format therefore tests whether an anti-SAP antibody can access its specific epitope when the SAP molecule is bound to a macromolecular ligand. Furthermore tests were conducted in the presence of physiological calcium concentrations, as in vivo, and in the absence of free ionic calcium produced by using 10 mM EDTA in all the buffers. This approach identified whether an anti-SAP antibody is directed specifically at an epitope created by the calcium dependent organization of the ligand binding pocket on the B face of the molecule.

Binding of selected antibodies to SAP was further characterized qualitatively by double immunodiffusion in gel, and by blotting from both native agarose electrophoresis and SDS-PAGE (western blotting), all by routine standard methods. Quantitative analysis of the thermodynamic parameters of antibody binding was performed in the Biacore instrument, using isolated pure SAP alone immobilized on the chip, according to the manufacturer's instructions.

Results

The IRMA results, shown in Tables 4 and 5, showed that, among the first set of monoclonal anti-human SAP IgG antibodies, SAP-5 bound most extensively to human SAP, and that it recognised ligand-bound SAP equally well.

TABLE 4

Binding of mouse monoclonal anti-human SAP IgG antibodies to human SAP alone and to human SAP complexed with CPHPC, each directly immobilized by covalent attachment, and bound antibody detected by radiolabelled sheep anti-mouse IgG. Activity bound (d.p.m.)

|  | In EDTA mean (n = 3) | | In calcium mean (n = 3) | |
| --- | --- | --- | --- | --- |
|  | SAP alone | SAP-CPHPC complex | SAP alone | SAP-CPHPC complex |
| Buffer | 0 | 0 | 0 | 0 |
| SAP-1 IgG1 | 2683 | 3322 | 3103 | 3922 |
| SAP-2 IgG2a | 3522 | 4591 | 1723 | 2340 |

TABLE 4-continued

Binding of mouse monoclonal anti-human SAP IgG antibodies to human SAP alone and to human SAP complexed with CPHPC, each directly immobilized by covalent attachment, and bound antibody detected by radiolabelled sheep anti-mouse IgG. Activity bound (d.p.m.)

|  | In EDTA mean (n = 3) | | In calcium mean (n = 3) | |
| --- | --- | --- | --- | --- |
|  | SAP alone | SAP-CPHPC complex | SAP alone | SAP-CPHPC complex |
| SAP-3 IgG1 | 1910 | 2869 | 2847 | 3778 |
| SAP-4 IgG1 | 2149 | 3002 | 2844 | 3370 |
| SAP-5 IgG2a | 4053 | 5135 | 5583 | 6165 |
| SAP-6 IgG1 | 2021 | 2650 | 3007 | 3663 |
| SAP-7 IgG1 | 1884 | 2449 | 1651 | 2112 |
| NH IgG1 | 2514 | 3236 | 2766 | 3929 |

TABLE 5

Binding of mouse monoclonal anti-human SAP IgG antibodies to human SAP alone and human SAP complexed with CPHPC, each captured on immobilized sheep polyclonal anti-human SAP, and bound antibody detected by radiolabelled sheep anti-mouse IgG.

|  | Activity bound (d.p.m.) in calcium mean (n = 3) | |
| --- | --- | --- |
|  | SAP alone | SAP-CPHPC complex |
| Buffer | 0 | 0 |
| SAP-1 IgG1 | 1148 | 2298 |
| SAP-2 IgG2a | 1680 | 2142 |
| SAP-3 IgG1 | 853 | 1949 |
| SAP-4 IgG1 | 642 | 1647 |
| SAP-5 IgG2a | 9310 | 7125 |
| SAP-6 IgG1 | 1028 | 1931 |
| SAP-7 IgG1 | 13 | 442 |
| NH IgG1 | 1868 | 2064 |

The second set of anti-SAP antibodies were selected initially as those of IgG2a isotype with the most abundant binding in ELISA assays, and were then evaluated by IRMA using both polyvalent anti-mouse IgG and isotype specific anti-mouse IgG2a, a shown in Table 6.

TABLE 6

Binding of mouse monoclonal anti-human SAP IgG2a antibodies to human SAP directly immobilized by non-covalent attachment and detected with radiolabelled sheep polyvalent anti-mouse IgG or sheep specific anti-mouse anti-IgG2a.

| Monoclonal antibody | Activity bound (d.p.m.) polyvalent anti-mouse IgG Supernatant dilution | | |
| --- | --- | --- | --- |
|  | neat | 1/100 | 1/1000 |
| 3H8.H3 | 11766 | 6516 | 1156 |
| 3H8.H6 | 11646 | 4440 | 758 |

TABLE 6-continued

Binding of mouse monoclonal anti-human SAP IgG2a antibodies to human SAP directly immobilized by non-covalent attachment and detected with radiolabelled sheep polyvalent anti-mouse IgG or sheep specific anti-mouse anti-IgG2a.

| 3H8.H8 | 11627 | 2361 | 486 |
|---|---|---|---|
| 6H1.G2 (Abp1) | 11055 | 8571 | 2996 |
| 6H1.G3 | 12661 | 1743 | 244 |
| 6H1.H1 | 14892 | 4802 | 837 |

| | Activity bound (d.p.m.) anti-mouse IgG2a Supernatant dilution | | |
|---|---|---|---|
| Antibodies | neat | 1/100 | 1/1000 |
| 3H8.H3 | 1139 | 355 | 93 |
| 3H8.H6 | 1465 | 289 | 85 |
| 3H8.H8 | 1791 | 286 | 95 |
| 6H1.G2 Abp1 | 4799 | 3013 | 1145 |
| 6H1.G3 | 4724 | 871 | 307 |
| 6H1.H1 | 6175 | 2003 | 738 |

When all these supernatants were tested for binding to SAP in the different formats described above, there was no difference in their recognition of SAP regardless of whether the SAP was alone or cross linked, or in the presence or absence of calcium. However the clone 6H1,G2 consistently showed the most abundant binding under all conditions and was therefore selected for further study and use, and is henceforth designated as Abp1. The binding of Abp1 and SAP-5 was compared by IRMA using directly immobilized SAP on the plates and the results shown in Table 7 demonstrate clearly that Abp1 binds more abundantly than SAP-5. The lower values seen for Abp1 at the highest input concentrations, detected with polyvalent anti-mouse IgG, represent a typical antibody excess prozone phenomenon created by the limited amount of SAP antigen immobilized on the plates. The notably higher values seen for Abp1 binding at lower input concentrations provide the unequivocal evidence of its greater potency.

TABLE 7

Binding of SAP-5 and Abp1 mouse monoclonal anti-human SAP IgG2a antibodies to human SAP directly immobilized by non-covalent attachment and detected with radiolabelled sheep polyvalent anti-mouse IgG and sheep specific anti-IgG2a.

| | Monoclonal antibody concentration (µg/ml) | | | | | |
|---|---|---|---|---|---|---|
| | 100 | 10 | 1 | 0.1 | 0.01 | 0.001 |
| Activity bound (d.p.m.) polyvalent anti-mouse IgG | | | | | | |
| SAP-5 | 16229 | 15434 | 12073 | 4555 | 902 | 195 |
| Abp1 | 9376 | 10230 | 11970 | 6717 | 1676 | 544 |
| blank | 75 100 | | | | | |
| Activity bound (d.p.m.) anti-mouse IgG2a | | | | | | |
| SAP-5 | 2200 | 1979 | 1649 | 589 | 222 | 94 |
| Abp1 | 2652 | 2599 | 2251 | 1359 | 522 | 368 |
| blank | 100 77 | | | | | |

Both antibodies, SAP-5 and Abp1, bind avidly to native human SAP as shown by their precipitation of this antigen in double immunodiffusion in agarose gel with both isolated pure human SAP and SAP in whole human serum. For all different antigen antibody concentration ratios the precipitation by Abp1 was stronger than that by SAP-5 (FIG. 11).

Both antibodies, SAP-5 and Abp1, also bound avidly to native human SAP after electrophoretic separation of whole human serum in agarose gel. However when isolated pure human SAP had been denatured by boiling in SDS and reduction with mercaptoethanol, followed by SDS-PAGE, only the SAP-5 antibody was able to bind specifically to it. In contrast the Abp1 antibody no longer recognised SAP in this form.

The affinity and kinetics of binding of the two monoclonal anti-SAP antibodies are shown in Table 8, where $k_{ON}$ is the association rate constant, $k_{OFF}$ is the dissociation rate constant, and $K_D$ is the equilibrium binding constant.

TABLE 8

Monoclonal Antibodies (mAb) Affinity for hSAP determined by BIACORE

| | $k_{on}$ (M$^{-1}$ sec$^{-1}$) | $k_{off}$(sec$^{-1}$) | $K_D$(M$^{-1}$) |
|---|---|---|---|
| SAP-5 | $2 \pm 5 \times 10^4$ | $6 \pm 4 \times 10^{-5}$ | $5 \pm 4 \times 10^{-9}$ |
| Abp1 | $3.18 \pm 5 \times 10^4$ | $1.7 \pm 0.9 \times 10^{-5}$ | $1 \pm 1.7 \times 10^{-9}$ |

Discussion

These results characterize two monoclonal mouse anti-human SAP antibodies which avidly bind native human SAP with comparable and high affinity. They are both of IgG2a isotype, which is critically important for the present invention because the mechanism of amyloid clearance is complement dependent and mouse IgG2a is known to be one of the murine antibody classes capable of potently activating the classical complement pathway. Both antibodies precipitate native human SAP, confirming their avid binding. Immunoprecipitation by monoclonal antibodies is extremely unusual but in this case it reflects the polymeric nature of the SAP molecule, comprising 5 identical subunits and thereby allowing the lattice formation with bivalent IgG antibodies which is responsible for antigen antibody lattice formation leading to precipitation. Binding to native SAP is necessary for the present invention as the SAP in amyloid deposits indefinitely retains its native conformation[7]. However SAP-5 still binds to SAP after it has been completely denatured by boiling in SDS and reduction of the intrachain disulfide bridge present in each SAP protomer, showing that SAP-5 recognises a sequence epitope (FIG. 9). In contrast, Abp1 does not bind to denatured SAP, indicating that it recognises a conformational or discontinuous epitope (FIG. 9). Nevertheless both antibodies bind avidly to SAP when the SAP is itself bound to a specific ligand. This is crucial for the present invention in which the anti-SAP antibody must recognise and bind to SAP bound to amyloid fibrils in the in vivo amyloid deposits. Two polar extremes of monoclonal antibody epitope recognition are therefore presented here.

Example 10

Efficacy of Mouse Monoclonal Anti-Human SAP Antibody SAP-5 in Clearing Mouse Systemic AA Amyloid Deposits Amyloid clearance according to the present invention requires an anti-human SAP antibody which binds sufficiently avidly to the human SAP associated with amyloid deposits in the tissues and activates complement there in order to attract and activate macrophages to mediate destruction and clearance of the amyloid deposits. The capacity of various monoclonal antibodies to mediate this effect was sought in comparison with the standard sheep polyclonal anti-human SAP antibody as a positive control.

Protocols and Methods

Systemic AA amyloidosis was induced in SAP knockout C57BL/6 mice transgenic for human SAP as described in Example 1. Nine days after the final injection of casein into the mice, the presence and extent of amyloid deposition were confirmed as usual by whole body counting of amyloid after injection of a tracer dose of $^{125}$I-labelled human SAP. All mice had substantial and comparable amounts of amyloid, and were allocated into closely matched groups to receive the different treatments. One week after the tracer injection, each mouse received a single dose of 5 mg CPHPC by intraperitoneal injection, followed 5 hours later via the same route by the either the standard sheep polyclonal anti-human SAP IgG fraction (1 ml at 50 mg/ml total protein, 7 mg/ml anti-human SAP antibody) or 5 mg of each of the different monoclonal anti-human SAP antibodies. All mice were killed 21 days after the antibody injection and amyloid load determined by Congo red histology of their spleens.

Results

The results shown in Table 9 are the scores for amyloid abundance in the spleen according to the logarithmic scale set out in Example 1.

TABLE 9

The presence of amyloid in spleen of mice with systemic AA amyloidosis after treatment with CPHPC and various anti-human SAP antibodies.

| Antibody treatment | Isotype | Spleen amyloid scores in individual mice | Median (range) amyloid score |
|---|---|---|---|
| none | | $10^2, 10^2, 10^2, 10^2, 10^2, 10^2,$ $10^2, 10^2, 10^3, 10^3, 10^4$ | $10^2 (10^2$-$10^4)$ |
| polyclonal | NA | $10^0, 10^0, 10^0, 10^0, 10^0, 10^0,$ $10^0, 10^0, 10^0, 10^0$ | $10^0 (10^0$-$10^0)$ |
| monoclonal SAP-1 | IgG1 | $10^1, 10^2, 10^2, 10^2, 10^2, 10^3,$ $10^3$ | $10^2 (10^1$-$10^3)$ |
| monoclonal SAP-2 | IgG2a | $10^1, 10^2, 10^2, 10^2, 10^2, 10^3$ | $10^2 (10^1$-$10^3)$ |
| monoclonal SAP-3 | IgG1 | $10^1, 10^2, 10^2, 10^3, 10^3, 10^3,$ $10^3$ | $10^3 (10^1$-$10^3)$ |
| monoclonal SAP-4 | IgG1 | $10^3$ | $10^3$ |
| monoclonal SAP-5 | IgG2a | $10^0, 10^0, 10^0, 10^0, 10^0$ | $10^0 (10^0$-$10^0)$ |
| monoclonal SAP-6 | IgG1 | $10^1$ | $10^1$ |
| monoclonal SAP-7 | IgG1 | $10^1, 10^1, 10^2, 10^2, 10^2, 10^3,$ $10^3$ | $10^2 (10^1$-$10^3)$ |
| monoclonal SAP-5.4A | IgG1 | $10^1, 10^2, 10^2, 10^3$ | $10^2 (10^1$-$10^3)$ |
| monoclonal SAP-5.4D | IgG1 | $10^1, 10^1, 10^1, 10^1, 10^2, 10^3,$ $10^3$ | $10^1 (10^1$-$10^3)$ |

Among the monoclonal antibodies tested, only SAP-5 produced clearance of the amyloid deposits but its effect was the same as the highly reproducible and dramatic action of the sheep polyclonal antibody. Importantly SAP-5 is of the IgG2a isotype which is known to activate mouse complement while all the other monoclonals except SAP-2 were IgG 1 isotype which is not complement activating. Although SAP-2 is IgG2a isotype, its binding to SAP as quantified in vitro in Example 9, Tables 4 and 5, was notably less than that of SAP-5 and evidently was not sufficient in vivo to be effective.

Discussion

These results demonstrate that a complement activating IgG2a mouse monoclonal anti-human SAP antibody of sufficient avidity mediates amyloid clearance in vivo as effectively as sheep polyclonal anti-human SAP antibody. Furthermore this antibody recognises a sequence epitope on human SAP.

Example 11

Efficacy of Abp1 Monoclonal Anti-Human SAP Antibody

The effect of Abp1 on amyloid deposits in vivo in the mouse AA amyloidosis model was compared with the action of the standard sheep polyclonal antibody. In contrast to the SAP-5 antibody, which binds to denatured human SAP and thus recognizes a sequence epitope, the Abp1 antibody does not bind to denatured SAP and thus recognises a conformational epitope.

Experimental Protocol and Methods

AA amyloidosis was induced and confirmed in wild type C57BL/6 mice as detailed in Example 1 above. After loading the amyloid deposits with human SAP as detailed in Example 5, groups of mice were treated with 50 mg per mouse of total IgG as the whole IgG fraction of the sheep polyclonal anti-human SAP antiserum providing a dose of 7 mg of actual anti-SAP antibody (n=5), isolated purified Abp1 at a dose of 5 mg per mouse (n=10), isolated purified Abp1 at a dose of 1 mg per mouse (n=10), and, as a negative control, isolated purified monoclonal mouse IgG2a antibody specific for an unrelated human antigen and unreactive with either human SAP or any murine antigen. All mice were killed 17 days later for estimation of amyloid load by Congo red staining. Four mice in which amyloidosis had been induced, but which showed lower loads by $^{125}$I-SAP retention before animals were allocated to the different groups, were given no further treatment but were killed and their tissues processed at the same time as the treated mice for comparison at the end of the experiment.

Results

The mice treated with 5 mg of Abp1 showed the same remarkable clearance of splenic and hepatic amyloid deposits as seen with the 7 mg dose of sheep polyclonal antibody. Only trace specks of amyloid remained in the spleens of the treated mice and none at all was detected in many of the livers, contrasting sharply with the extensive splenic and hepatic amyloid deposits in all animals which received the control antibody (Table 10). Even the mice which were not treated because they had not developed sufficient amyloid load by the end of the induction period, had massive amyloid deposits in all cases (Table 10), enhancing the contrast with the striking efficacy of amyloid clearance produced by both the polyclonal antibody, as usual, and by the conformation specific Abp1 monoclonal. At the lower dose of 1 mg of Abp1 per mouse, there was reduced amyloid in the liver but no significant effect in the spleens.

TABLE 10

Effect of monoclonal mouse IgG2a anti-human SAP antibody Abp1 on visceral amyloid deposits in mice with systemic AA amyloidosis.

| Treatment | Spleen amyloid score | | Liver amyloid score | |
|---|---|---|---|---|
| | Individual mice | Median (range) | Individual mice | Median (range) |
| Control mouse IgG2a, 5 mg/mouse | $10^2, 10^3, 10^3, 10^3,$ $10^3, 10^3, 10^3, 10^4,$ | $10^3 (10^3\text{-}10^4)$ | $10^1\, 10^1, 10^1, 10^1,$ $10^1$ | $10^1$ |
| Sheep polyclonal anti-human SAP antibody, 7 mg/mouse | $10^0, 10^0, 10^0, 10^0,$ $10^0$ | $10^0$ | $0, 0, 0, 10^0, 10^0$ | $0 (0\text{-}10^0)$ |
| Abp1 monoclonal IgG2a anti-human SAP antibody, 5 mg/mouse | $10^0, 10^0, 10^0, 10^0,$ $10^0, 10^0, 10^0, 10^1,$ $10^1, 10^1$ | $10^0 (10^0\text{-}10^1)$ | $0, 0, 10^0, 10^0,$ $10^0, 10^0, 10^1, 10^1,$ $10^1, 10^1$ | $10^0 (0\text{-}10^1)$ |
| No treatment | $10^2, 10^3, 10^3, 10^4$ | | $10^0, 10^0, 10^1, 10^1$ | |

Discussion

These results demonstrate the efficacy in clearing amyloid deposits in vivo of a monoclonal anti-human SAP antibody, of the complement activating IgG2a isotype, which specifically recognizes a conformational epitope. Thus monoclonal anti-human SAP antibodies for use according to the present invention can be directed at either sequence epitopes, such as antibody SAP-5, or at conformational epitopes, such as Abp1.

Conclusions from Examples 1 and 3-11

Administration of either polyclonal or suitable mouse monoclonal anti-SAP antibodies very reproducibly causes swift and almost complete clearance of visceral amyloid deposits in AA amyloidotic mice in which human SAP is present in the amyloid deposits but is absent from the circulation, either through treatment of human SAP transgenic mice with CPHPC or by natural clearance after passive administration of human SAP to wild type mice.

There are no associated clinical or biochemical adverse effects.

Injection of the anti-SAP antibody is rapidly followed by intense infiltration of the amyloid deposits by macrophages which surround and engulf the amyloid, form many multinucleate giant cells, and destroy the deposits.

Amyloid degradation is complete by 15 days and normal histology is restored by 21-25 days after administration of a single dose of anti-SAP antibody.

Amyloid clearance requires an intact complement system and is absolutely dependent on macrophages.

Both mouse monoclonal IgG2a anti-human SAP antibodies, SAP-5 and Abp1, bind human SAP antigen with high affinity and specificity, in vitro and in vivo, and bind equally well to free SAP alone and SAP complexed with ligand.

REFERENCES

1. Pepys, M. B. (2006) Amyloidosis. *Annu. Rev. Med.,* 57: 223-241.
2. Nelson, S. R., Lyon, M., Gallagher, J. T., Johnson, E. A. and Pepys, M. B. (1991) Isolation and characterization of the integral glycosaminoglycan constituents of human amyloid A and monoclonal light-chain amyloid fibrils. *Biochem. J.,* 275: 67-73.
3. Pepys, M. B., Dyck, R. F., de Beer, F. C., Skinner, M. and Cohen, A. S. (1979) Binding of serum amyloid P component (SAP) by amyloid fibrils. *Clin. Exp. Immunol,* 38: 284-293.
4. Pepys, M. B., Booth, D. R., Hutchinson, W. L., Gallimore, J. R., Collins, P. M. and Hohenester, E. (1997) Amyloid P component. A critical review. *Amyloid: Int. J. Exp. Clin. Invest.,* 4: 274-295.
5. Nelson, S. R., Tennent, G. A., Sethi, D., Gower, P. E., Ballardie, F. W., Amatayakul-Chantler, S, and Pepys, M. B. (1991) Serum amyloid P component in chronic renal failure and dialysis. *Clin. Chim. Acta,* 200: 191-200.
6. Hawkins, P. N., Wootton, R. and Pepys, M. B. (1990) Metabolic studies of radioiodinated serum amyloid P component in normal subjects and patients with systemic amyloidosis. *J. Clin. Invest.,* 86: 1862-1869.
7. Pepys, M. B., Rademacher, T. W., Amatayakul-Chantler, S., Williams, P., Noble, G. E., Hutchinson, W. L., Hawkins, P. N., Nelson, S. R., Gallimore, J. R., Herbert, J., Hutton, T. and Dwek, R. A. (1994) Human serum amyloid P component is an invariant constituent of amyloid deposits and has a uniquely homogeneous glycostructure. *Proc. Natl. Acad. Sci. USA,* 91: 5602-5606.
8. Pepys, M. B. and Hawkins, P. N. (2003) Amyloidosis. In: Oxford Textbook of Medicine, 4th Ed., Vol. 2 (Warrell, D. A., Cox, T. M., Firth, J. D. and Benz, E. J., Jr., eds.), Oxford University Press, Oxford, pp. 162-173.
9. Baltz, M. L., Caspi, D., Hind, C. R. K., Feinstein, A. and Pepys, M. B. (1986) Isolation and characterisation of amyloid enhancing factor. In: Amyloidosis (Glenner, G. G., Osserman, E. F., Benditt, E. P., Calkins, E., Cohen, A. S, and Zucker-Franklin, D., eds.), Plenum Press, New York, pp. 115-121.
10. Wechalekar, A. D., Goodman, H. J. B., Lachmann, H. J., Offer, M., Hawkins, P. N. and Gillmore, J. D. (2007) Safety and efficacy of risk-adapted cyclophosphamide, thalidomide, and dexamethasone in systemic AL amyloidosis. *Blood,* 109: 457-464.
11. Hawkins, P. N. and Pepys, M. B. (1991) A primed state exists in vivo following regression of murine AA amyloidosis. In: Amyloid and Amyloidosis 1990 (Natvig, J. B., Forre, O., Husby, G., Husebekk, A., Skogen, B., Sletten, K. and Westermark, P., eds.), Kluwer Academic Publishers, Dordrecht, pp. 264-267.
12. Gillmore, J. D., Lovat, L. B., Persey, M. R., Pepys, M. B. and Hawkins, P. N. (2001) Amyloid load and clinical outcome in AA amyloidosis in relation to circulating concentration of serum amyloid A protein. *Lancet,* 358: 24-29.
13. Botto, M., Hawkins, P. N., Bickerstaff, M. C. M., Herbert, J., Bygrave, A. E., McBride, A., Hutchinson, W. L., Tennent, G. A., Walport, M. J. and Pepys, M. B. (1997) Amyloid deposition is delayed in mice with targeted deletion of the serum amyloid P component gene. *Nature Med.,* 3: 855-859.
14. Yamamura, K.-I., Tashiro, F., Yi, S., Wakasugi, S., Araki, S., Maeda, S, and Shimada, K. (1993) Transgenic mouse model for human genetic diseases. Mol. *Reprod. Dev.,* 36: 248-250.
15. Gillmore, J. D., Hutchinson, W. L., Herbert, J., Bybee, A., Mitchell, D. A., Hasserjian, R. P., Yamamura, K., Suzuki, M., Sabin, C. A. and Pepys, M. B. (2004) Autoimmunity and glomerulonephritis in mice with targeted deletion of the serum amyloid P component gene: SAP deficiency or strain combination? *Immunology,* 112: 255-264.
16. Pepys, M. B., Herbert, J., Hutchinson, W. L., Tennent, G. A., Lachmann, H. J., Gallimore, J. R., Lovat, L. B., Bartfai, T., Alanine, A., Hertel, C., Hoffmann, T., Jakob-Roetne, R., Norcross, R. D., Kemp, J. A., Yamamura, K., Suzuki, M., Taylor, G. W., Murray, S., Thompson, D., Purvis, A., Kolstoe, S., Wood, S. P. and Hawkins, P. N. (2002) Targeted pharmacological depletion of serum amyloid P component for treatment of human amyloidosis. *Nature,* 417: 254-259.
17. Pepys, M. B. Therapeutic agent. Pentraxin Therapeutics Limited, London (GB). U.S. Pat. No. U.S. Pat. No. 7,045, 499 B2, issued May 16, 2006.
18. Hawkins, P. N., Myers, M. J., Epenetos, A. A., Caspi, D. and Pepys, M. B. (1988) Specific localization and imaging of amyloid deposits in vivo using $^{123}$I-labeled serum amyloid P component. *J. Exp. Med.,* 167: 903-913.
19. Puchtler, H., Sweat, F. and Levine, M. (1962) On the binding of Congo red by amyloid. *J. Histochem. Cytochem.,* 10: 355-364.
20. Tennent, G. A., Dziadzio, M., Triantafillidou, E., Davies, P., Gallimore, R., Denton, P. and Pepys, M. B., (In Press) Normal Circulating Serum Amyloid P Component Concentration in Systemic Sclerosis. *Arthritis & Rheumatism* 56: 2013-7.
21. Pepys, M. B. and Hawkins, P. N. (2001) Amyloidosis. *In: Samter's Immunologic Diseases, Sixth Ed., Vol.* 1 (Austen, K. F., Frank, M. M., Atkinson, J. P. and Cantor, H., eds.), Lippincott Williams & Wilkins, Philadelphia, pp. 401-412.
22. Van Rooijen N., Van Kesteren-Hendrikx, E., 2002. Clodronate liposomes: perspectives in research and therapeutics. *J. Liposome Research.* vol. 12. pp. 81-94.

Having thus described in detail preferred embodiments of the present invention, it is to be understood that the invention defined by the above paragraphs is not to be limited to particular details set forth in the above description as many apparent variations thereof are possible without departing from the spirit or scope of the present invention. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in pharmacology and molecular biology or related fields are intended to be within the scope of the following claims.

The invention claimed is:

1. A method of treating an amyloid disease or disorder in a patient in need of such treatment, comprising administering to the patient a therapeutically effective amount of a compound which depletes circulating serum amyloid P component (SAP) in the patient and a therapeutically effective amount of an anti-SAP antibody or an antigen binding fragment thereof, wherein said antibody or said binding fragment binds to human SAP bound to amyloid in vivo in its ligand-bound conformation.

2. The method of claim 1, wherein administration of the compound and antibody or binding fragment is sequential, simultaneous or simultaneous separate.

3. A method of treating an amyloid disease or disorder in a patient in need of such treatment, comprising administering to the patient a therapeutically effective amount of a compound which depletes circulating serum amyloid P component (SAP) in the patient and a therapeutically effective amount of an anti-SAP antibody or an antigen binding fragment thereof, wherein said antibody or binding fragment binds to human SAP and, wherein the antibody is selected from the group consisting of SAP-5 and Abp1.

4. A method of treating an amyloid disease or disorder in a patient in need of such treatment, comprising administering to the patient a therapeutically effective amount of a compound which depletes circulating serum amyloid P component (SAP) in the patient and a therapeutically effective amount of an anti-SAP antibody or an antigen binding fragment thereof, wherein said antibody or binding fragment binds to human SAP and, wherein the antibody is SAP-5.

5. A method of treating an amyloid disease or disorder in a patient in need of such treatment, comprising administering to the patient a therapeutically effective amount of a compound which depletes circulating serum amyloid P component (SAP) in the patient and a therapeutically effective amount of an anti-SAP antibody or an antigen binding fragment thereof, wherein said antibody or binding fragment binds to human SAP and, wherein the antibody is Abp1.

6. The method of claim 1, wherein said antibody or said binding fragment thereof is humanized.

7. The method of claim 1, wherein the compound is a D-proline of the Formula:

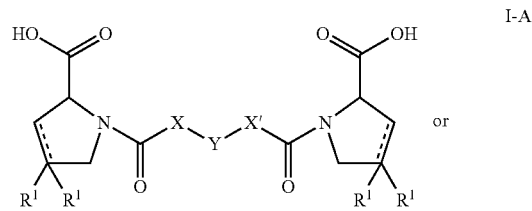

I-A

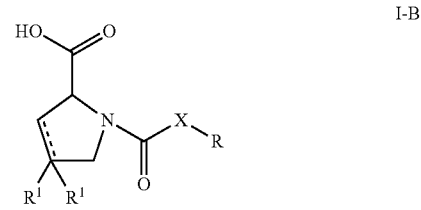

I-B wherein
R is

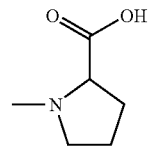

and the group

R¹ is hydrogen or halogen;

X—Y—X' is a linker having from 4 to 20 linear or straight-chain carbon atoms, wherein X is —(CH₂)ₙ—; —CH(R²)(CH₂)ₙ—; CH₂O(CH₂)ₙ—; CH₂NH—; benzyl, —C(R²)=CH—; —CH₂CH(OH)—; or thiazol-2,5-diyl; O;

Y is —S—S—; —(CH₂)ₙ—; —O—; —NH—; —N(R²)—; —CH=CH—; —NHC(O)NH—; —N(R²)C(O)N(R²)—; —N[CH₂C₆H₃(OCH₃)₂]—; —N(CH₂C₆H₅)—; —N(CH₂C₆H₅)C(O)N(CH₂C₆H₅)—; —N(alkoxyalkyl)-; N(cycloalkyl-methyl)-; 2,6-pyridyl; 2,5-furanyl; 2,5-thienyl; 1,2-cyclohexyl; 1,3-cyclohexyl; 1,4-cyclohexyl; 1,2-naphthyl; 1,4-naphthyl; 1,5-naphthyl; 1,6-naphthyl; biphenylen; or 1,2-phenylen, 1,3-phenylen and 1,4-phenylen, wherein the phenylen groups are optionally substituted by 1-4 substituents, selected from halogen, lower alkyl, lower alkoxy, hydroxyl, carboxy, —COO-lower alkyl, nitrilo, 5-tetrazol, (2-carboxylic acid pyrrolidin-1-yl)-2-oxo-ethoxy, N-hydroxycarbamimiodyl, 5-oxo[1,2,4]oxadiazolyl, 2-oxo [1,2,3,5] oxathiadiazolyl, 5-thioxo[1,2,4]oxadiazolyl and 5-tert-butylsulfanyl-[1,2,4]oxadiazolyl;

X' is —(CH₂)ₙ—; —(CH₂)ₙCH(R²)—; —(CH₂)ₙOCH₂—; —NHCH₂—; benzyl, —CH=C(R²)—; CH(OH)CH₂; or thiazol-2,5-diyl; O;

R² is lower alkyl, lower alkoxy or benzyl and n is 0-3, or a pharmaceutically acceptable salt or mono- or diester thereof.

8. The method of claim 7, wherein the compound is (R)-1-[6-[(R)-2-Carboxy-pyrrolidin-1-yl]-6-oxo-hexanoyl]pyrrolidine-2-carboxylic acid (CPHPC).

9. The method of claim 1 wherein said amyloid disease or disorder is selected from the group consisting of any form of systemic or local amyloidosis, type 2 diabetes and Alzheimer's disease.

10. The method of claim 1 wherein the antibody or binding fragment is a monoclonal antibody.

11. The method of claim 1, wherein the antibody or binding fragment binds to an epitope on human SAP which is the same as an epitope to which SAP-5 or Abp1 binds on human SAP.

12. A method of treating an amyloid disease or disorder in a patient in need of such treatment comprising depleting circulating serum amyloid P component (SAP) in the patient, wherein the improvement comprises administering to the patient a therapeutically effective amount of an anti-SAP antibody or an antigen binding fragment thereof, wherein said antibody or binding fragment binds to human SAP bound to amyloid in vivo in its ligand-bound conformation.

13. The method of claim 12, wherein said antibody or said binding fragment is humanized.

14. The method of claim 12, wherein said antibody or binding fragment is a monoclonal antibody.

15. The method of claim 12 wherein said amyloid disease or disorder is selected from the group consisting of any form of systemic or local amyloidosis, type 2 diabetes and Alzheimer's disease.

16. The method of claim 12, wherein the antibody or binding fragment binds to an epitope on human SAP which is the same as an epitope to which SAP-5 or Abp1 binds on human SAP.

17. A method of treating an amyloid disease or disorder in a patient in need of such treatment, comprising initially administering to the patient a therapeutically effective amount of a compound which depletes circulating serum amyloid P component (SAP) in the patient and thereafter administering a therapeutically effective amount of an anti-SAP antibody or an antigen binding fragment thereof, wherein said antibody or said binding fragment binds to human SAP bound to amyloid in vivo in its ligand-bound conformation.

18. The method of claim 17, wherein the compound is a D-proline of the Formula:

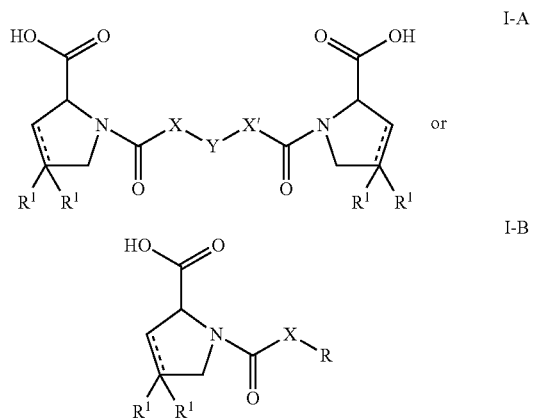

wherein

R is

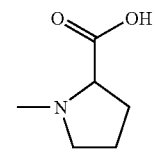

and the group

R¹ is hydrogen or halogen;

X—Y—X' is a linker having from 4 to 20 linear or straight-chain carbon atoms, wherein X is —(CH₂)ₙ—; —CH(R²)(CH₂)ₙ—; CH₂O(CH₂)ₙ—; CH₂NH—; benzyl, —C(R²)=CH—; —CH₂CH(OH)—; or thiazol-2,5-diyl; O;

Y is —S—S—; —(CH₂)ₙ—; —O—; —NH—; —N(R²)—; —CH=CH—; —NHC(O)NH—; —N(R²)C(O)N(R²)—; —N[CH₂C₆H₃(OCH₃)₂]—; —N(CH₂C₆H₅)—; —N(CH₂C₆H₅)C(O)N(CH₂C₆H₅)—; —N(alkoxyalkyl)-; N(cycloalkyl-methyl)-; 2,6-pyridyl; 2,5-furanyl; 2,5-thienyl; 1,2-cyclohexyl; 1,3-cyclohexyl; 1,4-cyclohexyl; 1,2-naphthyl; 1,4-naphthyl; 1,5-naphthyl; 1,6-naphthyl; biphenylen; or 1,2-phenylen, 1,3-phenylen and 1,4-phenylen, wherein the phenylen groups are optionally substituted by 1-4 substituents, selected from halogen, lower alkyl, lower alkoxy, hydroxyl, carboxy, —COO-lower alkyl, nitrilo, 5-tetrazol, (2-carboxylic acid pyrrolidin-1-yl)-2-oxo-ethoxy, N-hydroxycarbamimiodyl, 5-oxo[1,2,4]oxadiazolyl, 2-oxo [1,2,3,5]oxathiadiazolyl, 5-thioxo[1,2,4]oxadiazolyl and 5-tert-butylsulfanyl-[1,2,4]oxadiazolyl;

X' is —(CH₂)ₙ—; —(CH₂)ₙCH(R²)—; —(CH₂)ₙ OCH₂—; —NHCH₂—; benzyl, —CH═C(R²)—; CH(OH)CH₂; or thiazol-2,5-diyl; O;

R² is lower alkyl, lower alkoxy or benzyl and n is 0-3, or a pharmaceutically acceptable salt or mono- or diester thereof.

19. The method of claim 18, wherein the compound is (R)-1-[6-[(R)-2-Carboxy-pyrrolidin-1-yl]-6-oxo-hexanoyl] pyrrolidine-2-carboxylic acid (CPHPC).

20. The method of claim 17, wherein said antibody or said binding fragment is humanized.

21. The method of claim 17, wherein said antibody or binding fragment is a monoclonal antibody.

22. The method of claim 17, wherein said amyloid disease or disorder is selected from the group consisting of any form of systemic or local amyloidosis, type 2 diabetes and Alzheimer's disease.

23. The method of claim 17, wherein the antibody or binding fragment binds to an epitope on human SAP which is the same as an epitope to which SAP-5 or Abp1 binds on human SAP.

24. The method of any one of claim 1, 12 or 17 wherein the antibody or binding fragment binds to a linear epitope or a conformational epitope on human SAP bound to amyloid in vivo.

25. The method of claim 24 wherein the linear epitope is within amino acids 1-159 of human SAP (SEQ ID NO: 1).

26. The method of claim 25 wherein the epitope includes amino acids within residues 140-159 of human SAP (SEQ ID NO: 1).

27. The method of any one of claim 1, 2, 3, 4, 5, 6, 7, 8, 9, 11, 12, 13, 15, 16, 17, 18, 19, 20, 22, or 23 wherein the antibody or binding fragment is an antibody.

28. The method of claim 24 wherein the antibody or binding fragment is an antibody.

29. The method of claim 25 wherein the antibody or binding fragment is an antibody.

30. The method of claim 26 wherein the antibody or binding fragment is an antibody.

31. The method of any one of claim 11, 16 or 23 wherein the epitope is an epitope to which SAP-5 binds.

32. The method of any one of claim 11, 16 or 23 wherein the epitope is an epitope to which Abp-1 binds.

33. The method of claim 31 wherein the antibody or binding fragment is an antibody.

34. The method of claim 32 wherein the antibody or binding fragment is an antibody.

35. The method of any one of claim 2, 3, 4, 5, 6, 9, 11, 12, 13, 15, 16, 20, 22, or 23 wherein the administering of the compound comprises administering a D-proline compound of the Formula:

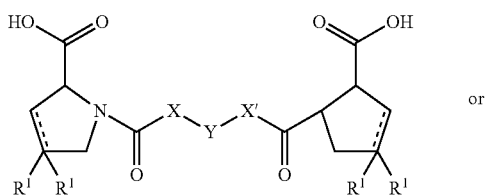

I-A or

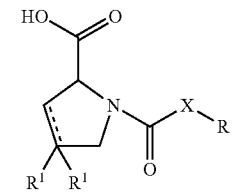

I-B wherein

R is

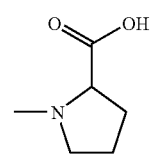

and the group

R¹ is hydrogen or halogen;

X—Y—X' is a linker having from 4 to 20 linear or straight-chain carbon atoms, wherein X is —(CH₂)ₙ—; —CH(R²)(CH₂)ₙ—; CH₂O(CH₂)ₙ—; CH₂NH—; benzyl, —C(R²)═CH—; —CH₂CH (OH)—; or thiazol-2,5-diyl; O;

Y is —S—S—; —(CH₂)ₙ—; —O—; —NH—; —N(R²)—; —CH═CH—; —NHC(O)NH—; —N(R²)C(O)N(R²)—; —N[CH₂C₆H₃(OCH₃)₂]—; —N(CH₂C₆H₅)—; —N(CH₂C₆H₅)C(O)N (CH₂C₆H₅)—; —N(alkoxyalkyl)-; N(cycloalkyl-methyl)-; 2,6-pyridyl; 2,5-furanyl; 2,5-thienyl; 1,2-cyclohexyl; 1,3-cyclohexyl; 1,4-cyclohexyl; 1,2-naphthyl; 1,4-naphthyl; 1,5-naphthyl; 1,6-naphthyl; biphenylen; or 1,2-phenylen, 1,3-phenylen and 1,4-phenylen, wherein the phenylen groups are optionally substituted by 1-4 substituents, selected from halogen, lower alkyl, lower alkoxy, hydroxyl, carboxy, —COO-lower alkyl, nitrilo, 5-tetrazol, (2-carboxylic acid pyrrolidin-1-yl)-2-oxo-ethoxy, N-hydroxycarbamimiodyl, 5-oxo[1,2,4]oxadiazolyl, 2-oxo [1,2,3, 5] oxathiadiazolyl, 5-thioxo[1,2,4]oxadiazolyl and 5-tert-butylsulfanyl-[1,2,4]oxadiazolyl;

X' is —(CH₂)ₙ—; —(CH₂)ₙCH(R²)—; —(CH₂)ₙ OCH₂—; —NHCH₂—; benzyl, —CH═C(R²)—; CH(OH)CH₂; or thiazol-2,5-diyl; O;

R² is lower alkyl, lower alkoxy or benzyl and n is 0-3, or a pharmaceutically acceptable salt or mono- or diester thereof.

36. The method of claim 35 wherein the compound is (R)-1-[6-[(R)-2-Carboxy-pyrrolidin-1-yl]-6-oxo-hexanoyl] pyrrolidine-2-carboxylic acid (CPHPC).

37. The method of claim 35 wherein the antibody or binding fragment is an antibody.

38. The method of claim 36 wherein the antibody or binding fragment is an antibody.

39. The method of any one of claim 10, 14 or 21 wherein the administering of the compound comprises administering a D-proline compound of the Formula:

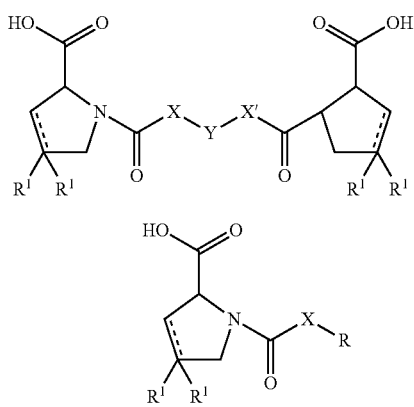

I-A or I-B wherein
R is

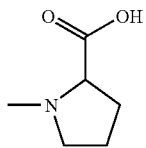

and the group
R¹ is hydrogen or halogen;
X—Y—X' is a linker having from 4 to 20 linear or straight-chain carbon atoms, wherein
X is —$(CH_2)_n$—; —$CH(R^2)(CH_2)_n$—; $CH_2O(CH_2)_n$—; $CH_2NH$—; benzyl, —$C(R^2)=CH$—; —$CH_2CH(OH)$—; or thiazol-2,5-diyl; O;

Y is —S—S—; —$(CH_2)_n$—; —O—; —NH—; —$N(R^2)$—; —CH=CH—; —NHC(O)NH—; —$N(R^2)C(O)N(R^2)$—; —$N[CH_2C_6H_3(OCH_3)_2]$—; —$N(CH_2C_6H_5)$—; —$N(CH_2C_6H_5)C(O)N(CH_2C_6H_5)$—; —N(alkoxyalkyl)-; N(cycloalkyl-methyl)-; 2,6-pyridyl; 2,5-furanyl; 2,5-thienyl; 1,2-cyclohexyl; 1,3-cyclohexyl; 1,4-cyclohexyl; 1,2-naphthyl; 1,4-naphthyl; 1,5-naphthyl; 1,6-naphthyl; biphenylen; or 1,2-phenylen, 1,3-phenylen and 1,4-phenylen, wherein the phenylen groups are optionally substituted by 1-4 substituents, selected from halogen, lower alkyl, lower alkoxy, hydroxyl, carboxy, —COO-lower alkyl, nitrilo, 5-tetrazol, (2-carboxylic acid pyrrolidin-1-yl)-2-oxo-ethoxy, N-hydroxycarbamimiodyl, 5-oxo[1,2,4]oxadiazolyl, 2-oxo [1,2,3,5]oxathiadiazolyl, 5-thioxo[1,2,4]oxadiazolyl and 5-tert-butylsulfanyl-[1,2,4]oxadiazolyl;
X' is —$(CH_2)_n$—; —$(CH_2)_nCH(R^2)$—; —$(CH_2)_nOCH_2$—; —$NHCH_2$—; benzyl, —$CH=C(R^2)$—; $CH(OH)CH_2$; or thiazol-2,5-diyl; O;
$R^2$ is lower alkyl, lower alkoxy or benzyl and
n is 0-3,
or a pharmaceutically acceptable salt or mono- or diester thereof.

40. The method of claim 39 wherein the compound is (R)-1-[6-[(R)-2-Carboxy-pyrrolidin-1-yl]-6-oxo-hexanoyl] pyrrolidine-2-carboxylic acid (CPHPC).

41. An anti-serum amyloid P component (SAP) antibody or an antigen binding fragment thereof, wherein said antibody or binding fragment binds to human SAP and, wherein the antibody is Abp1.

42. The antibody or binding fragment of claim 41 which is an antibody.

* * * * *